US012616656B2

(12) United States Patent
Kent et al.

(10) Patent No.: US 12,616,656 B2
(45) Date of Patent: May 5, 2026

(54) ADVENTITIAL PAINTING MODALITY OF LOCAL DRUG DELIVERY TO ABATE INTIMAL HYPERPLASIA

(71) Applicants: University of Virginia Patent Foundation, Charlottesville, VA (US); Wisconsin Alumni Research Foundation, Madison, WI (US)

(72) Inventors: Kenneth Craig Kent, Charlottesville, VA (US); Lian-Wang Guo, Madison, WI (US); Takuro Shirasu, Charlottesville, VA (US); Bowen Wang, Charlottesville, VA (US); Shaoqin Gong, Middleton, WI (US); Nisakorn Yodsanit, Madison, WI (US)

(73) Assignees: University of Virginia Patent Foundation, Charlottesville, VA (US); Wisconsin Alumni Research Foundation, Madison, WI (US)

( * ) Notice: Subject to any disclaimer, the term of this patent is extended or adjusted under 35 U.S.C. 154(b) by 241 days.

(21) Appl. No.: 18/562,898

(22) PCT Filed: May 20, 2022

(86) PCT No.: PCT/US2022/072462
§ 371 (c)(1),
(2) Date: Nov. 21, 2023

(87) PCT Pub. No.: WO2022/246462
PCT Pub. Date: Nov. 24, 2022

(65) Prior Publication Data

US 2024/0238198 A1 Jul. 18, 2024

Related U.S. Application Data

(60) Provisional application No. 63/191,443, filed on May 21, 2021.

(51) Int. Cl.

| | |
|---|---|
| ***A61K 9/107*** | (2006.01) |
| ***A61K 9/51*** | (2006.01) |
| ***A61K 31/436*** | (2006.01) |
| ***A61K 31/7076*** | (2006.01) |
| ***A61K 49/00*** | (2006.01) |
| ***A61P 9/10*** | (2006.01) |
| *B82Y 5/00* | (2011.01) |

(52) U.S. Cl.
CPC .............. *A61K 9/1075* (2013.01); *A61K 9/51* (2013.01); *A61K 31/436* (2013.01); *A61K 31/7076* (2013.01); *A61K 49/0021* (2013.01); *A61P 9/10* (2018.01); *B82Y 5/00* (2013.01)

(58) Field of Classification Search
None
See application file for complete search history.

(56) References Cited

U.S. PATENT DOCUMENTS

2018/0042844 A1* 2/2018 Kent .................... A61K 31/436
2018/0358118 A1* 12/2018 Bagaev .................. G16B 30/00

OTHER PUBLICATIONS

Dockery et al., "Chapter Four—Dendronized Systems for the Delivery of Chemotherapeutics," Advances in Cancer Research, vol. 139, 2018, pp. 1-7. (Year: 2018).*

Yellepeddi et al., "Biotinylated Poly(amido)amine (PAMAM) Dendrimers as Carriers for Drug Delivery to Ovarian Cancer Cells In Vitro," Anticancer Research, 29: 2933-2944 (2009). (Year: 2009).*

Boogaarts, J. et. al, Use of a Novel Absorbable Hydrogel for Augmentation of Dural Repair: Results of a Preliminary Clinical Study, Oper. Neurosurg. 57 (2005) 146-151.

Brinkman, A, et. al, Aminoflavone-loaded EGFR-targET.ed unimolecular micelle nanoparticles exhibit anti-cancer effects in triple negative breast cancer, Biomaterials 101 (2016) 20-31.

Chen, G. et. al, A review on core-shell structured unimolecular nanoparticles for biomedical applications, Adv Drug Deliv Rev 130 (2018) 58-72.

Chen, G. et. al, KE108-conjugated unimolecular micelles loaded with a novel HDAC inhibitor thailandepsin-A for targET.ed neuroendocrine cancer therapy, Biomaterials 97 (2016) 22-33.

Chen, G. et. al, Multi-functional self-fluorescent unimolecular micelles for tumor-targeted drug delivery and bioimaging, Biomaterials 47 (2015) 41-50.

Chen, G. et. al, Tumor-Targeted pH/redox dual-sensitive unimolecular nanoparticles for efficient siRNA delivery, Journal of Controlled Release 259 (2017) 105-114.

Chen, G. et. al, Unimolecular Micelle-Based Hybrid System for Perivascular Drug Delivery Produces Long-Term Efficacy for Neointima Attenuation in Rats, Biomacromolecules 18(7) (2017) 2205-2213.

Gao, W. et. al, Nanoparticle-Hydrogel: A Hybrid Biomaterial System for Localized Drug Delivery, Ann Biomed Eng 44(6) (2016) 2049-2061.

Guo, J. et. al, Image-guided and tumor-targET.ed drug delivery with radiolabeled unimolecular micelles, Biomaterials 34 (2013) 8323-8332.

(Continued)

*Primary Examiner* — Aradhana Sasan
(74) *Attorney, Agent, or Firm* — Thomas | Horstemeyer, LLP

(57) ABSTRACT

In one aspect, the disclosure relates to unimolecular micelles having N-hydroxysuccinimide ester (NHS), sulfo-NHS terminal groups, or other adhesive terminal groups, compositions including the same, methods of making the same, and methods of treating intimal hyperplasia in a subject using the same. In some aspects, the unimolecular micelles can further include fluorescent labels or drugs for treating intimal hyperplasia. In one aspect, the unimolecular micelles and compositions comprising the same are biocompatible, non-toxic, and non-inflammatory. In another aspect, the unimolecular micelles and compositions are substantially free from hydrogel, or are completely free from hydrogel. In still another aspect, the disclosed compositions and methods can be easily and quickly deployed in the operating room. Also disclosed is a method of applying the unimolecular micelles and compositions via direct penbrush painting.

20 Claims, 35 Drawing Sheets

(56) References Cited

OTHER PUBLICATIONS

Hess, C.N. et. al, Saphenous vein graft failure after coronary artery bypass surgery: insights from Prevent IV, Circulation 130(17) (2014) 1445-51.
Jaskula-Sztul, R. et. al, AB3-loaded and tumor-targeted unimolecular micelles for medullary thyroid cancer treatment, J Mater Chem B 5 (2017) 151-159.
Jaskula-Sztul, R. et. al, Targeted Delivery of Thailandepsin A using Unimolecular Micelles to Improve Antitumor Effect in Carcinoids, Journal of Surgical Research 186 (2014) 546.
Jaskula-Sztul, R. et. al, Thailandepsin A-loaded and octreotide-functionalized unimolecular micelles for targET. ed neuroendocrine cancer therapy, Biomaterials 91 (2016) 1-10.
Kithcart, A.P. et. al, ACC/AHA Versus ESC Guidelines for Diagnosis and Management of Peripheral Artery Disease: JACC Guideline Comparison, J Am Coll Cardiol 72(22) (2018) 2789-2801.
Kord Forooshani, P. et. al, Recent approaches in designing bioadhesive materials inspired by mussel adhesive protein, Journal of Polymer Science Part A: Polymer Chemistry 55(1) (2017) 9-33.
Leichner, C. et. al, N-Hydroxysulfosuccinimide Esters versus Thiomers: A Comparative Study Regarding Mucoadhesiveness, Molecular Pharmaceutics 16(3) (2019) 1211-1219.
Liu, H. et. al, Less harmful acidic degradation of poly(lacticco-glycolic acid) bone tissue engineering scaffolds through titania nanoparticle addition, Int J Nanomedicine 1(4) (2006) 541-545.
Lynn, A.D. et. al, Characterization of the in vitro macrophage response and in vivo host response to poly(ET.hylene glycol)-based hydrogels, J Biomed Mater Res A 93(3) (2010) 941-53.
Meschaninova, M.I., Novel Convenient Approach to the Solid-Phase Synthesis of Oligonucleotide Conjugates, Molecules 24(23) (2019).
Nair, L. et. al, Folic Acid Conjugated δ-Valerolactone-Poly(ET. hylene glycol) Based Triblock Copolymer as a Promising Carrier for Targeted Doxorubicin Delivery, PLOS One 8(8) (2013) e70697.
Nam, S. et. al, Polymeric Tissue Adhesives, Chemical Reviews 121 (2021) 11336-11384.
Osbun, J.W. et. al, A Multicenter, Single-Blind, Prospective Randomized Trial to Evaluate the SafET.y of a PolyET. hylene Glycol Hydrogel (Duraseal Dural Sealant System) as a Dural Sealant in Cranial Surgery, World Neurosurgery 78(5) (2012) 498-504.
Pandey, N. et. al, Biodegradable Nanoparticles Enhanced Adhesiveness of Mussel-Like Hydrogels at Tissue Interface, Adv Healthc Mater 7 (2017) 1701069.
Preul, M. et. al, Toward optimal tissue sealants for neurosurgery: use of a novel hydrogel sealant in a canine durotomy repair model, Neurosurgery 53 (2003) 1189-1198.
Qazvini, N.T. et. al, Synthesis and characterization of gelatin nanoparticles using CDI/NHS as a non-toxic cross-linking system, J Mater Sci Mater Med 22(1) (2011) 63-9.
Rafuse, M. et. al, Layer-specific arterial micromechanics and micro-structure: Influences of age, anatomical location, and processing technique, J Biomech 88 (2019) 113-121.
Rees, C. et. al, Safety and efficacy of a novel polyethylene glycol hydrogel sealant for watertight dural repair, Journal of neurosurgery 106 (2007) 52-58.
Salva, R. et. al, Polymersome shape transformation at the nanoscale, ACS Nano 7(10) (2013) 9298-311.
Sam, S. et. al, Semiquantitative Study of the EDC/NHS Activation of Acid Terminal Groups at Modified Porous Silicon Surfaces, Langmuir 26(2) (2010) 809-814.
Shi, X. et. al, Periadventitial Application of Rapamycin-Loaded Nanoparticles Produces Sustained Inhibition of Vascular Restenosis, PLOS One 9(2) (2014) e89227.
Taggart, D.P. et. al, A Randomized Trial of External Stenting for Saphenous Vein Grafts in Coronary Artery Bypass Grafting, Ann Thorac Surg 99(6) (2015) 2039-45.
Wallace, D. et. al, A Tissue Sealant Based on Reactive Multifunctional PolyET.hylene Glycol. J. Biomed. Mater. Res. 58 (2001) 545-555.
Wang, B. et. al, A paradigm of endothelium-protective and stent-free anti-restenotic therapy using biomimET.ic nanoclusters, Biomaterials 178 (2018) 293-301.
Wang, B. et. al, Perk Inhibition Mitigates Restenosis and Thrombosis: A Potential Low-Thrombogenic Antirestenotic Paradigm, JACC Basic Transl Sci 5(3) (2020) 245-263.
Wang, Y. et. al, Carboplatin-Complexed and cRGD-Conjugated Unimolecular Nanoparticles for TargET.ed Ovarian Cancer Therapy, Macromolecule bioscience 17 (2016) 1600292.
Xu, W. et. al, Octreotide-functionalized and resveratrol-loaded unimolecular micelles for targET.ed neuroendocrine cancer therapy, Nanoscale 5 (2013) 9924-9933.
Zhao Y, Xie R, Yodsanit N, Ye M, Wang Y, Wang B, Guo L-W, Kent KC, Gong S. Hydrogen peroxide-responsive plateIET. membrane-coated nanoparticles for thrombus therapy. Biomaterial Sciences (2021) 75:109732.
Zhao, L. et. al, An intraocular drug delivery system using targET.ed nanocarriers attenuates rET.inal ganglion cell degeneration, Journal of Controlled Release 247 (2017) 153-166.

* cited by examiner

C

C

ADVENTITIAL PAINTING MODALITY OF LOCAL DRUG DELIVERY TO ABATE INTIMAL HYPERPLASIA

CROSS REFERENCE TO RELATED APPLICATIONS

This application is a U.S. national phase application under 35 U.S.C. 371 of International Patent Application No. PCT/US2022/072462, filed on May 21, 2022, which claims the benefit of and priority to U.S. Provisional Application No. 63/191,443 filed on May 21, 2021 both of which are incorporated herein by reference in their entireties.

STATEMENT REGARDING FEDERALLY SPONSORED RESEARCH OR DEVELOPMENT

This invention was made with government support under grant numbers R01HL143469, R01HL129785, and R01 HL133665 awarded by the National Institutes of Health. The government has certain rights in the invention.

BACKGROUND

Coronary artery disease, carotid artery disease, and peripheral artery disease share a common etiology of atherosclerosis, which affects around one third of adults and is a leading cause of death. The prevalence of atherosclerosis increases with age and is predicted to grow globally. While endovascular approaches (e.g., stenting) are gaining momentum in current clinical managements of atherosclerosis, open surgical reconstructions such as bypass grafting, endarterectomy, and arteriovenous fistula, collectively over a million per year in the US alone, remain the gold standard surgical procedures for cardiovascular diseases and hemodialysis access. Unfortunately, treatments often fail, due to neointimal hyperplasia (IH) in the vessel wall that narrows the lumen. Despite numerous investigations, currently no suitable clinical method exists to prevent post-operative failure of open vascular reconstructions.

A major medical problem is the persistent lack of approved therapeutic methods to prevent postoperative IH, which leads to high-rate failure of open vascular reconstructions such as bypass grafting. Hydrogel has been widely used in preclinical trials for perivascular drug administration to mitigate postoperative IH. However, bulky hydrogel is potentially pro-inflammatory, posing a significant hurdle to clinical translation.

With a long-term goal to meet this medical need, a perivascular drug administration system using unimolecular micelle (UM) was previously developed. This nanoparticle formulation consisted of a hydrophobic “core” to provide high drug-loading capacity and sustained drug release, and a hydrophilic “shell” that enabled solubility. To retain the soluble UM from flowing away at the desired area, a thermosensitive phase-transition hydrogel was synthesized to hold UM in the perivascular space. This UM/hydrogel hybrid system proved to be effective in hampering IH when applied periadventitially in a rat model. However, potential issues remained, especially in the perspective of translation toward a clinical utility, including the following: 1) The semi-solid hydrogel can momentarily be dislocated from the treatment site. 2) Once the UM-containing hydrogel decomposes, the UM can diffuse away. 3) Due to gel bulkiness, this UM/hydrogel system is not applicable at some locations with limited perivascular space. 4) During the decomposition process of bulk hydrogel, local pH can decrease due to large amounts of acidic by-products, which can accelerate gel degradation while inciting inflammation. Bulk gels may also produce degradation products that are generally pro-inflammatory.

Among other solutions, perivascular drug-releasing polymer cuffs, wraps, or meshes reduced IH in earlier preclinical studies, but these devices can impinge on the vessel, imposing physical harm.

It would be advantageous to have a nanoparticle platform that can be periadventitially applied and is effective at preventing or reducing IH but that does not require a bulky hydrogel and does not physically harm vessels. It would further be advantageous if the nanoparticle platform could be easily and quickly applied in clinical settings and was biocompatible, non-toxic, and/or non-inflammatory. These needs and other needs are satisfied by the present disclosure.

SUMMARY

In accordance with the purpose(s) of the present disclosure, as embodied and broadly described herein, the disclosure, in one aspect, relates to unimolecular micelles having N-hydroxysuccinimide ester (NHS), sulfo-NHS terminal groups, or other adhesive terminal groups, compositions including the same, methods of making the same, and methods of treating intimal hyperplasia in a subject using the same. In some aspects, the unimolecular micelles can further include fluorescent labels or drugs for treating intimal hyperplasia. In one aspect, the unimolecular micelles and compositions comprising the same are biocompatible, non-toxic, and non-inflammatory. In another aspect, the unimolecular micelles and compositions are substantially free from hydrogel, or are completely free from hydrogel. In still another aspect, the disclosed compositions and methods can be easily and quickly deployed in the operating room. Also disclosed is a method of applying the unimolecular micelles and compositions via direct pen-brush painting.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1A: Design of UM-NHS. FIG. 1B: Mode-1: UM-NHS crosslinked at pH 8.0 and its periadventitial application via soaking with the artery. FIG. 1C: Mode-2: Periadventitial application of non-crosslinked UM-NHS via soaking with the artery. FIG. 1D: Mode-3: Periadventitial application of non-crosslinked UM-NHS via pen-brush painting onto the artery.

FIG. 3A: Representative H&E-stained artery cross-sections. Scale bar: 200 μm. FIG. 3B: High-mag images. Scale bar: 50 μm. FIG. 3C: Morphometric quantification: mean±SEM, n=6-8 rats, as indicated by the data points in each plot. Statistics: ANOVA and Bonferroni test: *P<0.05. r.u., relative unit. The calculation of I/M ratio, normalized intimal thickness, and stenosis rate are described in the Examples.

FIG. 4A: Photographic illustration of periadventitial application of UM. The photos show post-application (14 days) neck bulging in Mode-1 and lack of thereof in Mode-2. Note that the Cy5 fluorophore appeared blue at higher concentrations but not at lower concentrations (see FIG. 6A). Shown on the right are representative H&E-stained cross-sections including undissectible surrounding tissues in Model-1. Scale bar: 200 μm. FIG. 4B: Representative images of Masson's trichrome staining of artery cross-sections. Scale bar: 200 μm. FIG. 4C: Quantification: mean±SEM, n=3 rats. Statistics: ANOVA and Bonferroni test: *P<0.05. r.u., relative unit.

FIGS. 5A-5B: Immunostaining of the inflammation marker CD68. Shown in FIG. 5A are representative staining images. Scale bar: 50 μm. Non-treatment control: no UM application. Quantification: mean±SEM, n=3 rats. Statistics: ANOVA and Bonferroni test: *P<0.05, P<0.01, P<0.001. FIGS. 5C-5D: Immunostaining of the apoptosis marker active (cleaved) caspase-3. Shown in FIG. 5C are representative staining images. Scale bar: 50 μm. Non-treatment control: no UM application. Quantification: mean±SEM, n=3 rats. Statistics: ANOVA and Bonferroni test: *P<0.05.

FIG. 6A: Photographic illustration of the UM-NHS painting approach (Mode-3). Left panel: Balloon-injured common carotid artery after painting UM-NHS with a pen brush (pointed by white arrow head). Note the painted UM-NHS appeared colorless. Right panel: Rat neck at post-surgery Day 14. Note the lack of neck bulging. FIG. 6B: Representative images of Cy5 fluorescence from artery cross-sections. Cy5 was conjugated on UM. Images were taken on the sections of arteries collected right after UM application (day 0) or 7 days post application (day 7). Autofluorescence from elastic laminae profiles the medial layer. Scale bar: 200 μm. FIG. 6C: Representative H&E-stained artery cross-sections. Scale bar: 200 μm (low mag), 50 μm (high mag). FIG. 6D: Morphometric quantification: mean±SEM, n=6 rats. Statistics: ANOVA and Bonferroni test: *P<0.05, **P<0.01. r.u., relative unit. The calculation of I/M ratio, standardized intimal thickness, and stenosis rate is described in the Examples.

FIGS. 7A-7B: Immunostaining of the inflammation marker CD68. Shown in A are representative staining images. Scale bar: 50 μm. Non-treatment control: no UM application. Quantification: mean±SEM, n=3 rats. Statistics: ANOVA and Bonferroni test: *P<0.05, **P<0.01. FIGS. 7C-7D: Immunostaining of the apoptosis marker active (cleaved) caspase-3. Shown in C are representative staining images. Scale bar: 50 μm. Non-treatment control: no UM application. Quantification: mean±SEM, n=3 rats. Statistics: ANOVA and Bonferroni test: *P<0.05.

FIG. 8B: PAMAM-PVL-COOH ($CDCl_3$, δ 4.08, 2.34, and 1.67 ppm). FIG. 8C: UM-OH ($CDCl_3$, δ 6.5-7.0, 4.08, 3.64, 2.34, and 1.67 ppm). FIG. 8D: UM-NHS ($CDCl_3$, δ 6.5-7.0, 4.08, 3.64, 2.84, 2.34, and 1.67 ppm).

FIG. 9A: Size distribution of UM-NHS under DLS. FIG. 9B: TEM image of UM-NHS. FIG. 9C: FTIR spectra of PAMAM-PVL-OH and PAMAM-PVL-COOH. The peak at 1552 $cm^{-1}$, C═O stretching of carboxylic, only observed in PAMAM-PVL-COOH (black line) while the peak at 1726 $cm^{-1}$, C═O stretching of carbonyl (ester bond) was found in both compounds. FIG. 9D: FTIR result demonstrating the C═O stretching (1778 $cm^{-1}$), and N—O stretching (1637 $cm^{-1}$), the specific peaks found in NHS ester structure, from UM-NHS (grey line) but not observed in UM-OH (black line). FIG. 9E: The release profiles of rapamycin in Mode-1 (UM-NHS with 4-arm PEG gel), Mode-2 and -3 (UM-NHS alone) in PBS (pH 7.4) at 37° C. up to 60 days.

FIG. 11A: Representative H&E-stained artery cross-sections. Scale bar: 200 μm (low mag), 50 μm (high mag). FIG. 11B: Morphometric quantification: mean±SEM, n=6 rats. Statistics: ANOVA and Bonferroni test: P<0.01, *P<0.001. r.u., relative unit. The calculation of I/M ratio, standardized intimal thickness, and stenosis rate is described in the Examples.

FIG. 12A: Statistical analysis. Representative H&E-stained artery cross-sections. Scale bar: 200 μm (low mag), 50 μm (high mag). FIG. 12B: Representative H&E-stained artery cross-sections (low mag images). Statistics: ANOVA and Bonferroni test: P<0.01, *P<0.001. r.u., relative unit. The calculation of I/M ratio, standardized intimal thickness, and stenosis rate is described in the Examples.

FIG. 13C shows retention of ahNP on the adventitial ECM. When brushed on a vein graft or artery, the unimolecular micelle NP is adhesive (ahNP) since the PEG-sulfo-NHS ester reacts with the $NH_2$ group rich on the adventitial ECM. A real image SEM image shows decellularized human adventitial ECM (scale bar: 1 μm).

Figure 1:
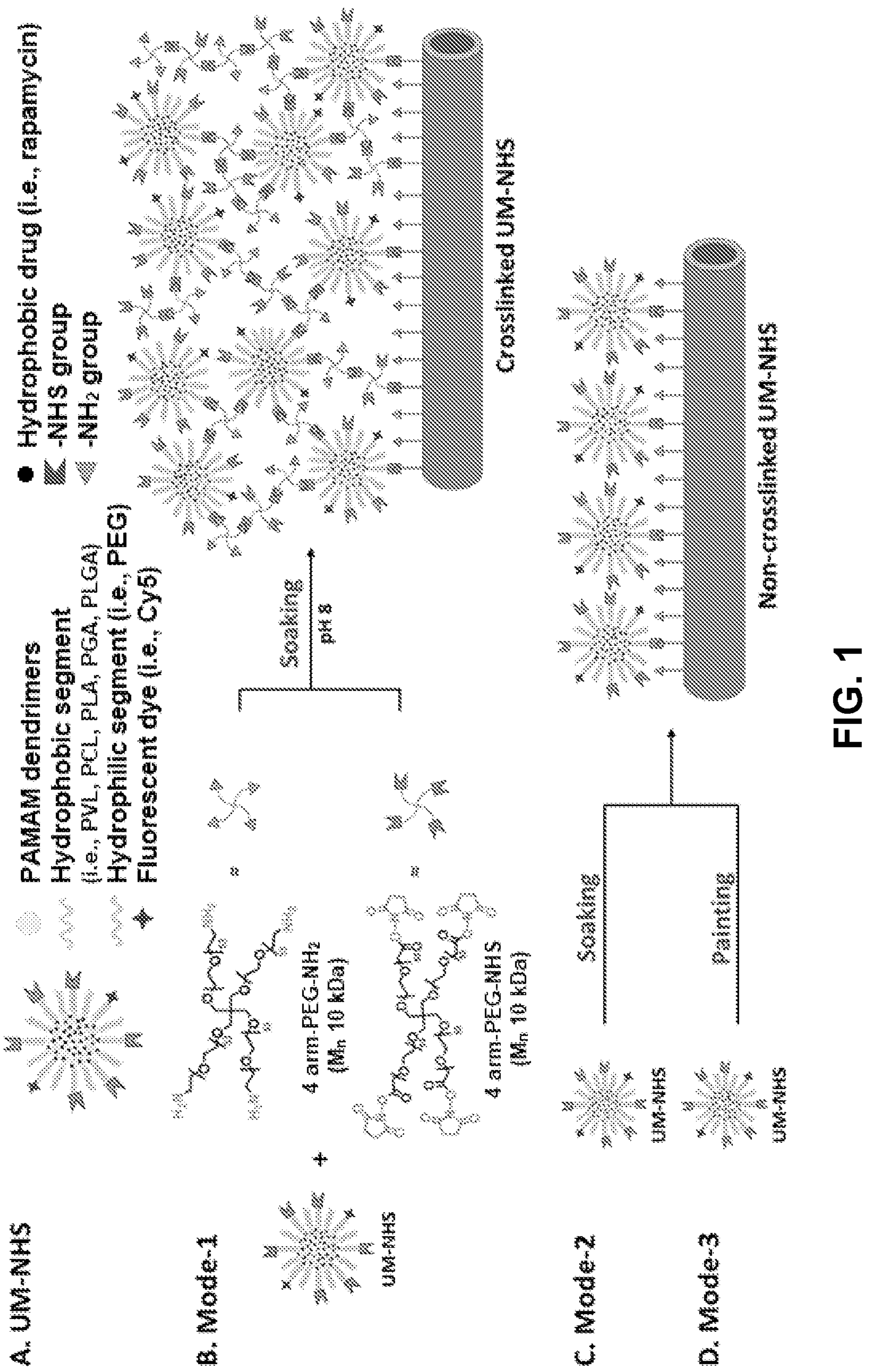
FIGS. 1A-1D show a schematic of the design and application of UM-NHS.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Disclosed herein are tissue-adhesive unimolecular micelles (UM) that can covalently link to adventitia. In one aspect, periadventitial applications can be tested by soaking the vessel in a UM solution. In a further aspect, to retain drug loading capacity while omitting a bulky hydrogel, UM can be crosslinked into a network (Mode-1) or applied non-crosslinked UM (Mode-2) for comparison. In some aspects, severe tissue fibrosis, inflammation, and cell death occurred in Mode-1, but not in Mode-2. In a still further aspect, disclosed herein is simpler approach of directly painting (pen-brush) the vessel surface with non-crosslinked UM (Mode-3). Further in this aspect, while consuming only 1/10 of drug-loaded UM, Mode-3 produced a pronounced intimal hyperplasia (IH) abrogating effect yet with minimized tissue toxicity. This is the first report of directly and covalently painting nanoparticles onto the adventitia to efficaciously and safely mitigate IH.

In one aspect, disclosed herein is method for treating or preventing intimal hyperplasia in a subject, the method including the step of applying a composition comprising unimolecular micelles to the adventitia of a vessel in the subject. In some aspects, the unimolecular micelles comprise N-hydroxysuccinimide ester (NHS) or sulfo-NHS terminal groups and the NHS terminal groups or sulfo-NHS terminal groups form amide bonds with the adventitia. In some aspects, other terminal groups can also be employed in the disclosed compositions and methods. In one aspect, the unimolecular micelles can have aldehyde terminal groups, or can have terminal groups chemically modified to include other functional molecules such as, for example, dopamine, which can be linked to a carboxylic acid group through an amide bond.

In another aspect, the unimolecular micelles have the structure

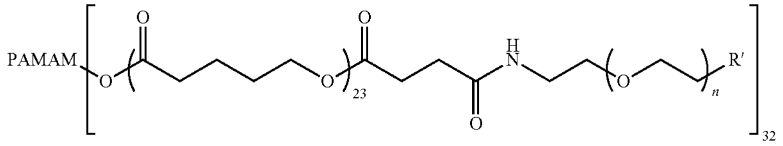

wherein PAMAM comprises polyamidoamine dendrimers;

wherein n is from about 10 to about 230; and wherein R' is a combination of an NHS ester or a sulfo-NHS ester, methoxy groups, and, optionally, a fluorescent label.

In one aspect, n can be about 10, 25, 50, 75, 100, 125, 150, 175, 200, or about 230, or a combination of any of the foregoing values, or a range encompassing any of the foregoing values. In one aspect, when n is about 10, the PEG unit of the unimolecular micelles can be a PEG 450, when n is about 22, the PEG can be a PEG 1000, and when n is about 230, the PEG can be a PEG 10,000. Other commercial PEG products with values of n falling in the disclosed range can also be employed in the methods and compositions of the present disclosure. In an aspect, the fluorescent label can be Cy5, ICG, AF647, Cy7-azide, IR-820, CY7.5-$NH_2$, DY-547, DY-647, Cy5.5, DY-700-COOH, DY-676-$NH_2$, NileBlue, NileRed, Hostasol, Norbonenyl coumarin, aminocoumarin, nitrobenzoxadiazole (NBD), rhodamine, fluorescein, BODIPY, or any combination thereof.

In another aspect, the unimolecular micelles have an average molecular weight of from about 15 kDa to about 520 kDa, or of about 15, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, or about 520 kDa, or a combination of any of the foregoing values, or a range encompassing any of the foregoing values. In one aspect, a molecular weight of about 520 kDa can correspond to a PCL unit where n is 45, a PEG 10,000 component, and a dendrimer with 33 arms.

In one aspect, the PAMAM hydrophobic segment can have an average molecular weight of from about 20 to about 170 kDa, and the PAMAM segment linked to a PEG segment can have a molecular weight of from about 86 to about 330 kDa.

In one aspect, the unimolecular micelles can have an average hydrodynamic diameter of from about 15 to about 200 nm, or of about 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or about 200 nm, or a combination of any of the foregoing values, or a range encompassing any of the foregoing values. In another aspect, the unimolecular micelles have a polydispersity index (PDI) of from about 0.2 to about 0.3, or of about 0.2, 0.21, 0.22, 0.23, 0.24, 0.25, 0.26, 0.27, 0.28, 0.29, or about 0.3, or a combination of any of the foregoing values, or a range encompassing any of the foregoing values. In still another aspect, the unimolecular micelles have a zeta potential of from about 0.7 mV to about 2.5 mV, or of about 0.7, 0.8, 0.9, 1, 1.1, 1.2, 1.3, 1.4, 1.5, 1.6, 1.7, 1.8, 1.9, 2, 2.1, 2.2, 2.3, 2.4, or about 2.5 mV, or a combination of any of the foregoing values, or a range encompassing any of the foregoing values.

In some aspects, the composition further includes a drug for treating intimal hyperplasia, such as, for example, rapamycin, sirolimus, paclitaxel, apabetalone, JQ1, EPZ5676, centrinone-B, GSK2606414, EED226, UNC1999, tubastatin-A, disulfiram, halofugenone, resveratrol, a DOT1L inhibitor, or any combination thereof. In one aspect, the DOT1L inhibitor can be pinometostat (EPZ5676). In any of these aspects, the composition can include from about 0.1 to about 20 wt % of the drug, or about 0.1, 1, 2, 3, 4, 5, 6, 7, 8, 9, 10, 11, 12, 13, 14, 15, 16, 17, 18, 19, or about 20 wt %, or a combination of any of the foregoing values, or a range encompassing any of the foregoing values.

In one aspect, applying the composition to the adventitia comprises pen-brush painting the composition to the vessel. In any of these aspects, the compositions can be substantially free or completely free of hydrogel and can be biocompatible, non-toxic, and/or non-inflammatory.

In one aspect, the subject can be a mammal such as, for example, a human, rat, mouse, rabbit, or pig. In another aspect, IH is prevented or reduced for a period of at least two weeks.

In one aspect, the NHS ester terminal group reacts with an amine in an extracellular matrix (ECM) protein to form an amide bond, releasing NHS or a derivative thereof. In some aspects, the derivative of NHS is sulfo-NHS and the method further includes removing the sulfo-NHS from an adventitial site of application such as, for example, by using gauze.

In any of these aspects, performing the method can deliver a dose of from about 5 μg to about 10 mg per kg of body weight μg of the drug to the vessel adventitia, or about 5, 25, 50, 100, 150, 200, 250, 300, 350, 400, 450, 500, 550, 600, 650, 700, 750, 800, 850, 900, or about 950 μg per kg of body weight, or about 1, 2, 3, 4, 5, 6, 7, 8, 9, or about 10 mg per kg of body weight.

Also disclosed are the unimolecular micelles described herein and compositions including the unimolecular micelles. In some aspects, the compositions include at least one excipient such as, for example, a carbonate buffer. In another aspect, the compositions are substantially free of hydrogel or are completely free of hydrogel, are non-toxic, and are non-inflammatory. In any of these aspects, the unimolecular micelles may not be crosslinked in the compositions.

In one aspect, the epigenetic writer DOT1L has been identified as a master pathogenic target; its genetic silencing abated IH in rats. In a further aspect, aiming at a potential clinical utility suitable for open vascular reconstructions, tissue-adhesive nanoparticles for drug delivery have been designed that can be easily brushed over reconstructed vessel surface. In one aspect, this can be termed a “painting” method as it is simple and gentle, needing only a pen brush, and quick, within 30 seconds. In a further aspect, this nanoplatform has been used to administer the DOT1L-selective inhibitor Pinometostat (EPZ5676), which abated IH without endothelial toxicity in healthy rats and in obese Zucker rats with human-like disease backgrounds. In a still further aspect, although the clinical trial drug Pinometostat was used as a test agent, the disclosed compositions and methods can be used as a modular drug delivery nanoplatform that is broadly applicable for other small molecule drugs.

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by," "comprising," "comprises," "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of".

As used in the specification and the appended claims, the singular forms "a," "an" and "the" include plural referents unless the context clearly dictates otherwise. Thus, for example, reference to "a drug," "a hydrogel," or "a unimolecular micelle," includes, but is not limited to, mixtures or combinations of two or more such drugs, hydrogels, or unimolecular micelles, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y.' The range can also be expressed as an upper limit, e.g. 'about x, y, z, or less' and should be interpreted to include the specific ranges of 'about x,' 'about y', and 'about z' as well as the ranges of 'less than x', less than y', and 'less than z'. Likewise, the phrase 'about x, y, z, or greater' should be interpreted to include the specific ranges of 'about x,' 'about y,' and 'about z' as well as the ranges of 'greater than x,' greater than y,' and 'greater than z.' In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

"Intimal hyperplasia" or IH as used herein refers to the thickening of the tunica intima of a blood vessel as a complication during a surgical reconstruction (e.g. bypass grafting), removal of plaque, or injury. IH can cause complications including late bypass graft failures. In one aspect, the methods and systems disclosed herein can prevent or reduce the severity of IH.

"Adventitia" as used herein refers to the outermost layer of a blood vessel. In one aspect, the adventitia can contain connective tissue containing collagen and elastin, nerves, and, in some instances, smaller blood vessels that supply larger blood vessels with oxygen and/or nutrients. In an aspect, the adventitia provides structural support to blood vessels.

As used herein, "unimolecular micelles" and "nanoparticles" refer to a polymeric compound such as, for example, a polyamidoamine dendrimer, that forms a micellar structure in aqueous solution. In some aspects, unimolecular micelles or nanoparticles containing sulfo-NHS terminal groups can be referred to as "adhesive nanoparticles." In one aspect, the unimolecular micelles or nanoparticles disclosed herein can be or include PAMAM-PVL-PEG-$OCH_3$/OH/NHS or PAMAM-PVL-PEG-$OCH_3$/OH/sulfo-NHS, optionally labeled with a fluorescent tag such as, for example, Cy5. Other terminal groups are also contemplated for the unimolecular micelles and/or nanoparticles including, but not limited to, aldehyde terminal groups, dopamine terminal groups, and combinations thereof.

As used herein, the terms "optional" or "optionally" means that the subsequently described event or circumstance can or cannot occur, and that the description includes instances where said event or circumstance occurs and instances where it does not.

As used herein, the term "prevent" or "preventing" refers to precluding, averting, obviating, forestalling, stopping, or hindering something from happening, especially by advance action. It is understood that where reduce, inhibit, or prevent are used herein, unless specifically indicated otherwise, the use of the other two words is also expressly disclosed.

As used herein, the terms "treating" and "treatment" can refer generally to obtaining a desired pharmacological and/or physiological effect. The effect can be, but does not necessarily have to be, prophylactic in terms of preventing or partially preventing a disease, symptom, or condition thereof, such as intimal hyperplasia. The effect can be therapeutic in terms of a partial or complete cure of a disease, condition, symptom, or adverse effect attributed to the disease, disorder, or condition. The term "treatment" as used herein can include any treatment of intimal hyperplasia in a subject, particularly a human, and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder, or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, e.g., such as treating the pain of a subject by administration of an analgesic agent even though such agent does not treat the cause of the pain.

As used herein, "non-toxic" and "biocompatible" refer to compounds and compositions that do not cause harm to living tissues and/or do not cause the death of cells within the tissues when the tissues are exposed to the compounds and/or compositions for either a short time or a period of hours, days, weeks, or even months. Meanwhile, "non-inflammatory" refers to compounds and compositions that do not cause an inflammatory response in tissues or organs when the compounds and/or compositions contact the tissues or organs. In one aspect, the unimolecular micelles and/or nanoparticles disclosed herein are non-toxic, biocompatible, and non-inflammatory.

Unless otherwise specified, temperatures referred to herein are based on atmospheric pressure (i.e. one atmosphere).

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

Aspects

The present disclosure can be described in accordance with the following numbered aspects, which should not be confused with the claims.

Aspect 1. A method for treating or preventing intimal hyperplasia in a subject, the method comprising applying a composition comprising unimolecular micelles to adventitia of a vessel in the subject.

Aspect 2. The method of aspect 1, wherein the unimolecular micelles comprise N-hydroxysuccinimide ester (NHS) terminal groups, aldehyde terminal groups, dopamine terminal groups, or any combination thereof.

Aspect 3. The method of aspect 2, wherein the NHS terminal groups comprise sulfo-NHS terminal groups.

Aspect 4. The method of aspect 2 or 3, wherein the NHS terminal groups form amide bonds with the adventitia.

Aspect 5. The method of any one of the preceding aspects, wherein the unimolecular micelles comprise the structure

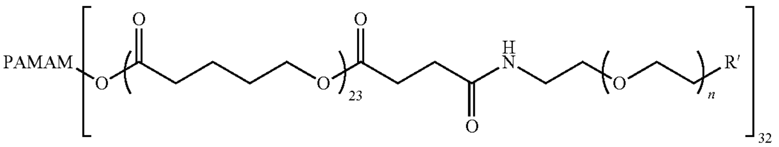

wherein PAMAM comprises polyamidoamine dendrimers;

wherein n is from about 10 to about 230; and wherein each R' in the unimolecular micelles is individually selected from the NHS ester, a methoxy group, or a fluorescent label.

Aspect 6. The method of aspect 5, wherein the fluorescent label comprises Cy5, ICG, AF647, Cy7-azide, IR-820, CY7.5-$NH_2$, DY-547, DY-647, Cy5.5, DY-700-COOH, DY-676-$NH_2$, NileBlue, NileRed, Hostasol, Norbonenyl coumarin, amino-coumarin, nitrobenzoxadiazole (NBD), rhodamine, fluorescein, BODIPY, or any combination thereof.

Aspect 7. The method of any one of the preceding aspects, wherein the unimolecular micelles have an average molecular weight of from about 15 kDa to about 520 kDa.

Aspect 8. The method of any one of the preceding aspects, wherein the unimolecular micelles have an average hydrodynamic diameter of from about 15 nm to about 200 nm.

Aspect 9. The method of aspect 8, wherein the unimolecular micelles have an average hydrodynamic diameter of from about 20 to about 100 nm.

Aspect 10. The method of any one of the preceding aspects, wherein the unimolecular micelles have a polydispersity index (PDI) of from about 0.2 to about 0.3.

Aspect 11. The method of aspect 10, wherein the unimolecular micelles have a polydispersity index (PDI) of from about 0.22 to about 0.23.

Aspect 12. The method of any one of the preceding aspects, wherein the unimolecular micelles have a zeta potential of from about 0.7 mV to about 2.5 mV.

Aspect 13. The method of aspect 12, wherein the unimolecular micelles have a zeta potential of from about 1 mV to about 2 mV.

Aspect 14. The method of any one of the preceding aspects, wherein the composition further comprises a drug for treating intimal hyperplasia.

Aspect 15. The method of aspect 14, wherein the drug comprises rapamycin, sirolimus, paclitaxel, apabetalone, JQ1, EPZ5676, centrinone-B, GSK2606414, EED226, UNC1999, tubastatin-A, disulfiram, halofugenone, resveratrol, a DOT1L inhibitor, or any combination thereof.

Aspect 16. The method of aspect 15, wherein the DOT1L inhibitor comprises pinometostat (EPZ5676).

Aspect 17. The method of any one of aspects 14-16, wherein the composition comprises from about 0.1 to about 20 wt % of the drug.

Aspect 18. The method of any one of the preceding aspects, wherein the applying the composition to the adventitia comprises pen-brush painting the composition to the vessel.

Aspect 19. The method of any one of the preceding aspects, wherein the subject is a mammal.

Aspect 20. The method of aspect 19, wherein the mammal is a human, rat, mouse, rabbit, or pig.

Aspect 21. The method of any one of the preceding aspects, wherein IH is prevented or reduced for a period of at least 2 weeks.

Aspect 22. The method of any one of aspects 2-21, wherein the NHS ester terminal group reacts with an amine in an extracellular matrix (ECM) protein to form an amide bond, releasing NHS or a derivative thereof.

Aspect 23. The method of aspect 22, wherein the derivative of NHS is sulfo-NHS and the method further comprises removing the sulfo-NHS from an adventitial site of application.

Aspect 24. The method of aspect 23, wherein the sulfo-NHS is removed by contacting the adventitial site of application with gauze.

Aspect 25. The method of any one of the preceding aspects, wherein performing the method delivers a dose of from about 5 μg per kg of body weight to about 10 mg per kg of body weight of the drug to the vessel adventitia.

Aspect 26. A unimolecular micelle comprising the structure

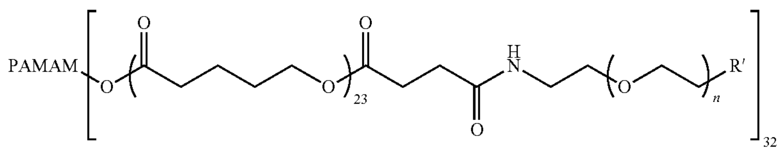

wherein PAMAM comprises polyamidoamine dendrimers;

wherein n is from about 10 to about 230; and wherein each R' in the unimolecular micelles is individually selected from the NHS ester, a methoxy group, or a fluorescent label.

Aspect 27. The unimolecular micelle of aspect 26, wherein the unimolecular micelle has an average molecular weight of at least about 15 kDa.

Aspect 28. The unimolecular micelle of aspect 26 or 27, wherein the fluorescent label comprises Cy5, ICG, AF647, Cy7-azide, IR-820, CY7.5-$NH_2$, DY-547, DY-647, Cy5.5, DY-700-COOH, DY-676-$NH_2$, NileBlue, NileRed, Hostasol, Norbonenyl coumarin, Amino-coumarin, nitrobenzoxadiazole (NBD), rhodamine, fluorescein, BODIPY, or any combination thereof.

Aspect 29. The unimolecular micelle of any one of aspects 26-28, wherein the unimolecular micelle has an average hydrodynamic diameter of from about 15 to about 200 nm.

Aspect 30. The unimolecular micelle of aspect 29, wherein the unimolecular micelle has an average hydrodynamic diameter of from about 20 to about 100 nm.

Aspect 31. The unimolecular micelle of any one of aspects 26-30, wherein the unimolecular micelle has a polydispersity index (PDI) of from about 0.2 to about 0.3.

Aspect 32. The unimolecular micelle of aspect 31, wherein the unimolecular micelle has a polydispersity index (PDI) of from about 0.22 to about 0.23.

Aspect 33. The unimolecular micelle of any one of aspects 26-32, wherein the unimolecular micelle has a zeta potential of from about 0.7 mV to about 2.5 mV.

Aspect 34. The unimolecular micelle of aspect 33, wherein the unimolecular micelle has a zeta potential of from about 1 mV to about 2 mV.

Aspect 35. A composition comprising one or more unimolecular micelles according to any one of aspects 26-34.

Aspect 36. The composition of aspect 35, wherein the one or more unimolecular micelles are not crosslinked.

Aspect 37. The composition of aspect 35 or 36, wherein the composition further comprises a drug for treating intimal hyperplasia.

Aspect 38. The composition of aspect 37, wherein the drug comprises rapamycin, sirolimus, paclitaxel, apabetalone, JQ1, EPZ5676, centrinone-B, GSK2606414, EED226, UNC1999, tubastatin-A, disulfiram, halofugenone, resveratrol, a DOT1L inhibitor, or any combination thereof.

Aspect 39. The composition of aspect 38, wherein the DOT1L inhibitor comprises pinometostat (EPZ5676).

Aspect 40. The composition of any one of aspects 37-39, wherein the composition comprises from about 0.1 to about 20 wt % of the drug.

Aspect 41. The composition of any one of aspects 37-40, further comprising at least one excipient.

Aspect 42. The composition of aspect 41, wherein the at least one excipient comprises a carbonate buffer.

Aspect 43. The composition of any one of aspects 37-42, wherein the composition is free of hydrogel.

Aspect 44. The composition of any one of aspects 37-43, wherein the composition is non-toxic.

Aspect 45. The composition of any one of aspects 37-44, wherein the composition is non-inflammatory.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Materials and Methods

Materials

Rapamycin was purchased from LC Laboratories (Woburn, MA). Methoxy-PEG-$NH_2$ (mPEG-$NH_2$, $M_n$=5 kDa), $NH_2$—PEG-OH ($M_n$=5 kDa), maleimide-PEG-$NH_2$ (Mal-PEG-$NH_2$, $M_n$=5 kDa), 4-arm PEG-$NH_2$ ($M_n$=10 kDa), and 4-arm PEG-NHS ($M_n$=10 kDa) were acquired from Biochempeg Scientific Inc. (Watertown, MA, USA). Cy5 dye was obtained from Lumiprobe Corporation (Hallandale Beach, FL, USA). Succinic anhydride, tin(II) 2-ethylhexanoate ($Sn(Oct)_2$), and 4-dimethylamino pyridine (DMAP) were purchased from Thermo Fisher scientific (Waltham, MA, USA). DSC was obtained from Oakwood Chemical (Estill, SC, USA). Anhydrous pyridine was acquired from EMD Millipore Corporation (Billerica, MA, USA). Other chemicals were obtained from Sigma-Aldrich (St. Louis, MO).

Preparation of Tissue-Adhesive UM-NHS

Synthesis of PAMAM-PVL-COOH

PAMAM-PVL-OH was first synthesized using PAMAM-OH ($4^{th}$ generation, 31.50 mg, 6.33 μmol) and δ-valerolactone (411.19 μL, 4.43 mmol) through ring-opening polymerization with a catalyst, $Sn(Oct)_2$ (0.48 μL, 1.48 μmol) at 120° C. for 24 hr as previously reported. Then, PAMAM-PVL-OH (350 mg, 4.47 μmol, $M_n$ 20-170 kDa) and succinic anhydride (279.88 mg, 2.80 mmol) were dissolved in anhydrous dichloromethane (DCM) (20 mL) before adding DMAP (427.10 mg, 3.50 mmol). The reaction was stirred at room temperature for 48 hr under $N_2$ atmosphere. To collect the product, the mixture was slowly precipitated in cold diethyl ether and centrifuged at 10,000 g for 10 min. The precipitate was purified by dialysis against DI water using a regenerated cellulose (RC) dialysis membrane tubing (molecular weight cut-off (MWCO) 8 kDa) for 48 hr, and lyophilized under vacuum.

Synthesis of Cy5-PEG-$NH_2$

Cy5-SH (5 mg, 7 μmol) was conjugated with Mal-PEG-$NH_2$ (29 mg, 5.8 μmol) in dimethyl sulfoxide (DMSO) (5 mL) through Michael addition. The reaction was stirred at room temperature for 24 hr in the dark. Thereafter, it was purified by dialysis against DI water for 24 h using a RC dialysis membrane tubing (MWCO 2 kDa). The product was obtained after lyophilization under vacuum.

Synthesis of PAMAM-PVL-PEG-OCH/Cy5/OH (UM-OH)

PAMAM-PVL-COOH (100 mg, 1.28 μmol, $M_n$ 20-170 kDa), NHS (33.90 mg, 294.58 μmol), and 1-ethyl-3-(3-dimethylaminopropyl) carbodiimide (EDC) (47.06 mg, 245.48 μmol) were first dissolved in DCM (30 mL) to activate the carboxylic terminal, as reported. mPEG-$NH_2$ (306.85 mg, 61.37 μmol, 5 kDa), HO-PEG-$NH_2$ (306.85 mg, 61.37 μmol, 5 kDa), and $NH_2$—PEG-Cy5 (25.57 mg, 5.11 μmol, 5 kDa) were then added into the reaction. The reaction was stirred at 4° C. to RT for 48 hr under $N_2$ atmosphere in the dark. The crude product was collected by precipitation in cold diethyl ether and dialyzed against DI water using a RC dialysis membrane tubing (MWCO 8 kDa) for 48 hr in the dark before lyophilization to obtain UM-OH.

Synthesis of PAMAM-PVL-PEG-OCH/Cy5/NHS Ester (UM-NHS)

PAMAM-PVL-PEG-$OCH_3$/OH/Cy5 (120 mg, 0.50 μmol, $M_n$ 86-330 kDa) was dissolved in DCM. Then, DSC (10.32 mg, 20.15 μmol) and anhydrous pyridine (5.0 μL, 30.22 μmol) were added into the mixture in order to generate NHS terminal. The reaction mixture was stirred at room temperature for 24 hr in the dark. To remove unreacted PEG and DSC, the solution was dialyzed against DCM using a RC dialysis membrane tubing (MWCO 15 kDa) for 24 hr and precipitated in diethyl ether. The precipitate was then lyophilized to yield UM-NHS, which was stored in the dark.

Synthesis of UM-Sulfo-NHS

UM-sulfo-NHS was prepared as with UM-NHS but a sulfo-NHS group was used in place of the NHS group in the procedure outlined previously.

Preparation of Rapamycin-Loaded UM-NHS

UM-NHS (60 mg) and rapamycin (20 mg) were dissolved in DMSO (5 mL). DI water (15 mL) was added dropwise into the mixture to provide rapamycin-loaded UM-NHS, as previous reported. The unloaded rapamycin was removed by dialysis against DI water using a RC dialysis membrane tubing (MWCO 15 kDa) for 24 hr before lyophilization.

Characterization

The chemical structures and molecular weights were determined by the $^1H$ NMR spectroscopy (Bruker Avance-400 MHz) (FIGS. 8A-8D), and gel permeation chromatography (GPC, Viscotek, Malvern), respectively. The NMR samples were prepared in deuterated chloroform (CDCl3) (~5 mg/mL) while the samples for GPC analysis were dissolved in dimethylformamide (DMF) (~0.5 to 1.0 mg/mL). Fourier-transform infrared (FTIR) spectroscopy (Tensor 27, Bruker) was used to confirm the carboxylic acid at the terminal in PAMAM-PVL-COOH, and NHS functional groups in UM-NHS. The hydrodynamic diameter and zeta-potential of UM-NHS were measured using a dynamic light scattering (DLS) machine (Zetasizer NanoZS90, Malvern). To measure the size, PAMAM-PVL-OH and PAMAM-PVL-COOH were prepared in chloroform (0.02 mg/mL) while UM-NHS was suspended in DI water (0.02 mg/mL). All samples were prepared in DI water to evaluate the surface charges (0.02 mg/mL) (FIGS. 9A-9E). Additionally, morphology of UM-NHS was observed under transmission electron microscope (TEM, FEI Tecnai TF-30) using phosphotungstic acid (PTA) as a negative stain. To prepare the TEM sample, the UM-NHS solution (0.05 mg/mL in DI water) was dropped onto a TEM grid (Formvar/Carbon coated copper grids, 200 mesh). The grid is air dried and a drop of PTA solution (1%, pH 7) was added onto the grid. After 30 seconds, excessive PTA solution was removed by a filter paper, and the grid was air dried. The rapamycin loading content was quantified by HPLC (Elite LaChrom, Hitachi) at 278 nm using 0.5 mg/ml of drug-loaded UM-NHS in DMSO.

Quantification of Rapamycin Release from UM-NHS In Vitro

The amounts of rapamycin released from Mode-1 (UM-NHS with gel), Mode-2 (UM-NHS), and Mode-3 (UM-NHS) were measured following the reported protocol with some modifications. In Mode-1, UM-NHS (1 mL, 250 mg/mL in $NaHCO_3$ buffer, pH 8), 4-arm PEG-NHS (0.75 mL, 320 mg/mL in $NaHCO_3$ buffer, pH 8), and 4-arm PEG-$NH_2$ (0.75 mL, 320 mg/mL in $NaHCO_3$ buffer, pH 8) were mixed and enclosed in RC dialysis bag (MWCO 8 kDa). The dialysis bag was then immersed in PBS (25 mL, pH 7.4) with 0.2% polysorbate 80 and kept in horizontal shaker (140 rpm) at 37° C. At the time points indicated in FIG. 9E, supernatants (1 mL) were collected and replaced with fresh media (1 mL). The amounts of rapamycin released to the supernatants were quantified by HPLC at 278 nm. In Mode-2 and Mode-3, UM-NHS (1 mL, 250 mg/ml in $NaHCO_3$, pH 8) was transferred to a dialysis bag (MWCO 8 kDa), followed by the same procedures as in Mode-1.

Animals

All animal experiments were carried out in accordance with the Guide for the Care and Use of Laboratory Animals (National Institutes of Health), and the protocols are approved by the Institutional Animal Care and Use Committee of University of Virginia. Sprague-Dawley rats were purchased from Charles River Laboratories (Wilmington, MA). Females differ from males in body structure and artery size which affect the IH-inducing open surgery. To omit this confounding variable, only male rats were used for experiments (300-330 g body weight). They were kept in isolation racks in an air-conditioned room with 12 hr-12 hr light-dark cycle, fed with a normal diet, and free to access food and water.

Open Surgery Model of Rat Carotid Artery Balloon Injury to Induce IH

Balloon injury was performed as described in the literature. In brief, rats were anesthetized with inhalation of isoflurane (5% for induction and 2% for maintenance), a midline incision was made in the neck, and carotid arteries were dissected. A 2-Fr. balloon catheter was inserted via an arteriotomy on the external carotid artery, and the entire length of common carotid artery (CCA) was injured by withdrawing the balloon catheter inflated at 1.5 atm. The balloon was withdrawn straight 3 times, while at the 4th time retracted with rotation. In all surgeries, the omohyoid muscle was resected when dissecting carotid arteries, and sternocleidomastoid muscle was also resected at the time of periadventitial crosslinked-UM application. Bupivacaine (up to 8 mg/kg) was locally injected at the incision site, and carprofen (5 mg/kg) and buprenorphine (0.05 mg/kg) were subcutaneously injected after the surgery. The rats were euthanized 14 days after surgery and CCAs were collected after perfusion fixation with 4% paraformaldehyde (PFA). The collected arteries were fixed in 4% PFA for 12-24 hr, paraffin-embedded, and then processed for morphometric analysis.

Periadventitial Application of Rapamycin-Encapsulated UM-NHS and UM-Sulfo-NHS

Figure 10:
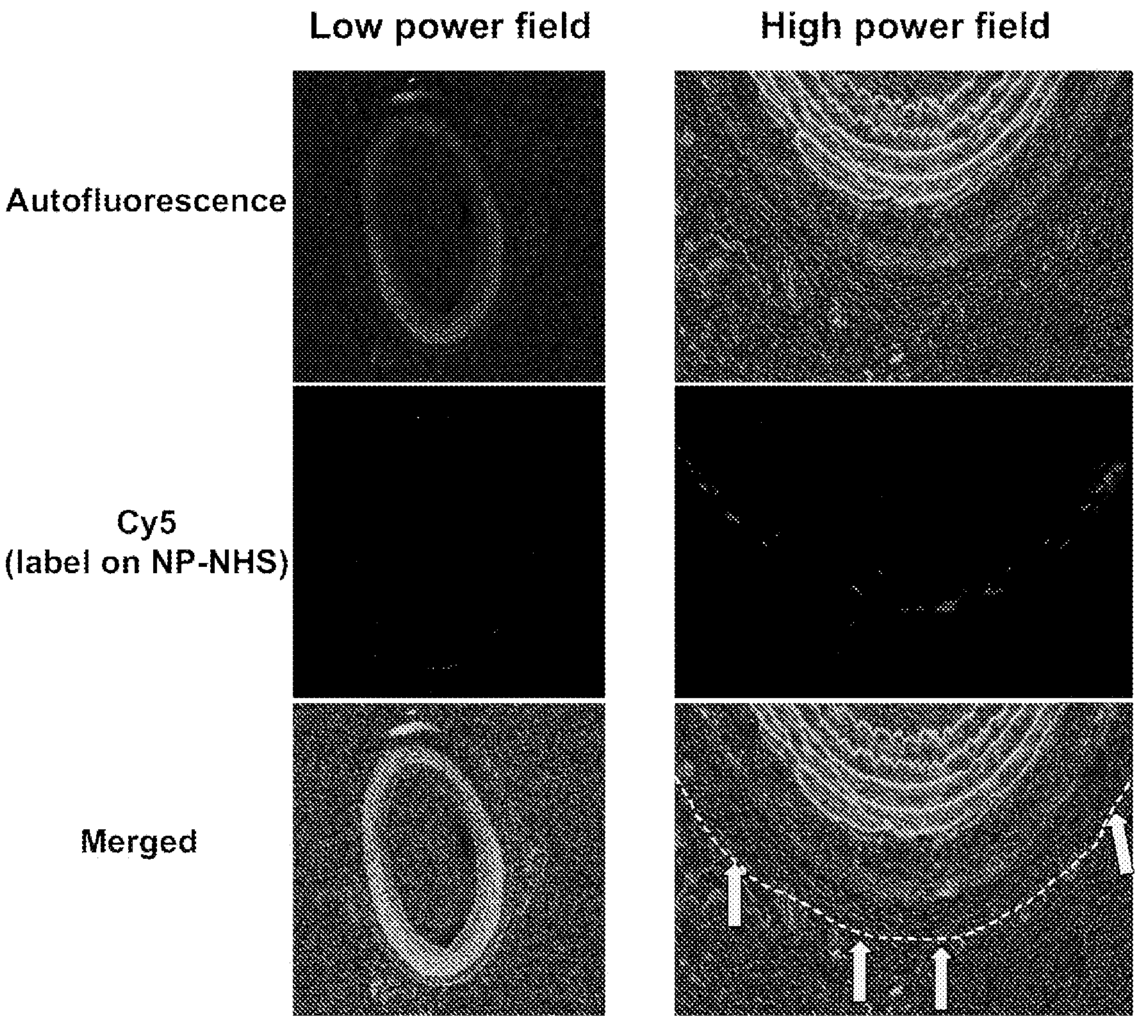
FIG. 10 shows retained Cy5 fluorescence of UM at 14 days post application. Experiment was performed as described for FIGS. 3A-3C. Shown are representative images taken from paraffin-embedded cross-sections of injured arteries. The arteries were collected at 14 days after balloon injury and periadventitial application of cross-linked UM (Model-1). The medial layer is profiled by elastin autofluorescence. Arrows point to the border between the adventitial and periadventitial layers.

The UM-NHS nanoparticle as a drug carrier was applied in 3 different modes. In Mode-1, UM-NHS were crosslinked into a network. PEG-based gels with NHS and amine (—$NH_2$) terminal groups, which are commonly used for sealant, are utilized to form the crosslinked system. As illustrated in FIGS. 1A-1B, the 4-arm PEG-NH2 (10 kDa) can react with both UM-NHS and 4-arm PEG-NHS (10 kDa) to form a network. For each rat, 250 mg/mL UM-NHS (120 μL), 320 mg/mL of 4-arm PEG-$NH_2$ (90 μL), and 320 mg/mL of 4-arm PEG-NHS (90 μL) were first prepared in $NaHCO_3$ buffer with a pH value of 8. These components were mixed right before perivascular application. In Mode-2, UM-NHS were not crosslinked and remained in solution (250 mg/mL in $NaHCO_3$ buffer, pH 8) until periadventitial application (FIG. 1C). In these two modes, immediately after balloon injury of the CCA, UM-NHS (crosslinked or non-crosslinked) were contained in a cup formed with a Parafilm membrane (Bemis Company, Inc, Neenah, WI) around the injured artery. In Mode-1, solidification of the components was observed (~1 min), while in Mode-2, the arteries were incubated for 15 min and gently rinsed the outer surface of the arteries with PBS. Cy5 Fluorescence imaging confirmed the presence of UM-NHS even 14 days after the periadventitial application (FIG. 10). In Mode-3, the CCA was quickly rinsed with PBS drops, and cleaned with gauze. A pen brush was then used to dip into the non-crosslinked UM-NHS solution (250 mg/mL in NaHCO3 buffer, pH 8) and to paint the solution throughout the outer surface of the injured artery (FIG. 1D). The painting process was completed in 30 seconds. The excess solution on the artery was immediately removed with gauze. For each periadventitial application mode, empty UM-NHS (no rapamycin loaded) was used as no-drug control for rapamycin-loaded UM formulations. Weights of the painted UM-NHS solution were measured every time.

Figure 12A:
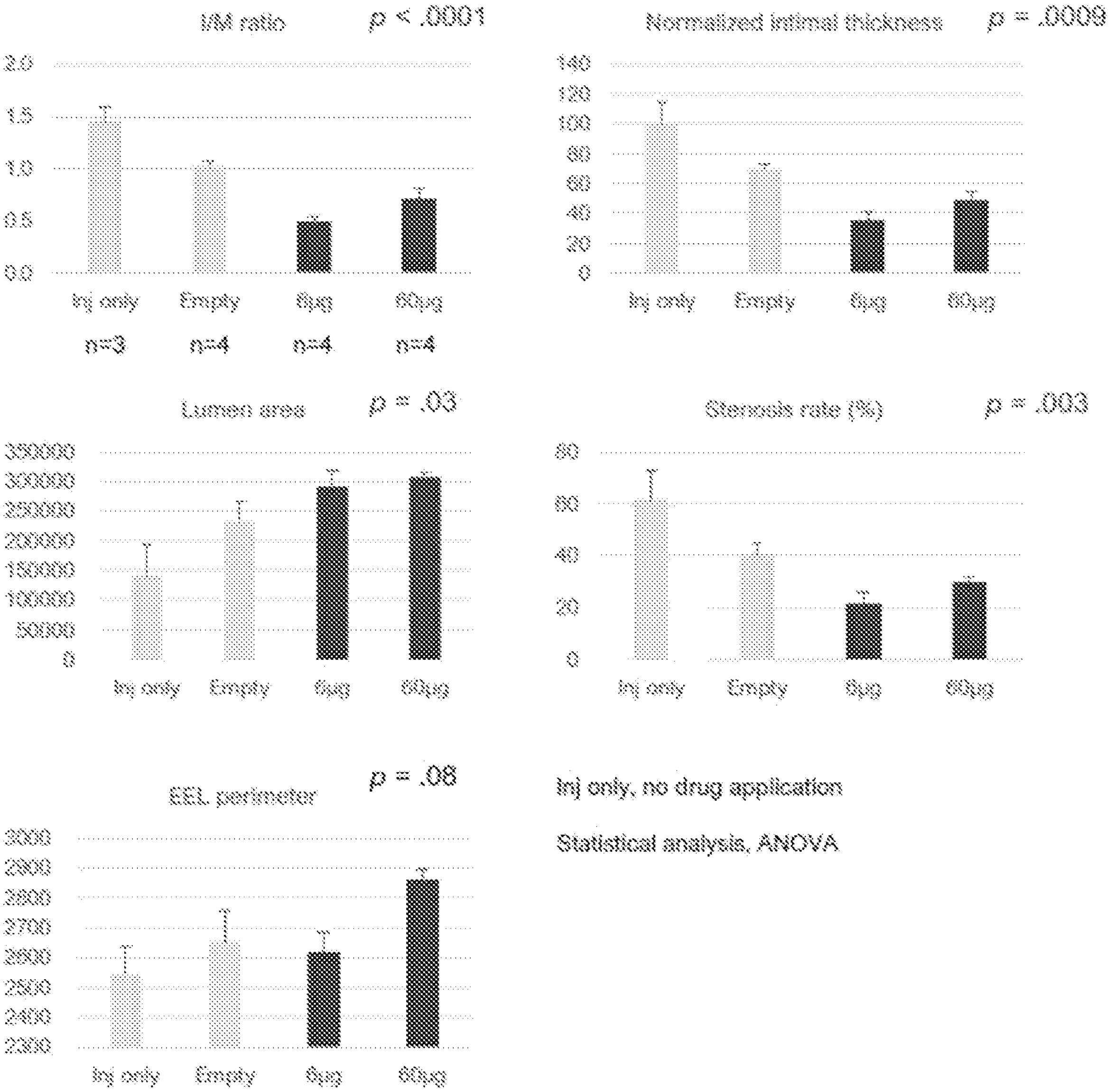
FIGS. 12A-12B show the IH-mitigating effect of painting rapamycin-loaded adventitia-adhesive UM-sulfo-NHS (Mode-4). Open surgery followed by periadventitial application of UM-sulfo-NHS (without or with rapamycin) was performed as described for FIGS. 6A-6D. At post-surgery 14 days arteries were harvested for cross-section preparation and H&E staining.
Figure 12B:
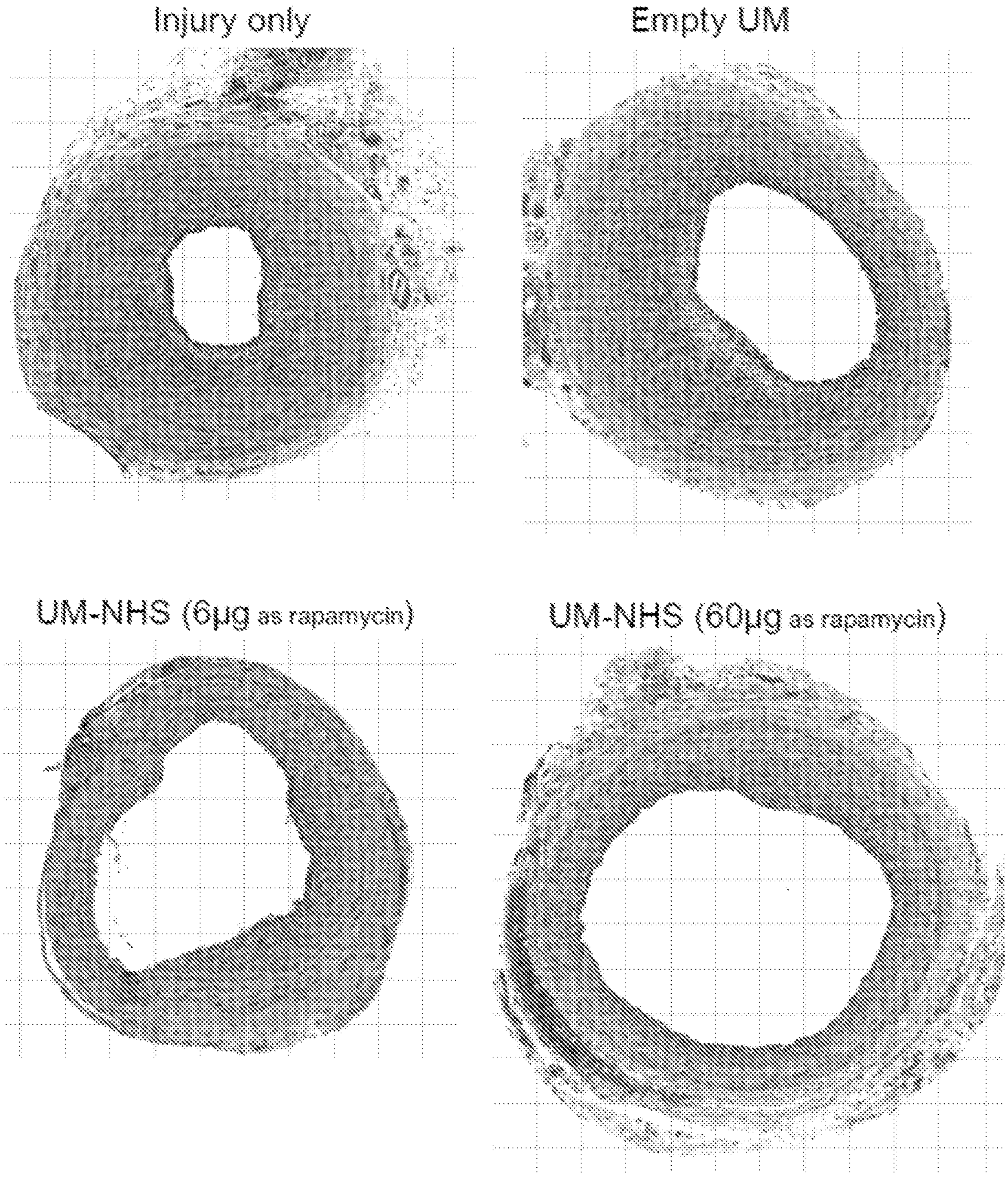
Figure 13A:
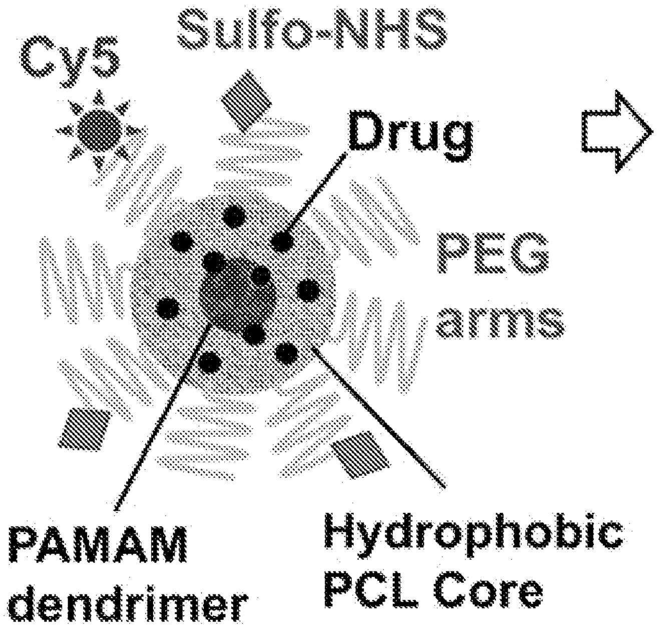
FIGS. 13A-13C show an adhesive nanoparticle (ahNP) structure (FIG. 13A), a carton showing pen-brushing ahNP on the vessel adventitia (FIG. 13B), and a real Cy5 fluorescence image showing adventitial (A) Cy5-ahNP signal and medial (M) elastin autofluorescence (scale bar: 100 μm).
Figures 13B, 13C:
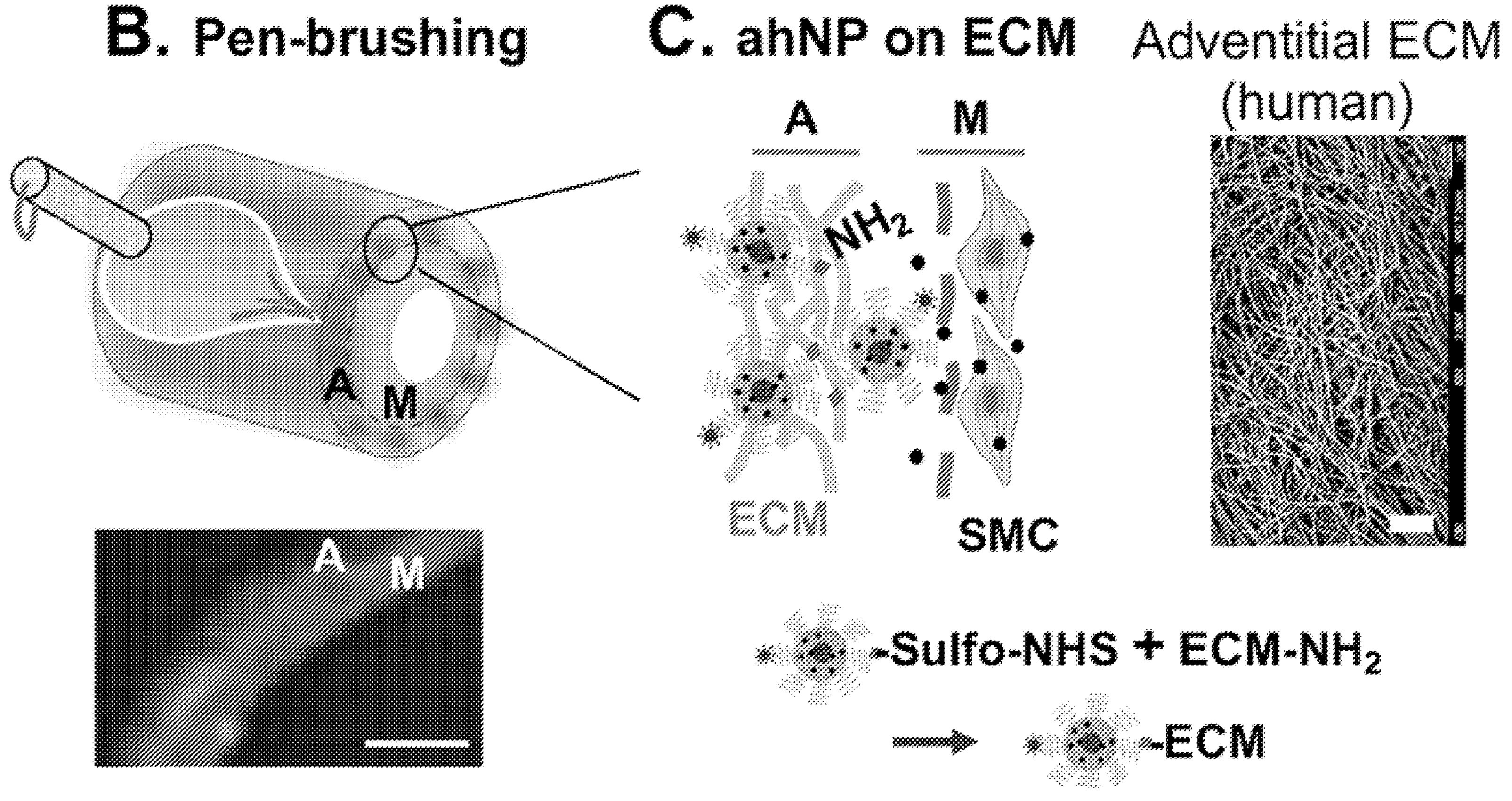
Figures 14A, 14B:
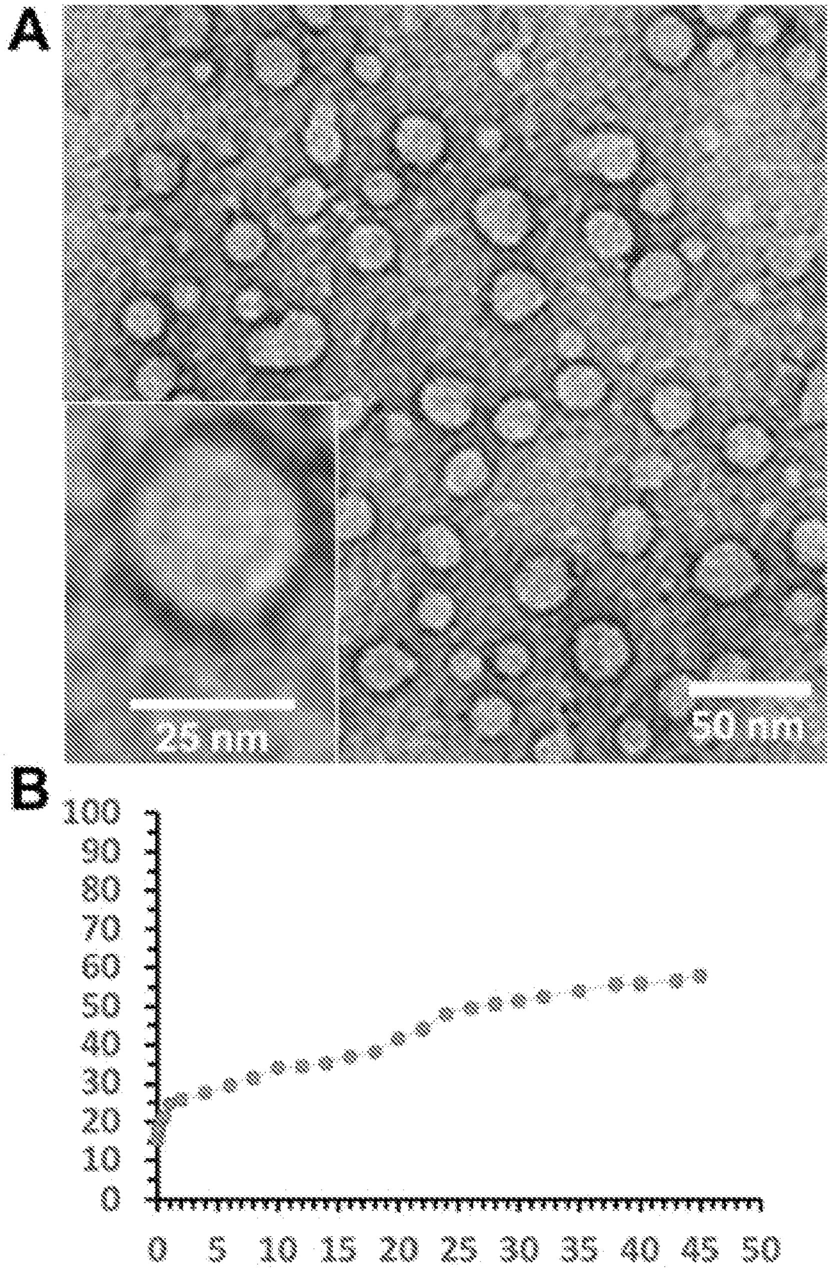
FIG. 14A shows transmission electron microscopy (TEM) image of ahNP. PCL was used in the hydrophobic core.
FIG. 14B shows cumulative release of Pinometostat indicates that ~60% of total drug was released in 45 days.

Similar experiments were performed for UM-sulfo-NHS. Since sulfo-NHS (the sulfonate sodium salt of NHS) is highly soluble but not membrane permeable, as a byproduct of UM adhesion to the artery it can be easily removed with gauze so there are no concerns of tissue toxicity. Results of these experiments can be seen in FIGS. 12A-12B.

Morphometric Analysis of IH

One rat in treated group with empty UM-NHS group was excluded due to thrombotic occlusion. At 14 days after balloon injury, CCAs were collected. Each CCA embedded in paraffin was cut into 3 segments: proximal, middle, and distal. At least 4 sections (each 5 μm thick) representing different locations were cut from these segments for morphometric analysis. The sections included two from the proximal and distal ends of CCA and the other two from the ends of the middle segment. These specimens were processed for hematoxylin-eosin and Masson's trichrome staining. Morphometric analysis was conducted using Image J software (NIH, Bethesda, MD, USA). Lumen area, area inside internal elastic lamina (IEL), area inside the outer boundary of adventitia together with lumen and IEL perimeters were determined. Calculations were conducted as follows; intimal area=IEL area—lumen area; standardized intimal thickness, intima area/IEL perimeter; stenosis rate, (intima area/IEL area)×100; intima/media ratio (I/M ratio), intima area/(area inside adventitia—IEL area). The values from 4-6 CCA sections were averaged to produce a mean for each animal, and the means from all animals in each group were averaged again to calculate mean±SEM (standard error of mean). To observe the localization of Cy5-labelled UM, snap frozen samples were used, and examined under fluorescent microscope.

Quantification of Collagen Density in the Artery

Four to six cross-sections cut from different locations (see detailed description above) from the balloon-injured CCA per each animal were used for Masson's trichrome staining. The color images were transformed into monochrome images at an 8-bit scale using Image J. After adjusting the threshold consistent through the analysis, integrated density of interest was measured. Data values from 6 sections were averaged for each animal, and averages from total animals in a group were used to calculate mean+SEM and statistical analysis.

Immunohistochemistry Analysis of Tissue Toxicity

Paraffin-embedded specimens were processed into 5-µm thick sections for immunostaining. The slides were deparaffinized and hydrated through series of xylenes and graded alcohol. Antigens were retrieved using citrate buffer for 2 hours at 80° C. in a high-pressure cooker. Endogenous peroxidase was blocked by incubation with 3% $H_2O_2$ for 10 min. Following application of a monoclonal antibody against either cleaved Caspase 3 (9661, Cell Signaling Technology, Inc., Danvers, MA) or CD68 (T-3003, BMA Biomedicls, Augst, Switzerland), ImmPRESS HRP Anti-Rabbit IgG (Peroxidase) Polymer Detection Kit (MP-7451, Vector Laboratories Inc., Burlingame, CA) was used as the secondary antibody. The staining intensity was visualized using ImmPACT DAB Peroxidase (HRP) Substrate (SK-4105, Vector Laboratories). Data values from 6 different portions were averaged for each animal, and averages from total animals in a group were used to calculate mean+SEM and statistical analysis.

Statistical Analysis

Data sets were subjected to normality check using Shapiro-Wilk test. Student's t-test was used for two group comparison; one-way analysis of variance (ANOVA) was performed for multiple group comparison followed by post hoc test (specified in figure legends). All data are presented as mean±standard error of the mean (SEM). A difference is considered statistically significant when a p value is <0.05.

Results

Preparation and Characterization of UM-NHS

Figure 2A:
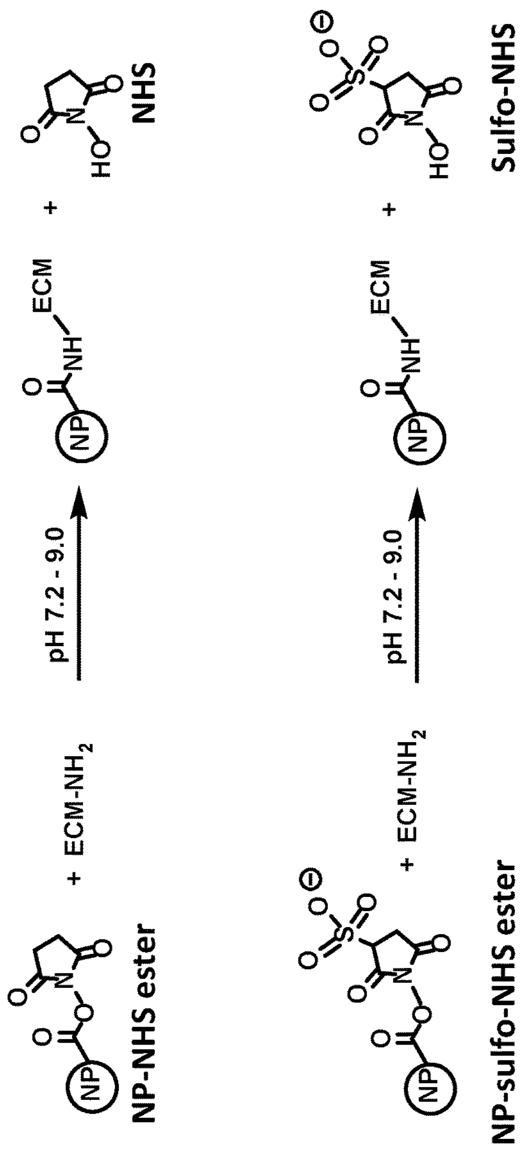
FIG. 2A shows the reaction between NHS ester and amine under basic condition to generate a stable product with amide bond (top), where $R_1$ can be an adhesive nanoparticle or unimolecular micelle as disclosed herein and $R_2$ is an amine group in, for example, vascular tissue; the same reaction chemistry is possible with sulfo-NHS ester and is shown in the bottom of FIG. 2A (where "NP" refers to the nanoparticle).
Figure 2B:
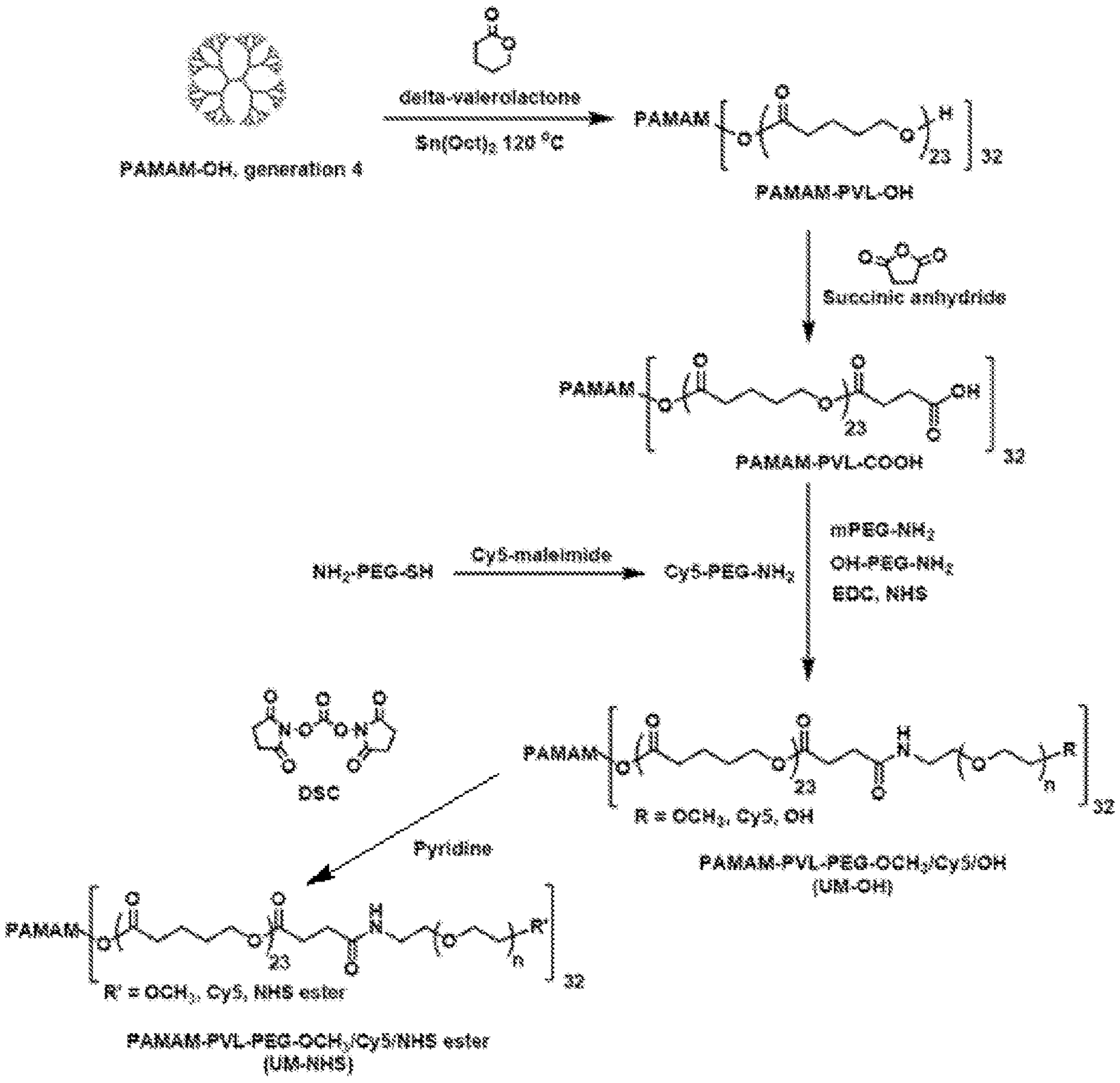
FIG. 2B shows the synthetic procedure to yield PAMAM-PVL-PEG-NHS (UM-NHS) that can be used to react with amine on the vascular outer surface.
Figure 8A:
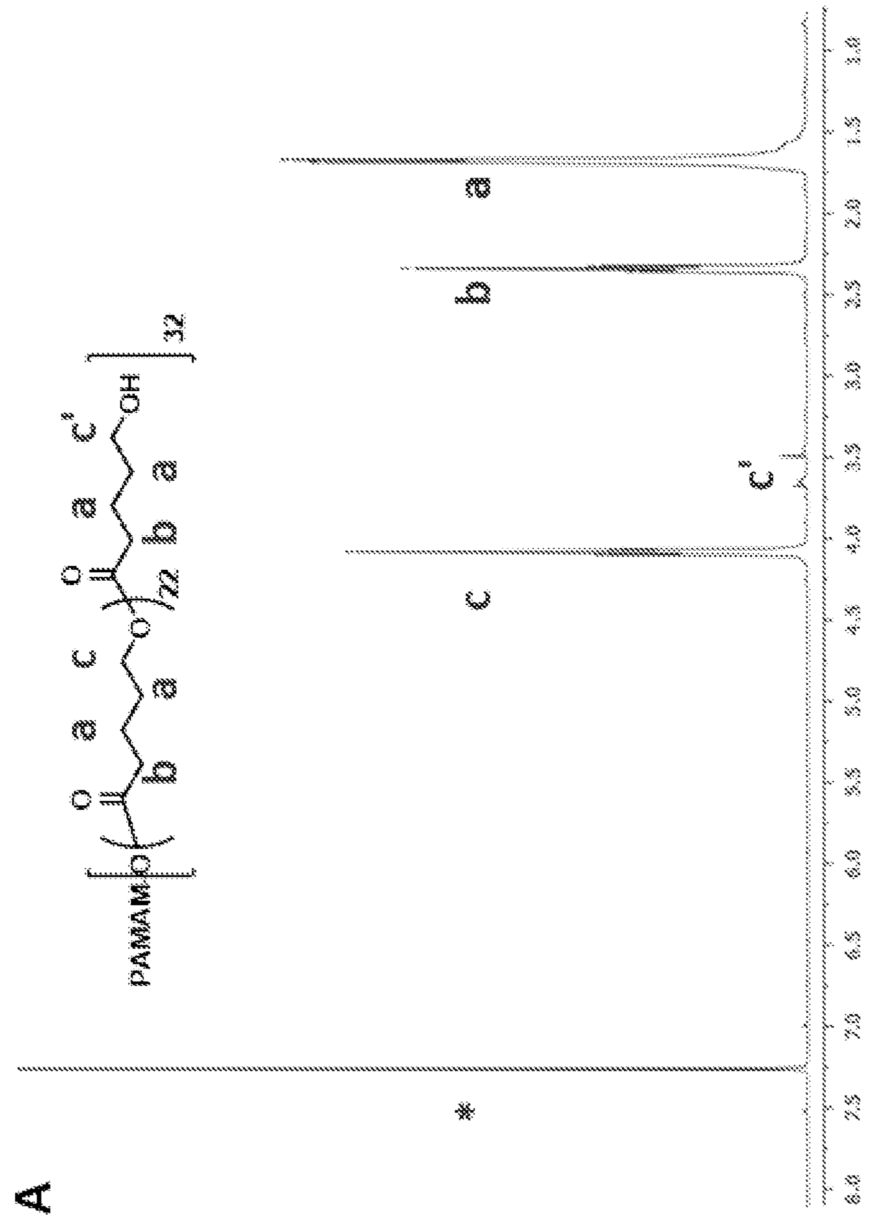
FIGS. 8A-8D show $^1$H NMR analysis of FIG. 8A: PAMAM-PVL-OH ($CDCl_3$, δ 4.08, 3.65, 2.34, and 1.67 ppm).
Figure 8B:
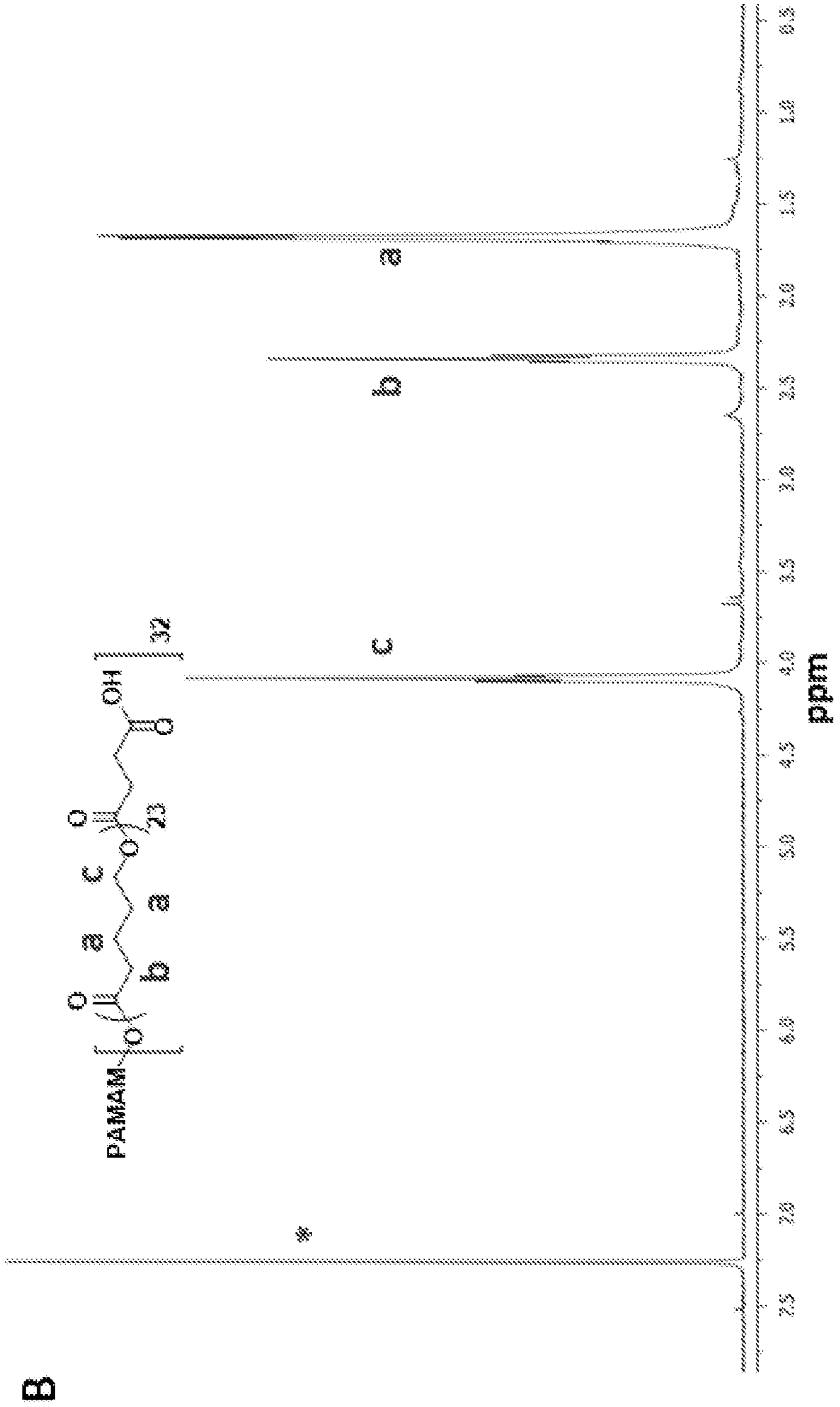
Figure 8C:
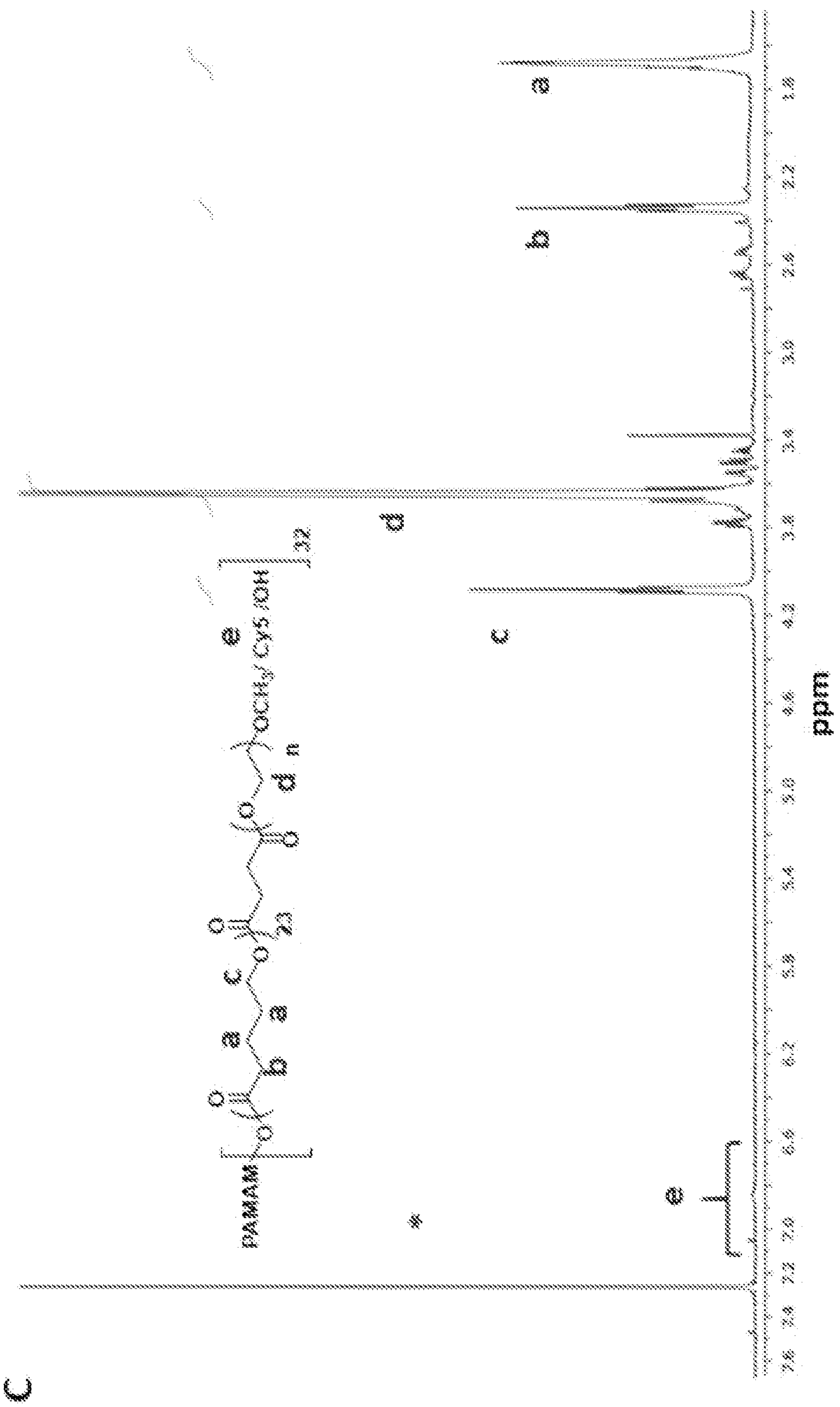
Figure 8D:
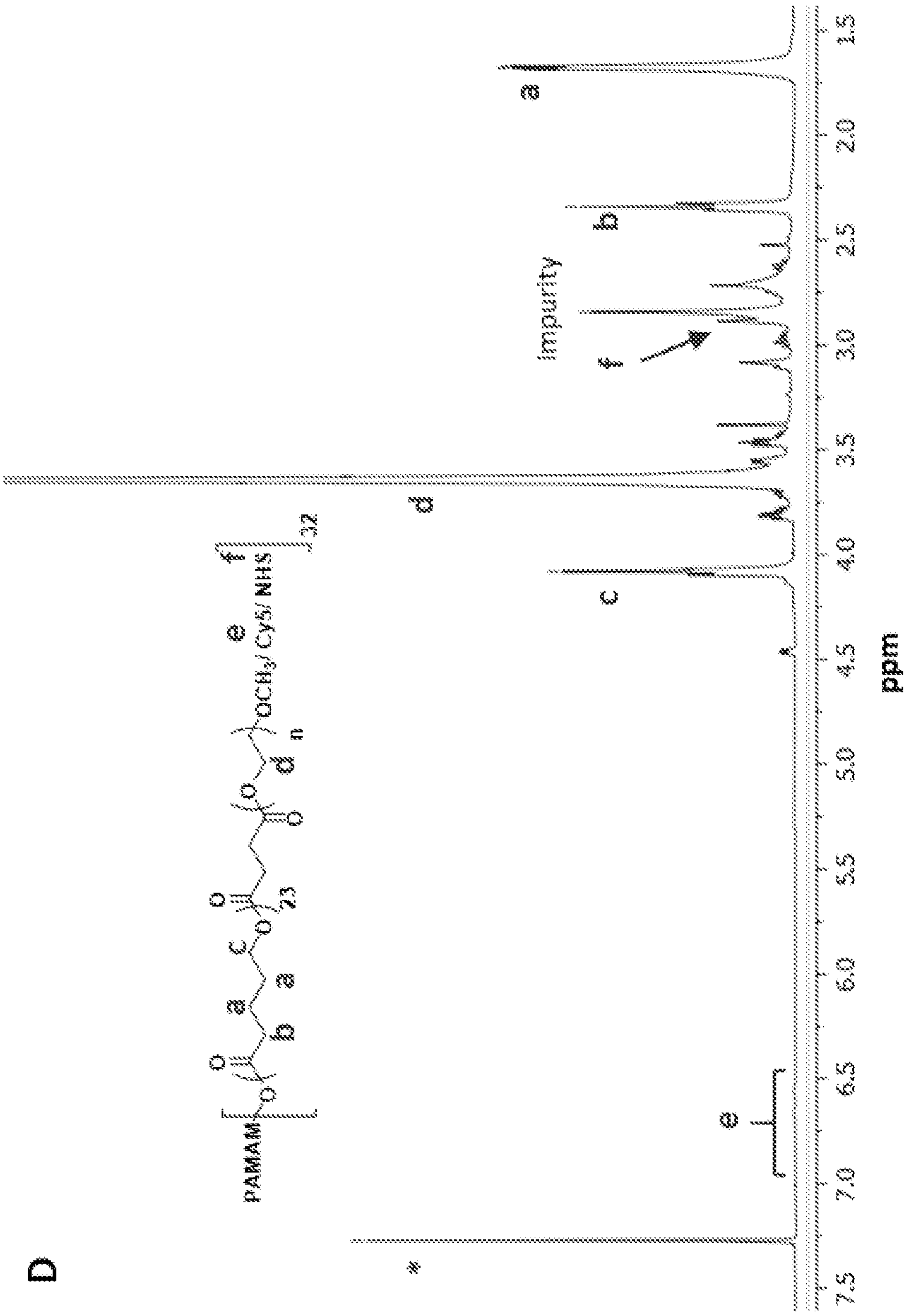
Figures 9A, 9B:
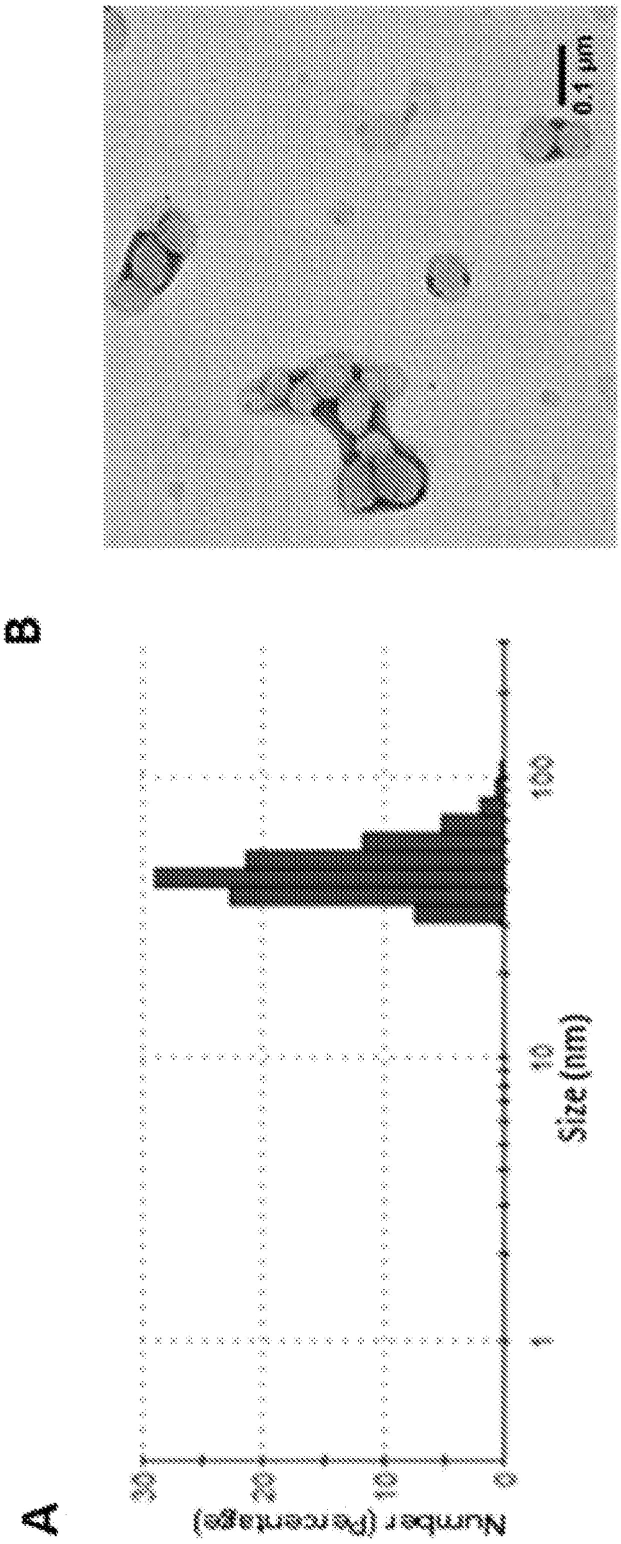
FIGS. 9A-9E show characterizations of UM-NHS.
Figure 9C:
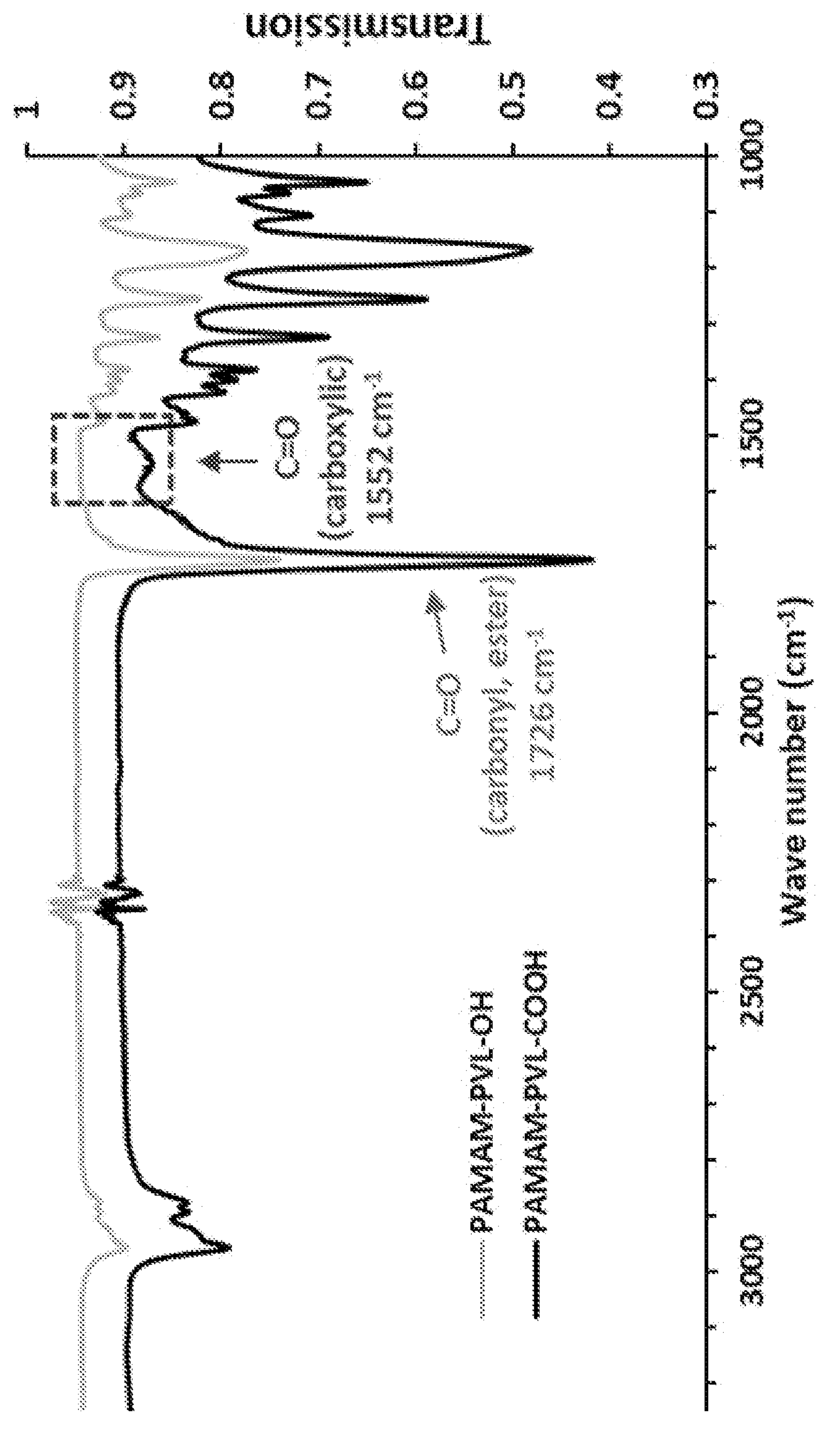
Figure 9D:
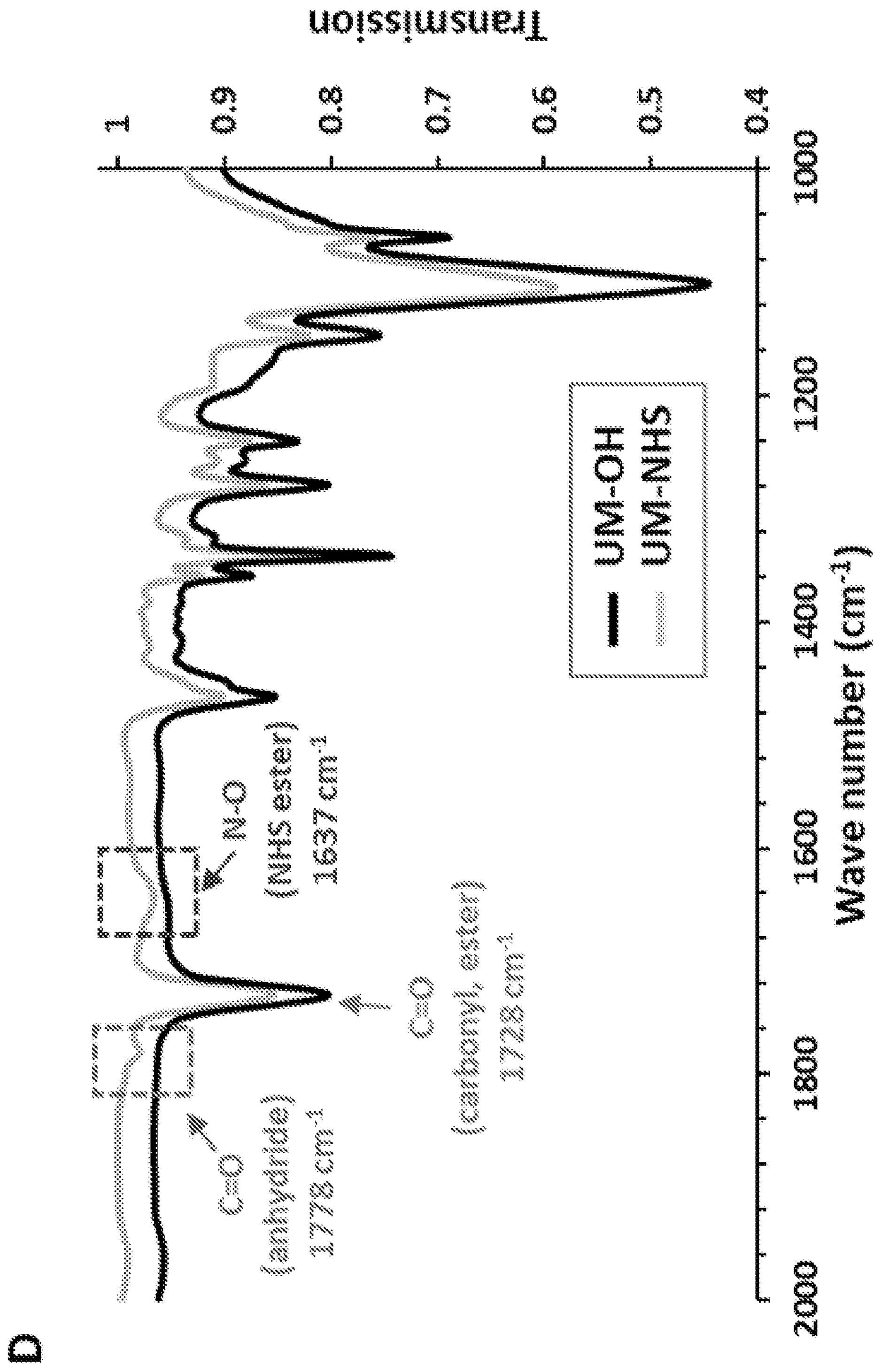

PAMAM-PVL-OH was prepared via ring-opening polymerization as described previously, and then reacted with succinic anhydride under basic pH to yield PAMAM-PVL-COOH. The $^1$H NMR spectra of both products showed characteristic peaks at δ 4.08, 2.34, and 1.67 ppm, assigned to the methylene protons in PVL, and at 3.65 ppm as terminal methylene protons in PVL (FIGS. 8A-8B) as previously reported. Additionally, the average number of repeating units of the PVL was calculated to be 23, based on the area ratio of the peaks at (c) 4.08 ppm and (c') 3.65 ppm (FIG. 8A). The hydrodynamic diameters of PAMAM-PVL-OH and PAMAM-PVL-COOH were 23.0±2.4 and 24.6±3.4 nm, respectively. However, the zeta potential of PAMAM-PVL-OH was almost neutral (1.28±1.01 mV) while that of PAMAM-PVL-COOH was negative (−22.97±0.99 mV), which can be attributed to the carboxyl terminal groups (Table 1). Furthermore, FTIR spectra of PAMAM-PVL-OH and PAMAM-PVL-COOH were studied. C═O stretching of carbonyl (1726 cm$^{-1}$) was found in both compounds due to PVL segments while anti-symmetric C═O stretching of carboxyl (1552 cm$^{-1}$) was only observed in PAMAM-PVL-COOH (FIG. 9C). Next, PAMAM-PVL-COOH was activated by EDC-NHS, followed by PEGylation with amine-PEG-$OCH_3$/Cy5/OH to produce PAMAM-PVL-PEG-$OCH_3$/Cy5/OH (UM-OH). Then, hydroxy at the terminal of UM-OH was reacted with the carbonyl group in DSC to generate PAMAM-PVL-PEG-$OCH_3$/Cy5/NHS (UM-NHS) under basic condition (FIGS. 2A-2B). It was found that the hydrodynamic diameter of UM-NHS was about 65.66±5.73 nm, and the zeta potential became neutral (~1.50±0.84 mV) (Table 1, FIG. 9A). Additionally, the diameter of the spherical UM-NHS nanoparticle measured by TEM was around 63 nm (FIG. 9B). The chemical structures of UM-OH and UM-NHS were characterized by $^1$H NMR. The peaks at 6-6.5-7.0 and 3.64 ppm indicated the conjugation of Cy5 and PEG, respectively (FIGS. 8C-8D). The NMR characteristic peak of NHS ester was shown at δ 2.84 ppm in UM-NHS. Additionally, FTIR was used to confirm the presence of NHS, which was found at 1637 cm$^{-1}$ (N—O stretching) and 1778 cm$^{-1}$ (C═O stretching; anhydride) from UM-NHS, but not in the UM-OH (FIG. 8D).

TABLE 1

Sizes and Surface Charges of PAMAM-PVL-OH, PAMAM-PVL-COOH, and UM-NHS via DLS

| Samples | Size (µm) | PDI | Zeta potential (mV) |
|---|---|---|---|
| PAMAM-PVL-OH | 23.02 ± 2.39 | 0.201 | 1.28 ± 1.01 |
| PAMAM-PVL-COOH | 24.61 ± 3.38 | 0.29 | −22.97 ± 0.99 |
| UM-NHS | 65.66 ± 5.73 | 0.226 | 1.50 ± 0.84 |

Rapamycin Release Profiles from UM-NHS In Vitro

Figure 9E:
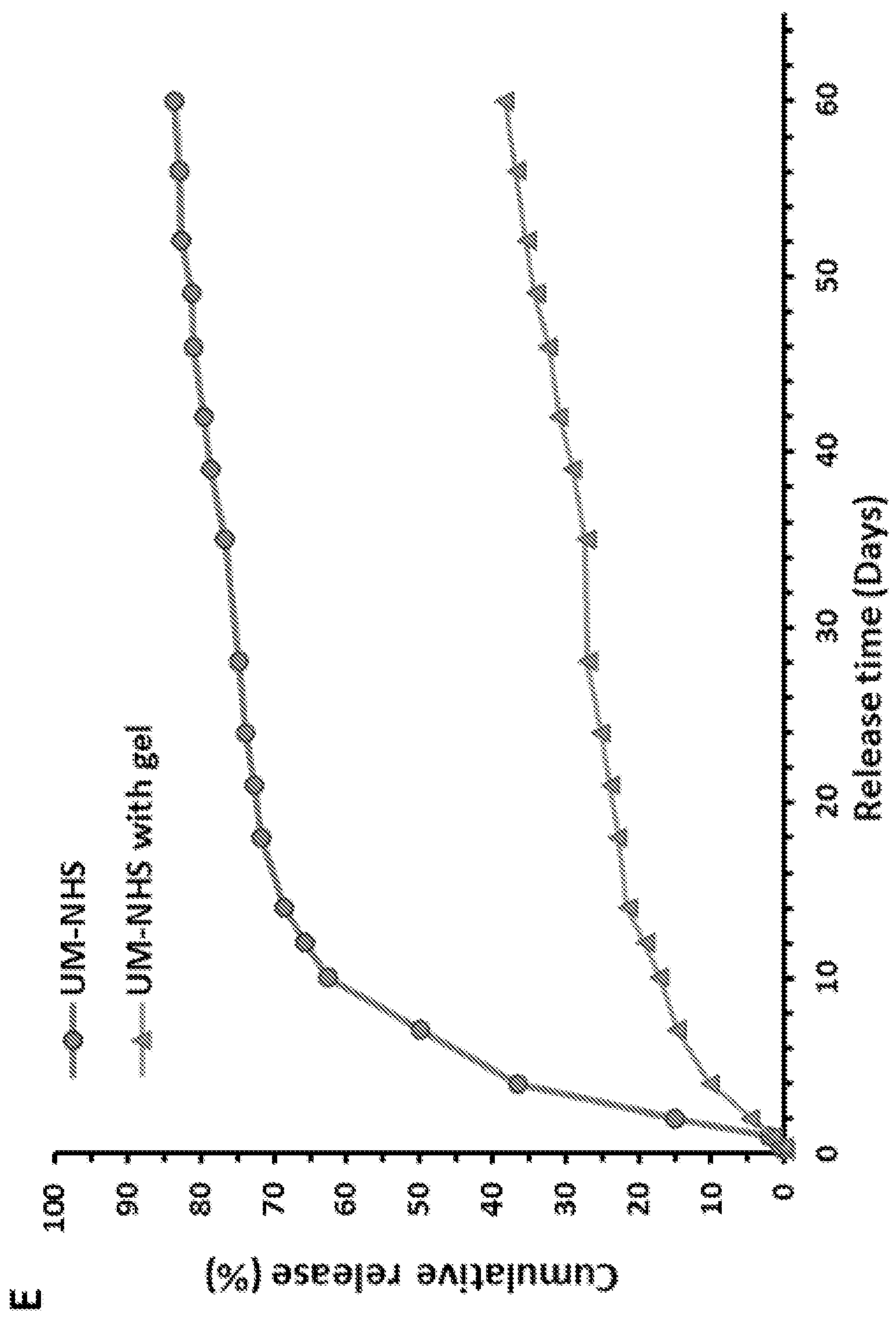

The rapamycin content loaded in UM-NHS was found at 20.3 wt %, as measured by HPLC following the reported method. FIG. 9E shows two release profiles, from crosslinked (corresponding to Mode-1) and non-crosslinked UM-NHS (Mode-2 and Mode-3), with 38.3% and 83.6% release at Day 60 from the former and the latter, respectively. The release from the former was retarded probably due to a drug-trapping effect of the crosslinked network, in an analogy to the UM encapsulated in a hydrogel.

Periadventitial Drug Delivery Using Crosslinked and Non-Crosslinked UM-NHS for IH Mitigation To evaluate the utility of tissue-adhesive UM for periadventitial local drug delivery, the well-established model of rat carotid artery balloon angioplasty that robustly induces IH was used. Upon surgery, the rat neck needs to be opened through an incision in order to dissect out the carotid arteries. As such, this model resembles open vascular surgery, and hence meets the stated purpose of testing perivascular application of the UM formulations for their IH-mitigating efficacy. Rapamycin was used as an IH-inhibitory model drug, which is established in both preclinical and clinical settings.

To eliminate a hydrogel that was used in previous studies to sequester nanoparticles in the periadventitial space, UM-NHS was first crosslinked into a network to retain a high drug-loading capacity (Mode-1). For comparison, an equal amount of UM-NHS (non-crosslinked) was used, which remained as a UM nanoparticle liquid solution during the periadventitial application (Mode-2). To ensure sufficient conjugation of UM-NHS with the $NH_2$ group on the adventitial matrix proteins, the balloon-injured carotid artery was soaked (incubated) in UM-NHS (crosslinked in Mode-1; non-crosslinked in Mode-2) for 15 min, in a reservoir formed around the artery with a Parafilm membrane. In each mode, the empty UM formulations (no drug) were used as a control against the rapamycin-loaded UM. At 14 days post-surgery, animals were euthanized for morphometric analysis of IH and tissue toxicity evaluations through immunohistochemistry.

Figures 3A, 3B:
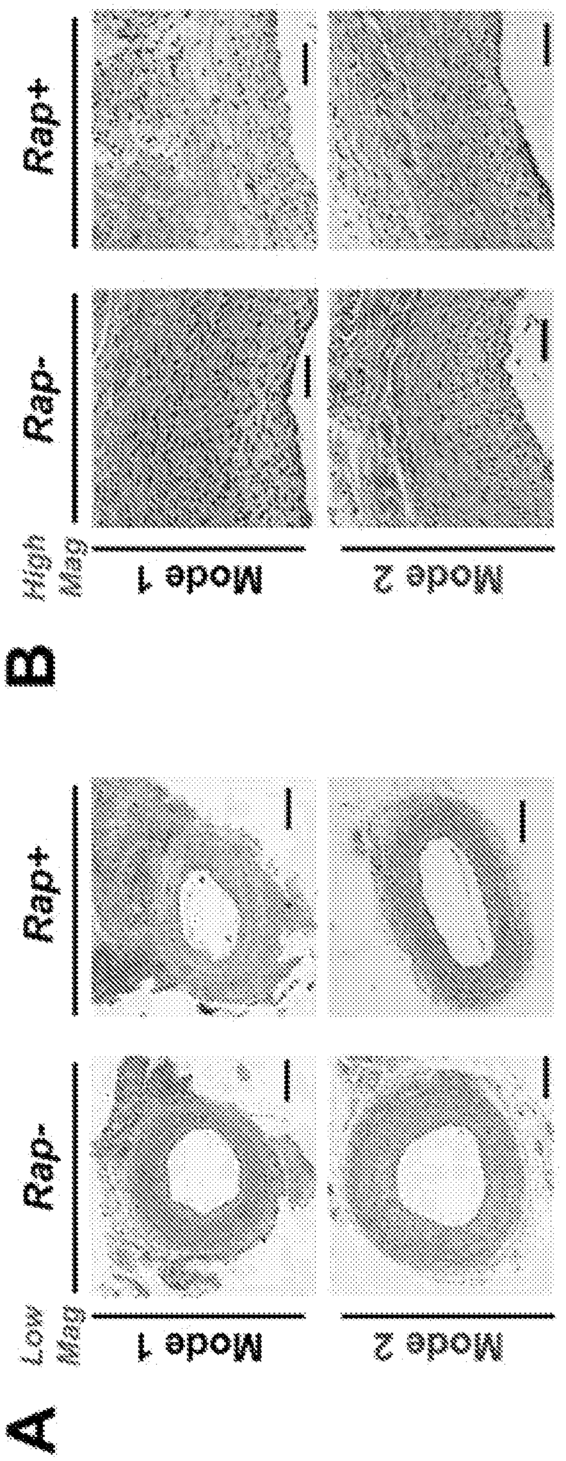
FIGS. 3A-3C show the IH-mitigating effect of rapamycin periadventitially delivered through crosslinked (Mode-1) or non-crosslinked UM (Mode-2). The open surgery of rat common carotid artery angioplasty followed by periadventitial application of UM (without or with rapamycin) is described in the Examples. At post-surgery 14 days arteries were harvested for cross-section preparation and H&E staining.
Figure 3C:
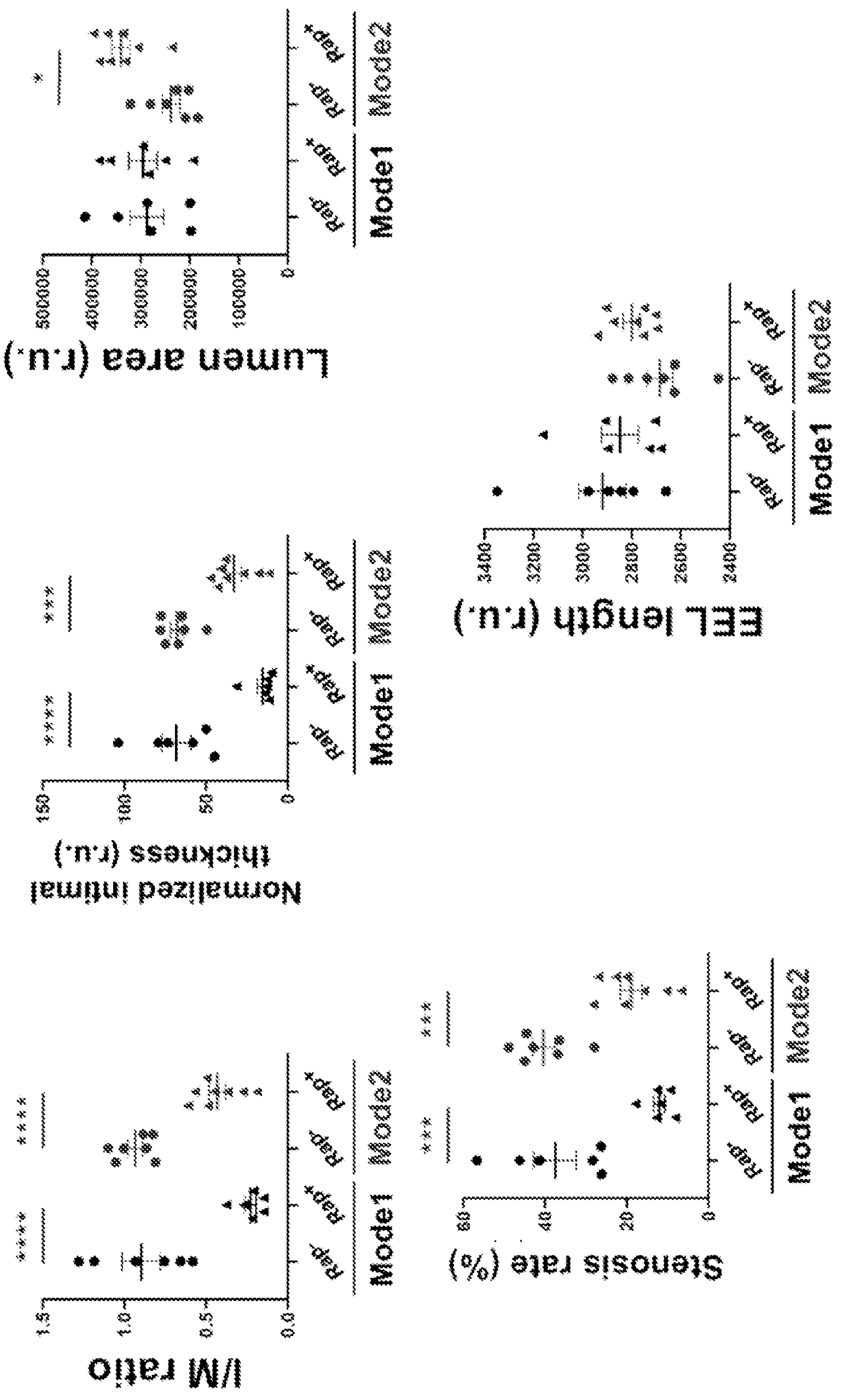

To measure IH, the intima versus media area ratio (I/M) was primarily used. The intima area was also normalized to IEL length, termed as normalized intima thickness (NIT), taking advantage of the fact that IEL length, unlike IEL area, is not subject to the variability caused by morphological deformation of the artery cross sections. Moreover, stenosis rate was also calculated (FIGS. 3A-3C). These three parameters were used to evaluate IH. In Mode-1, the I/M ratio, NIT, and stenosis rate were significantly reduced (with vs without rapamycin) by 74.6% (from 0.90±0.12 to 0.23±0.03), 77.4% (from 68.3±8.9 to 15.4±3.3), and 67.9% (from 37.5±5.2% to 12.0±1.4%), respectively, yet the lumen area did not change. In Mode-2, IH was also inhibited by the rapamycin-loaded UM (vs no drug). The I/M ratio, NIT, and stenosis rate significantly decreased (with vs without drug) by 53.8% (from 0.94±0.04 to 0.43±0.05), 51.3% (from 67.9±3.8 to 33.1±4.5), and 53.1% (from 40.4±2.7% to 18.9±2.7%), respectively. The lumen area increased significantly by 42.9% (from 238465±18301 to 340728±18192). Since the stenosis rate is also subject to change of overall vessel size, it was assessed by measuring the length of external elastic lamina (EEL). Indeed, the EEL length in Mode-1 decreased (no statistical significance), which could account for the lack of increased lumen area even though the neointima was markedly reduced. By contrast, the vessel size in Mode-2 increased albeit without reaching statistical significance. Thus, while IH was mitigated to a greater extent in Mode-1 than in Mode-2, a desired increase of lumen area occurred in Mode-2 but not in Mode-1.

Tissue Toxicity of Crosslinked UM-NHS after Periadventitial Application

Figures 4A, 4B, 4C:
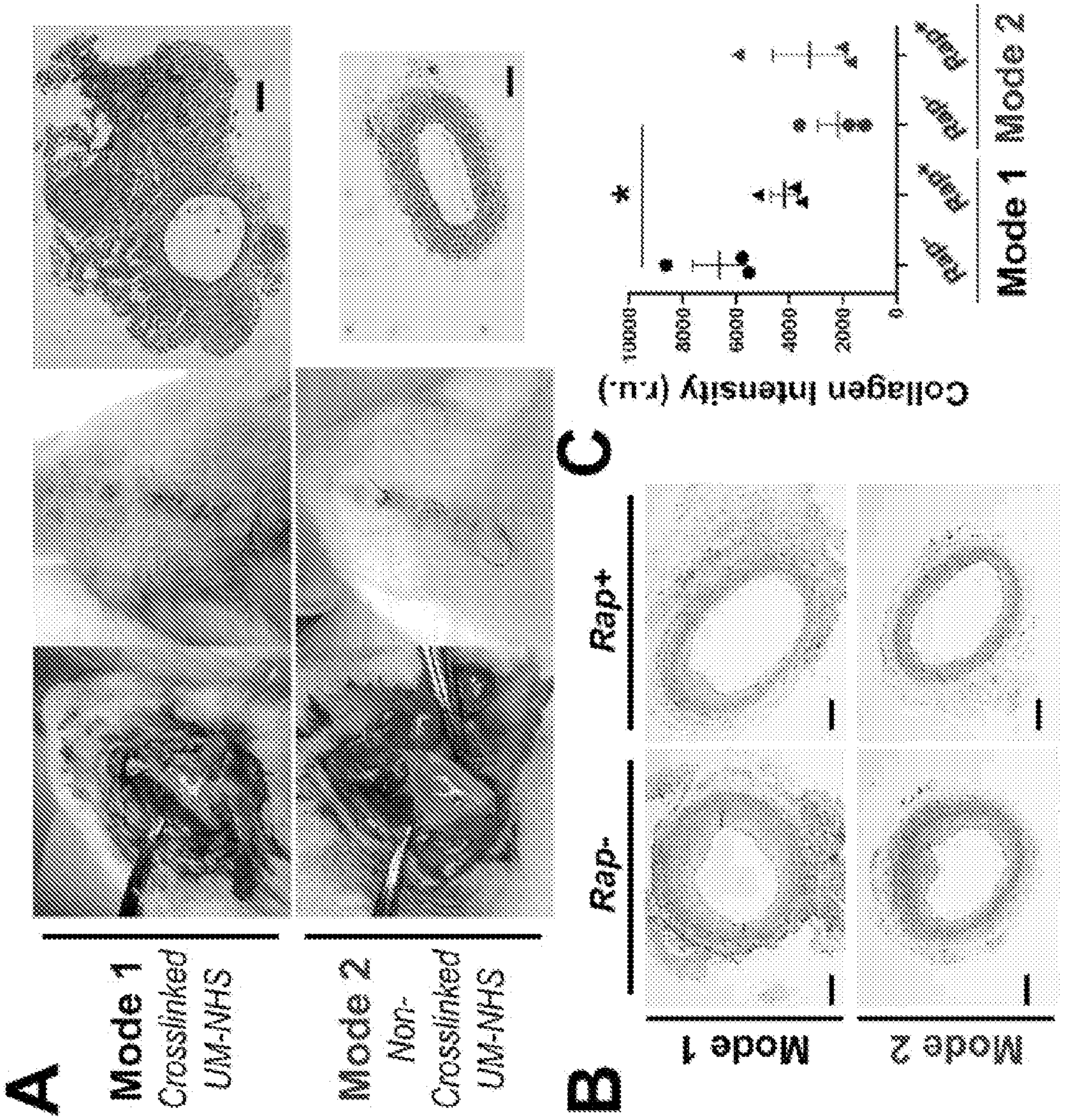
FIGS. 4A-4C show the pro-fibrotic effect of the Mode-1 (vs Mode-2) application on the artery.
Figure 5A:
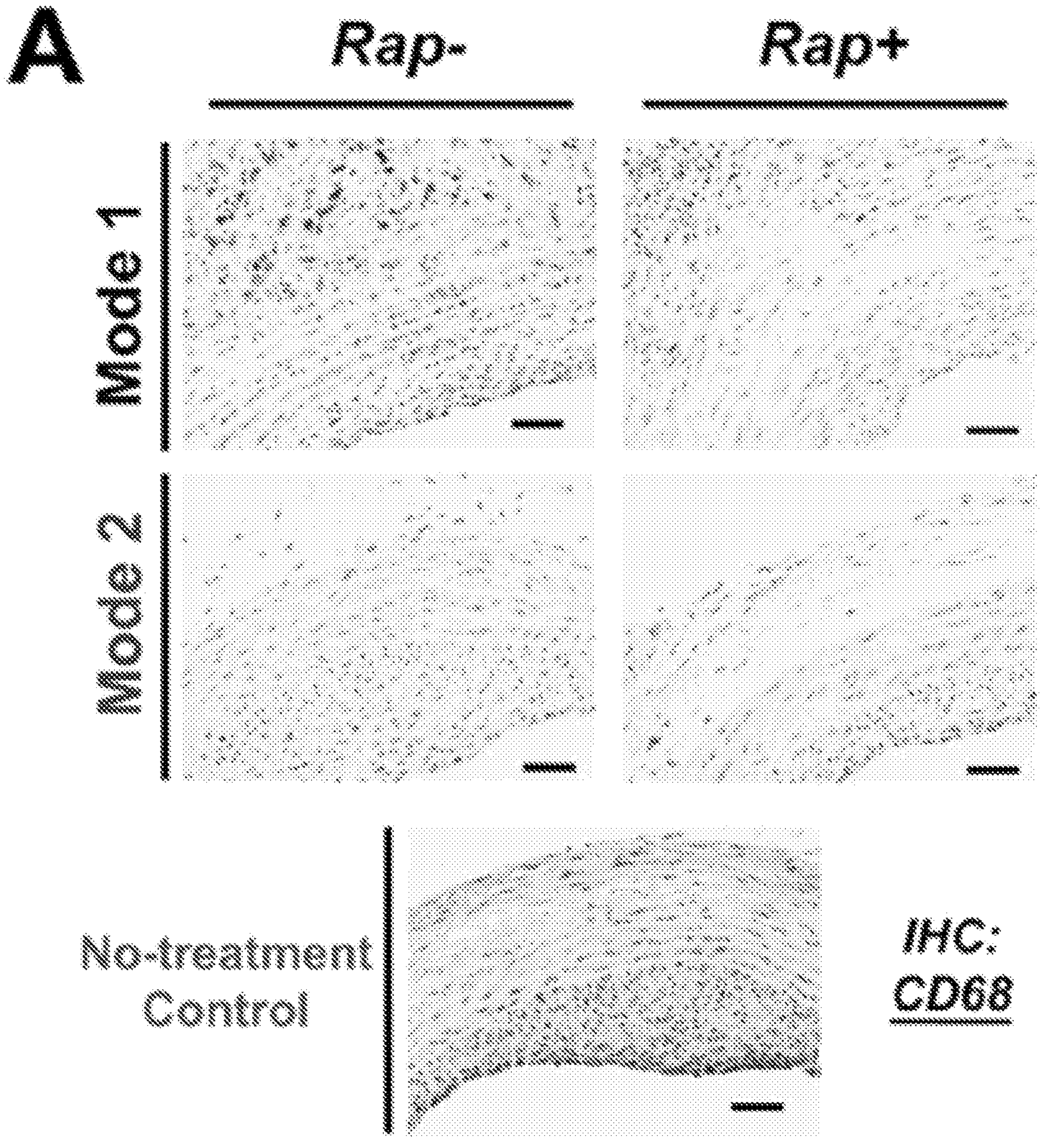
FIGS. 5A-5D show the pro-inflammatory/pro-apoptotic effect of the Mode-1 (vs Mode-2) application on the artery.
Figure 5B:
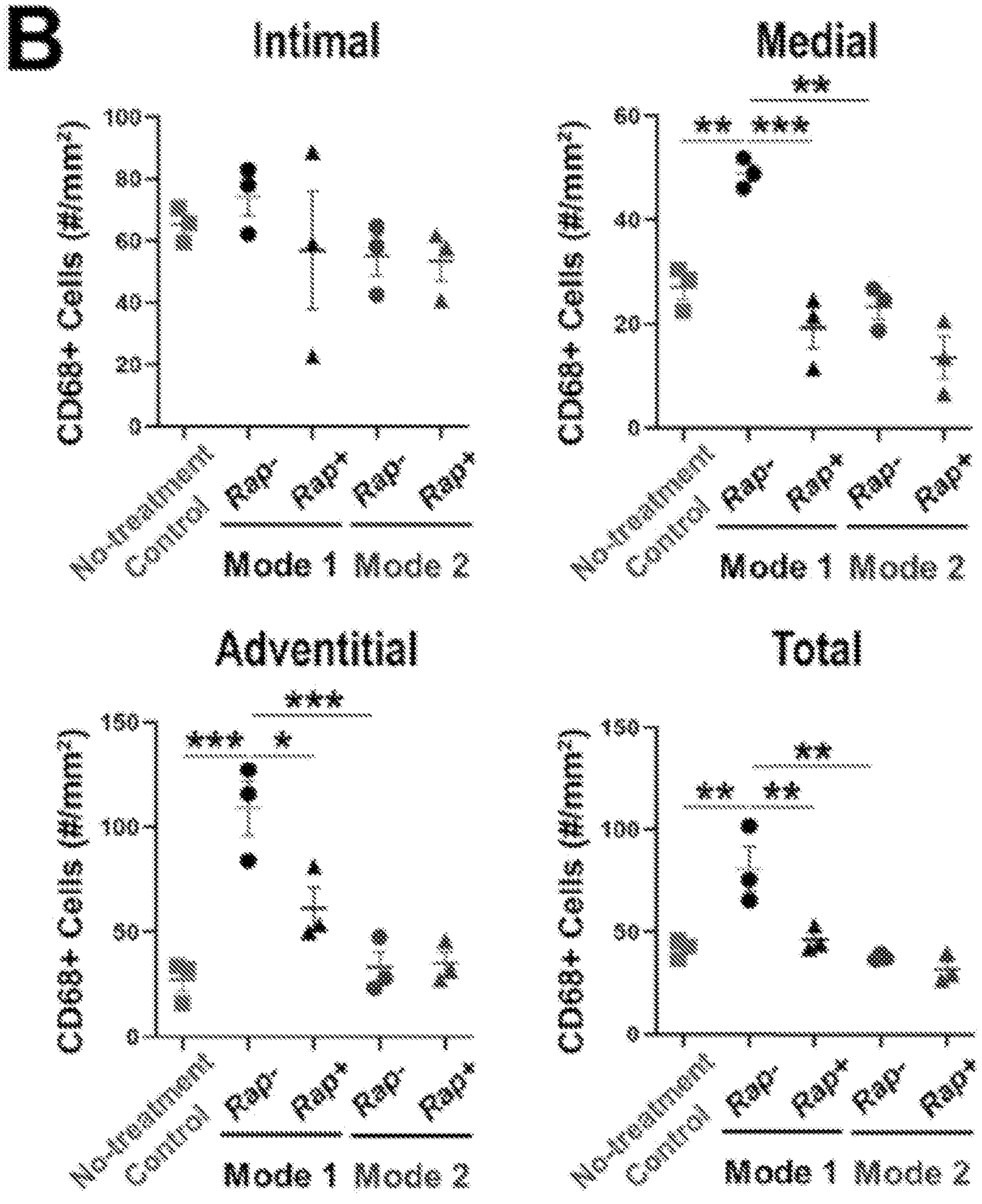
Figure 5C:
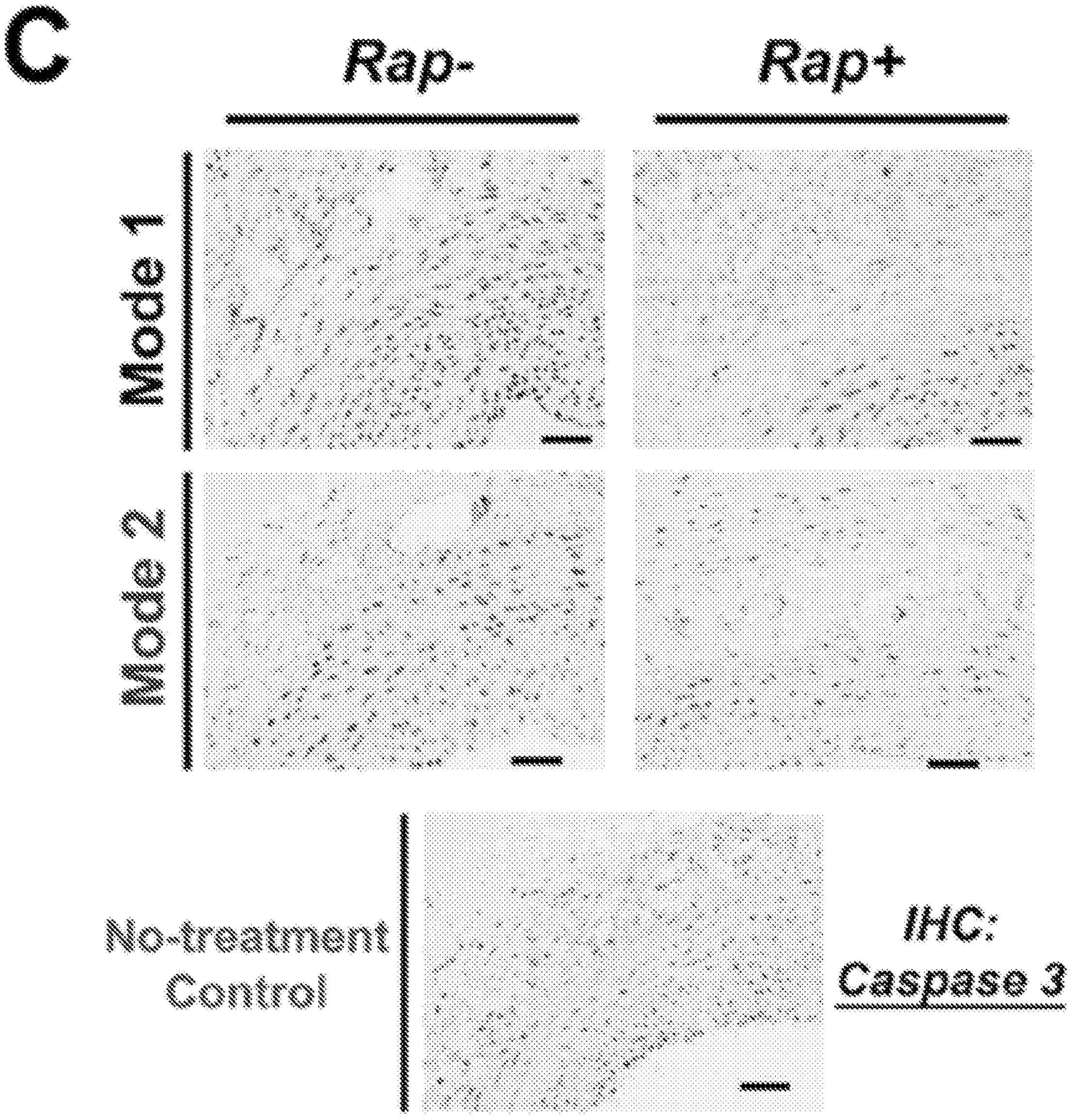
Figure 5D:
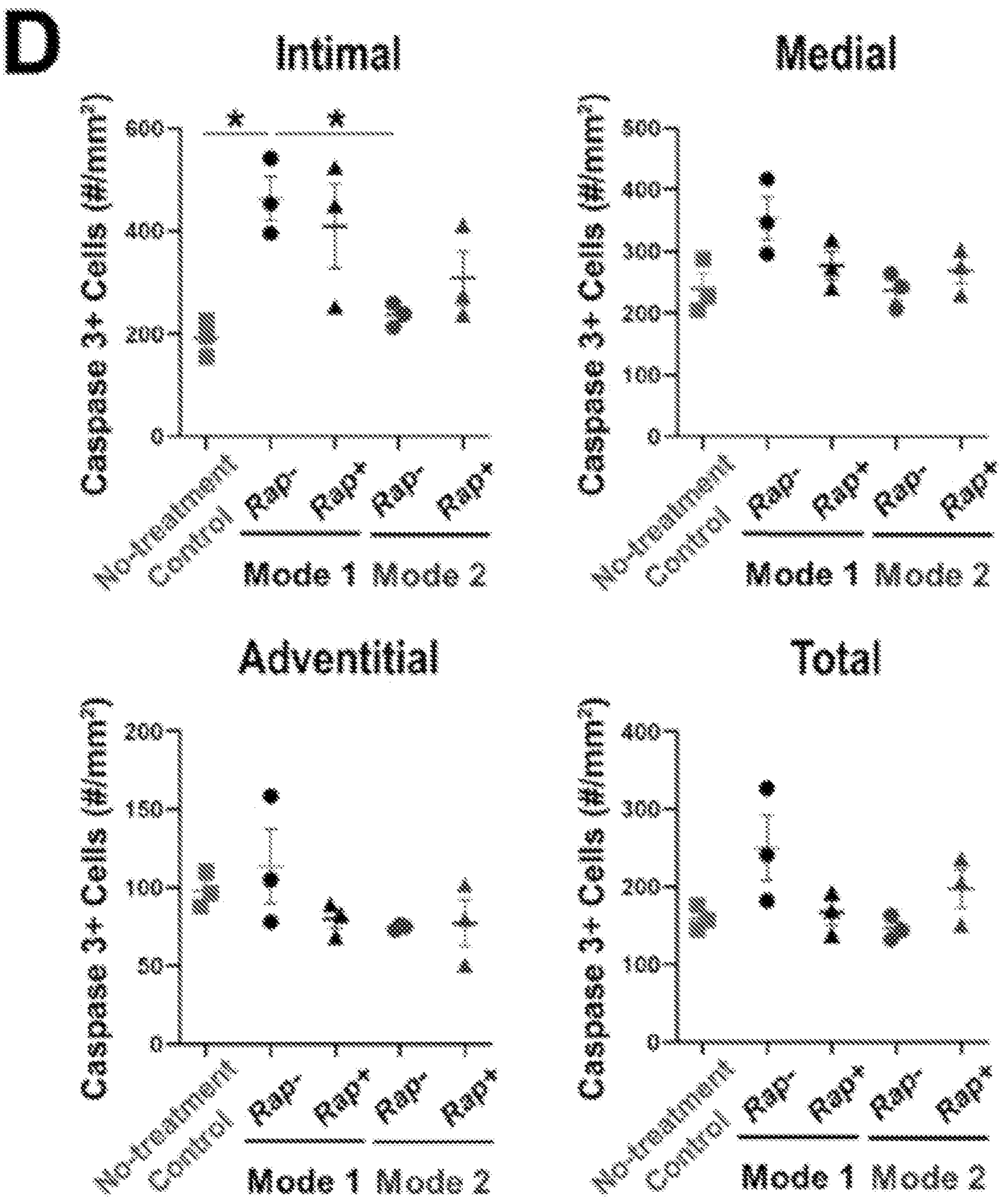

During the experiment, a bulging of the animal neck was noticed in Mode-1 but not in Mode-2 (FIGS. 4A-4C). Upon tissue collection at the end of the Mode-1 experiment, it was observed that the CCAs were buried in scar tissues and hardly dissectible, a problem that did not occur in Mode-2 (Table 2). Consistently, histology showed that the arteries from Mode-1 but not Mode-2 appeared to be tightly connected with surrounding tissues, suggestive of tissue fibrosis (FIG. 4A). Masson's trichrome staining was thus performed to evaluate collagen accumulation in the vessel wall. Indeed, severe fibrosis occurred in Mode-1 in comparison to Mode-2 (the empty UM condition), as indicated by much intensified adventitial collagen accumulation (FIGS. 4B-4C). Rapamycin alleviated this fibrotic severity in Mode-1, a finding consistent with the previously reported anti-fibrotic effect exhibited by rapamycin.

TABLE 2

Gross Evaluation of Tissue Damage at 14 Days after Mode-1 and Mode-2 Applications

| | | Wound Swelling | | Inflammation | Gel Residue |
|---|---|---|---|---|---|
| Mode-1 | Rap-Loaded NP + Gel | ++ | 4 mm | Severe | ++ |
| | | ++ | 5 mm | Severe | ++ |
| | | + | 2 mm | Severe | ++ |
| | Empty-NP + Gel | + | 2 mm | Mod-Severe | ++ |
| | | + | 2 mm | Severe | ++ |
| | | + | 1 mm | Mod-Severe | ++ |
| Mode-2 | Rap-Loaded NHS | – | | Mild | – |
| | | – | | Mild | – |
| | | – | | Mild | – |
| | Empty-NP-NHS | – | | Mild-Mod | – |
| | | – | | Mild | – |
| | | – | | Mild | – |

Considering that tissue fibrosis is often associated with inflammation, macrophage infiltration via immunostaining of the marker CD68 was next determined. In agreement with the above observations, the number of CD68-positive cells of the Model-1 empty UM condition was the highest across all conditions in Mode-1 and Mode-2. While this number was significantly higher above the injury-only background control either in the adventitial or medial layer or when counted in all layers (FIGS. 5A-5D), the difference was abolished by rapamycin in Mode-1. Compared to the Mode-1 empty UM condition, CD68 staining in Mode-2 remained significantly lower. In the neointima layer, no significant difference in CD68 staining was seen across all conditions. The number of cells stained positive for activated (cleaved) caspase-3 was significantly higher in the neointima layer in Mode-1, either compared to no treatment control or Mode-2. In other layers, while there appeared to be more apoptotic cells in the Mode-1 empty UM condition than other conditions, the differences were not significant.

Taken together, the above results indicated that Mode-1 but not Mode-2 produced a significant IH-mitigating therapeutic effect. However, the severe tissue damage imposed by this crosslinked UM drug delivery platform is prohibiting for further translation.

Adventitial Painting of Non-Crosslinked UM-NHS for Effective Non-Toxic Mitigation of IH To create a simple, non-toxic modality for anti-IH periadventitial drug application, further improvement was sought based on Mode-2, which proved to be less toxic than Mode-1. Since the soaking approach requires extra time and materials for preparation and a Parafilm reservoir which nonetheless is subject to spill of the UM-NHS solution, it was replaced with direct painting of non-crosslinked UM-NHS over the artery outer surface. In addition, as the NHS-ester/$NH_2$ reaction is known to occur rapidly and robustly under basic condition, the 15 min incubation step used in the soaking approach was eliminated.

Figures 6A, 6B, 6C:
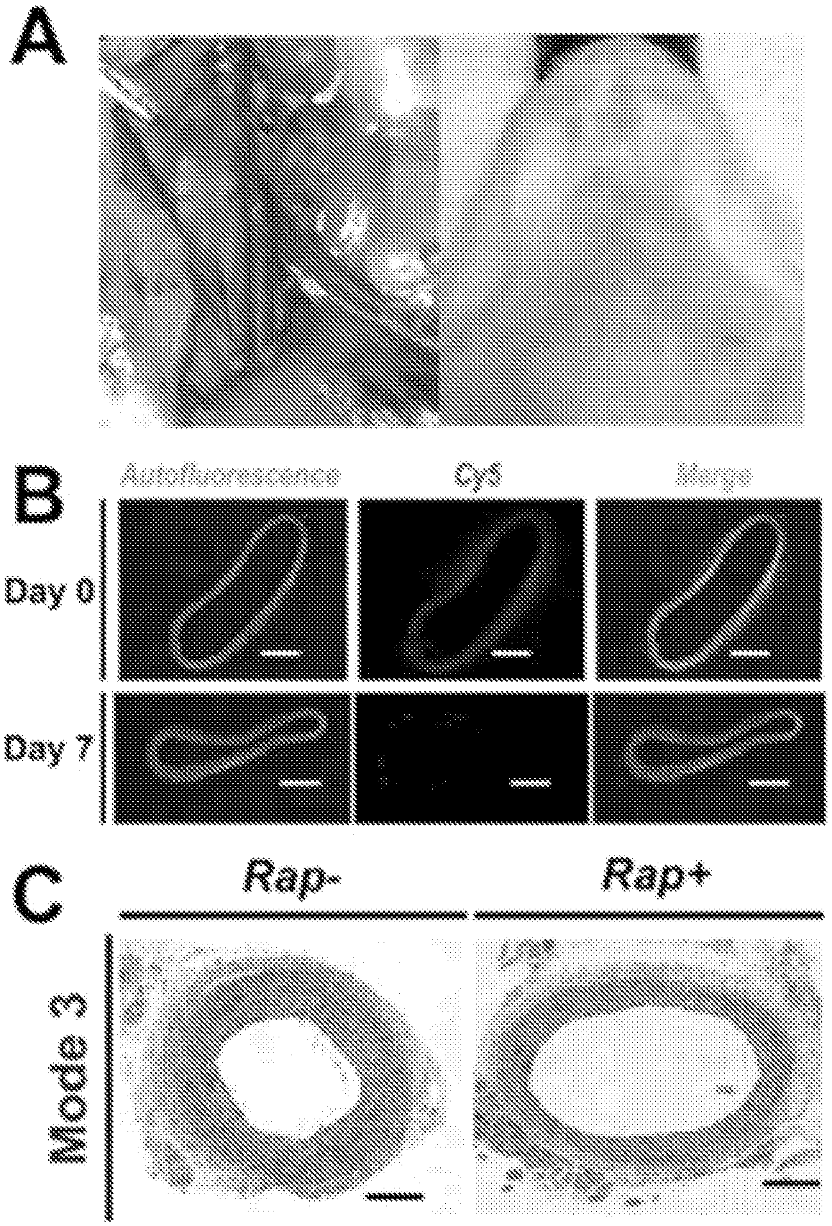
FIGS. 6A-6D show IH-mitigating effect of rapamycin periadventitially delivered using a painting approach (Mode-3). Open surgery followed by periadventitial application of UM-NHS (without or with rapamycin) is described in the Examples. At post-surgery 14 days arteries were harvested for cross-section preparation and H&E staining.
Figure 6D:
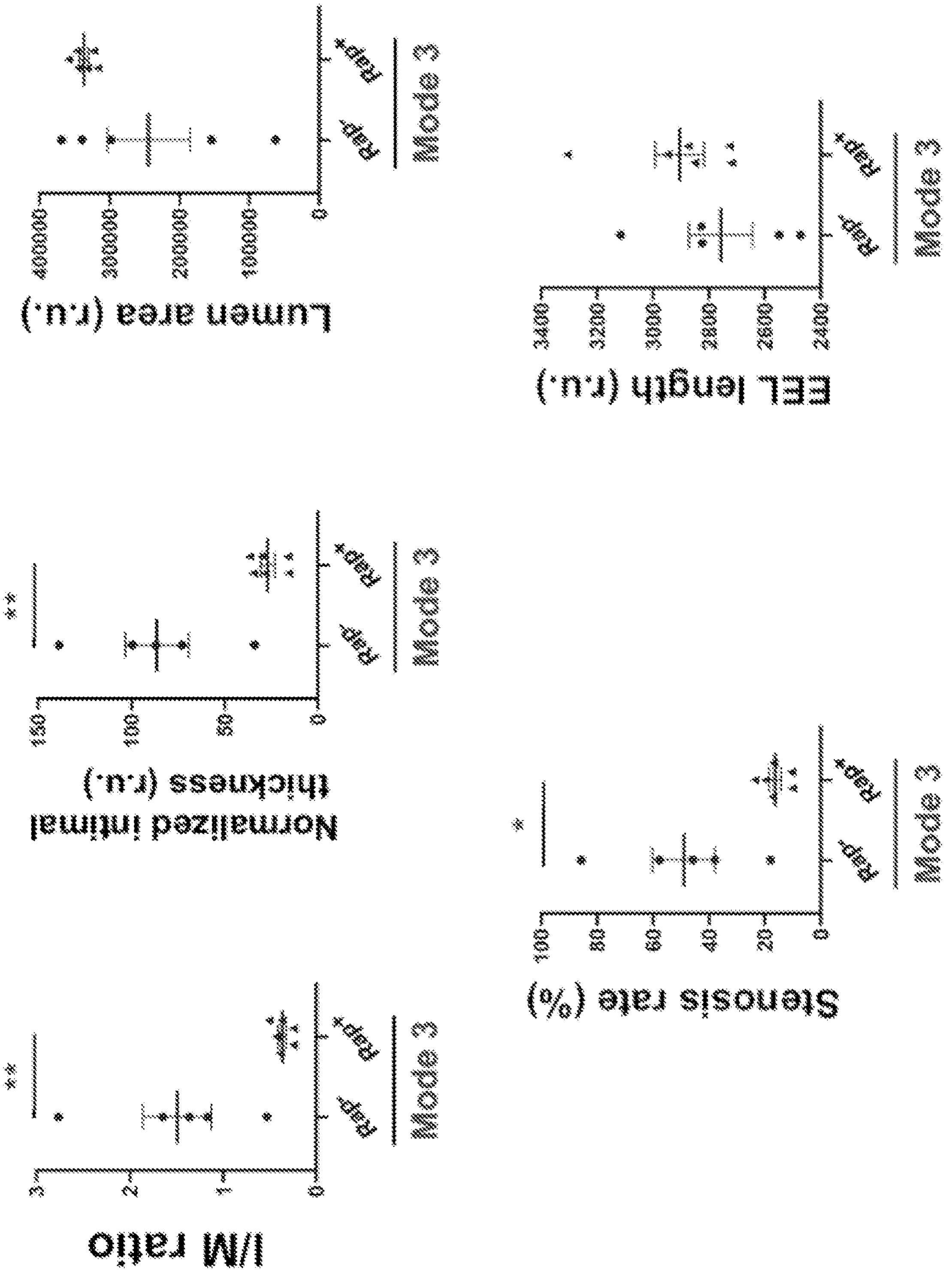
Figure 7A:
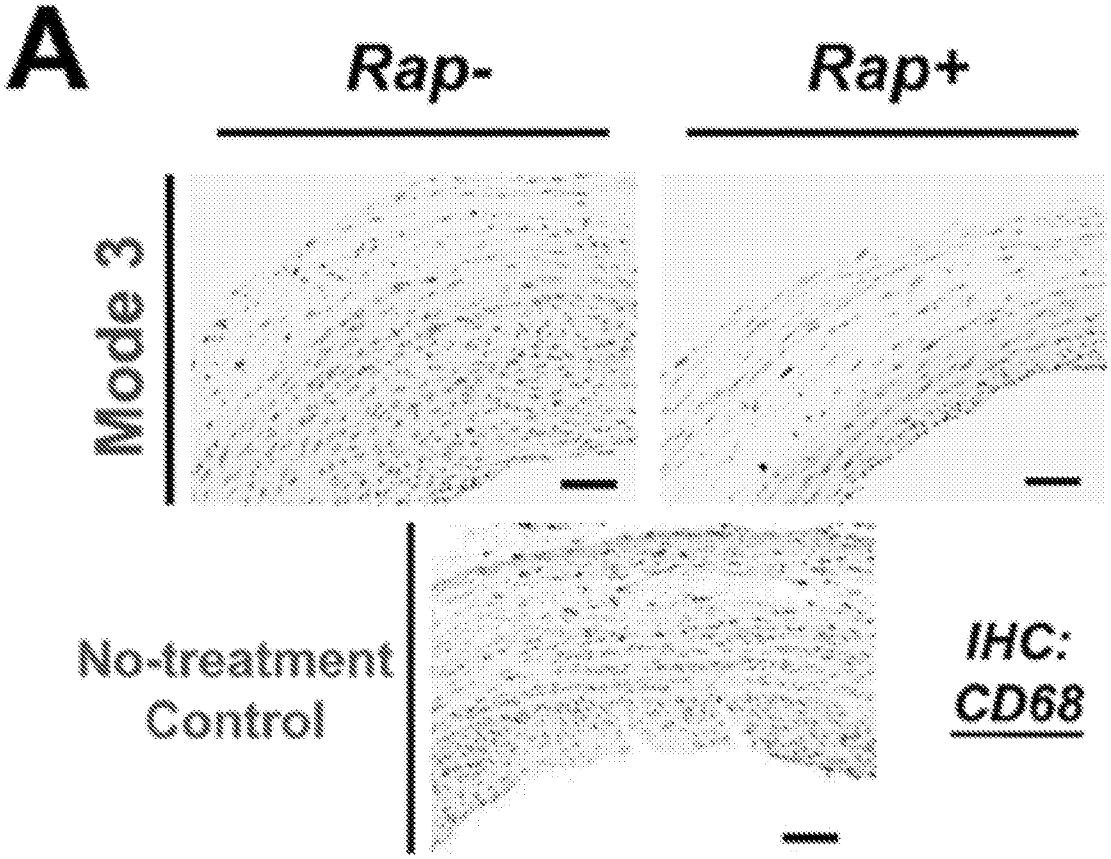
FIGS. 7A-7D show determination of the tissue toxicity of the Mode-3 formulations.
Figure 7B:
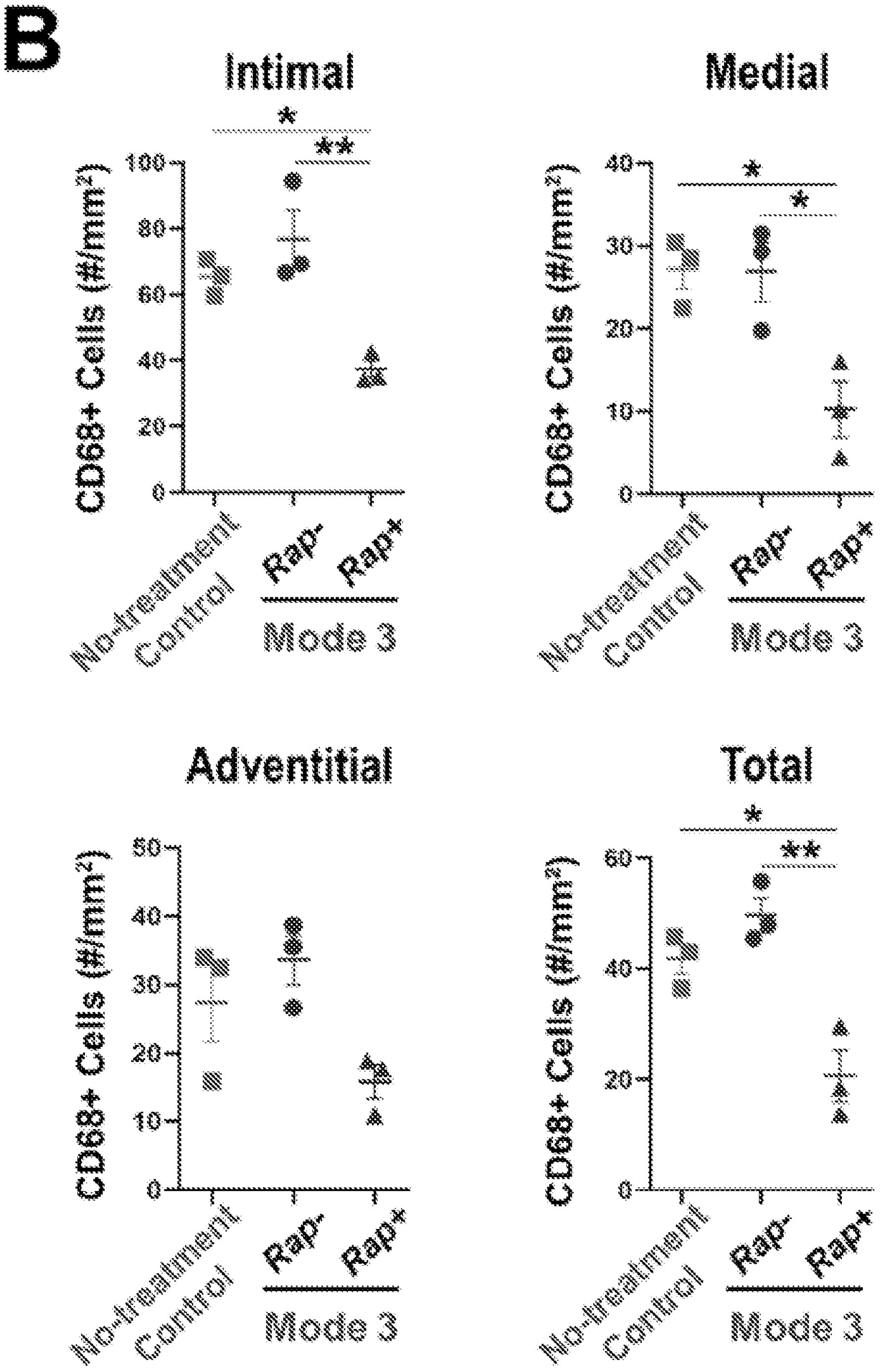
Figure 7C:
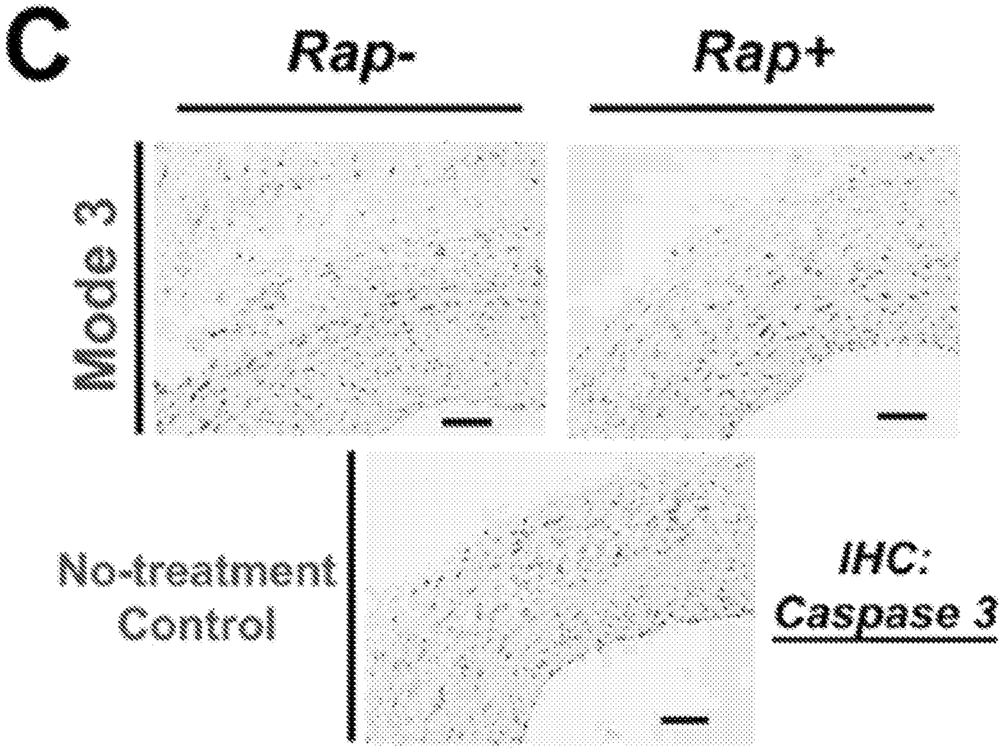
Figure 7D:
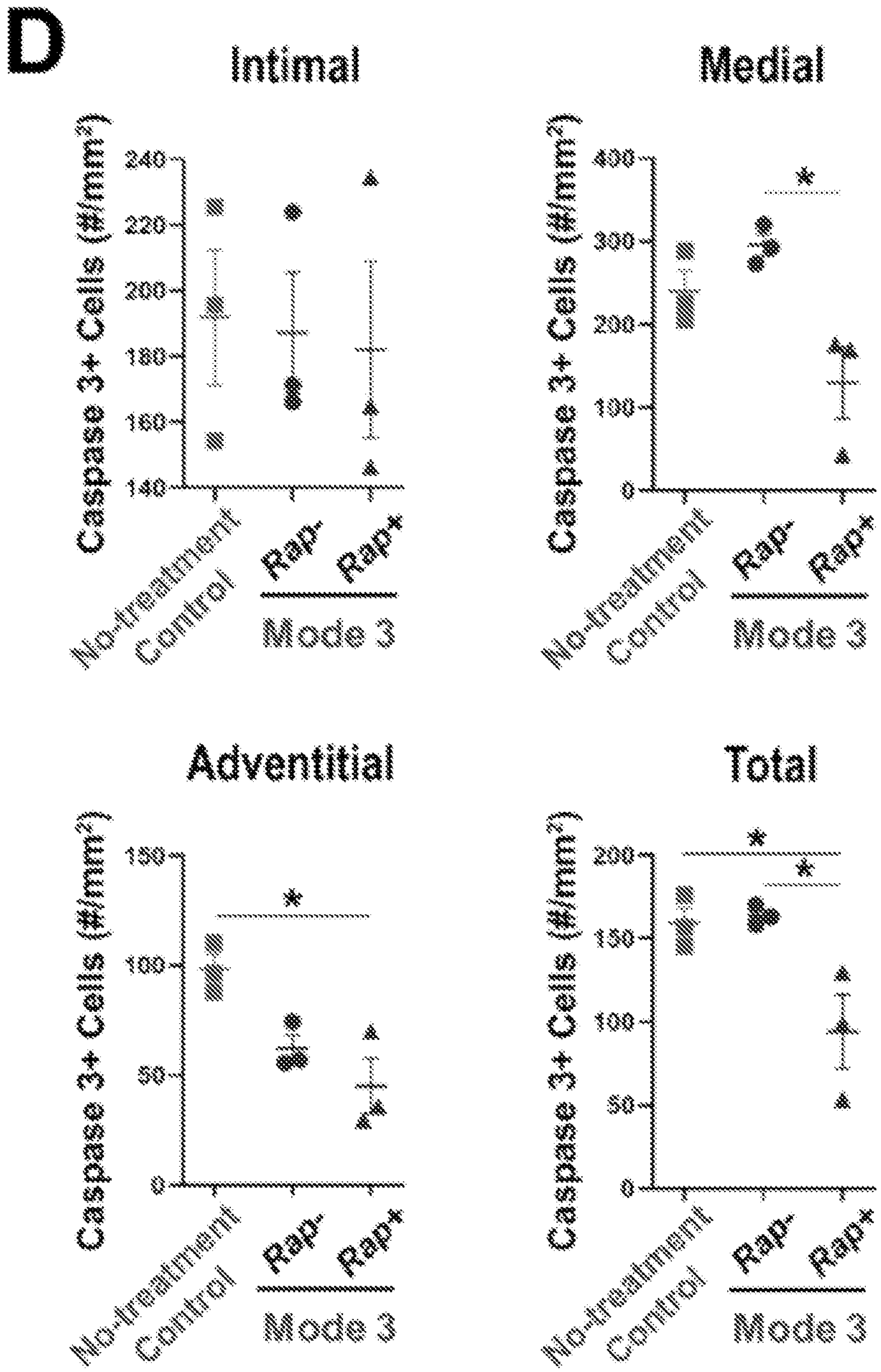

Instead, a pen brush was used to dip into the non-crosslinked UM-NHS solution and paint it onto the outer surface of the injured carotid artery (Mode-3). The entire painting process took less than 30 seconds. It was interesting to note that only 1/10 of the UM-NHS solution was consumed as compared to the soaking approach (Mode-2). To minimize quenching of UM-NHS by $NH_2$-containing molecules (e.g., soluble proteins) in the body fluid, the artery was pre-cleaned prior to painting. To prevent unreacted free UM-NHS or the byproduct (NHS) from diffusing into the surrounding tissues, the artery surface was gently cleansed with gauze immediately after painting. As indicated by the Cy5 fluorescence, UM was effectively sequestered in the adventitial layer after cleaning with gauze (FIG. 6A). Cy5 fluorescence remained visible in the adventitial layer 7 days after application. The fading of fluorescence could be due to quenching, or loss of the Cy5 group possibly due to the hydrolytic and enzymatic cleavage of the ester bond linking the PEG arms onto the UM.

Importantly, morphometric analysis showed that a remarkable IH-mitigating effect was achieved through this painting approach (FIGS. 6A-6D). The I/M ratio was decreased by 75.5% (from 1.50±0.37 to 0.37±0.04) in the animal group applied with rapamycin-loaded UM-NHS compared to the empty UM control. Similarly, the NIT and stenosis rate were reduced by 68.9% (from 86.5±17.1 to 26.9±3.7) and 66.6% (from 49.2±11.2% to 16.4±2.1%), respectively. In accordance, the lumen area increased by 37.7% (from 244743 to 336968) albeit without reaching statistical significance (p=0.12). The EEL length also increased, though without reaching statistical significance.

The next important question concerned the potential toxicity of the adventitial modification by UM-NHS (regardless of drug loading). Compared to the un-treated group (no adventitial modification), painting with empty UM-NHS did not increase the inflammation and apoptosis markers in any of the artery tissue layers. Instead, UM-NHS reduced apoptosis in the adventitial layer (FIGS. 7A-7D).

Figure 11A:
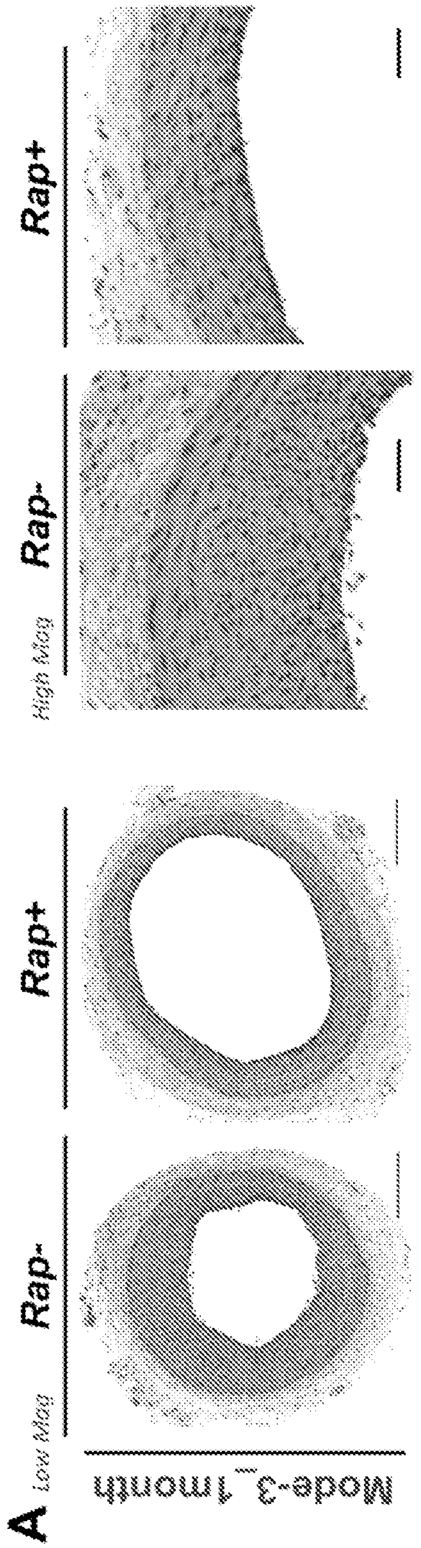
FIGS. 11A-11B show longer-term IH-mitigating effect of painting rapamycin-loaded adventitia-adhesive UM-NHS (Mode-3). Open surgery followed by periadventitial application of UM-NHS (without or with rapamycin) was performed as described for FIGS. 6A-6D. At post-surgery 30 days arteries were harvested for cross-section preparation and H&E staining.
Figure 11B:
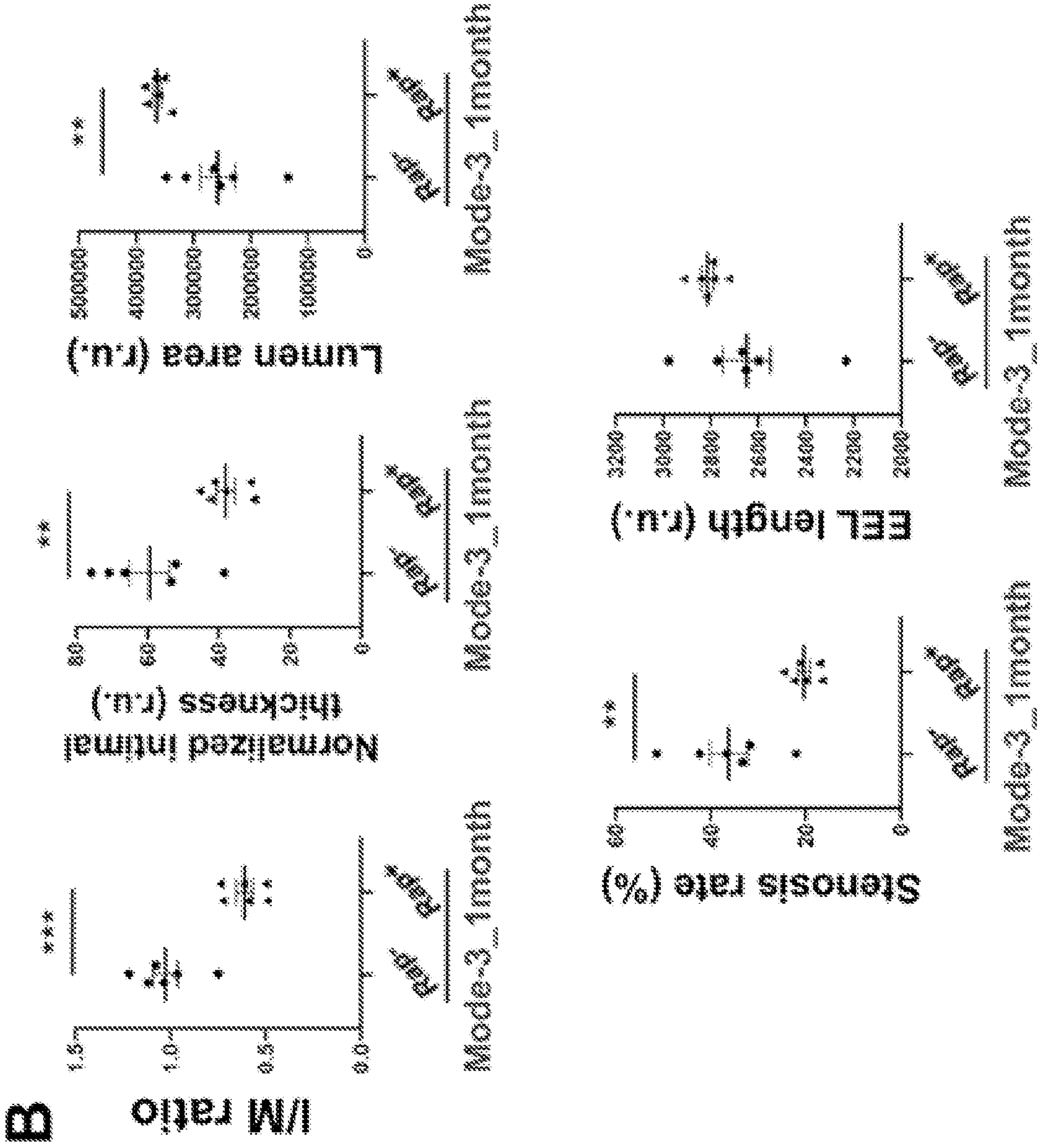

Rapamycin reduced CD68 staining in the vessel wall, and also lowered the overall number of caspase-3 positive cells, as compared between the conditions with and without drug loaded. Thus, Mode-3 appeared to be a highly desirable approach for periadventitial drug delivery, although it is not directly comparable to Mode-2 considering that these two modes were performed at different times, multiple variables between these experiments, including incubation time (30 seconds versus 15 min) and application method (painting versus soaking). Moreover, since macrophage infiltration occurs early following arterial injury and the inflammation reaction may resolve later, the assays using specimens collected at day-14 may not capture such early-phase events. Nonetheless, it was found that Mode-3 provides an easy and quick application to efficaciously stymie IH progression. To further test the efficacy of Mode-3 for a longer term, another set of experiments was performed where arteries were collected at 1 month after surgery (FIGS. 11A-11B). The I/M ratio, NIT, and stenosis rate decreased (with vs without drug) significantly by 40.4% (from 1.03±0.07 to 0.61±0.04), 35.8% (from 59.5±5.7 to 38.2±2.5), and 43.7% (from 36.3±4.1% to 20.4±1.3%), respectively. The lumen area significantly increased by 41.7% (from 257089±30104 to 364264±7553). The overall vessel size (EEL length) was slightly enlarged although the change was not statistically significant (p=0.14).

Discussion

Herein is reported a simple modality of drug delivery aimed at perivascular application to mitigate IH following surgical vascular reconstructions. The delivery platform is a unimolecular micelle (UM) with NHS ester terminal groups that enable tissue-adhesion. Its periadventitial application is simple, requiring only a pen brush, and quick, within 30 seconds. Yet, the therapeutic outcome is remarkable, with a 75% decrease of IH without obvious tissue damage. Thus, the most prominent feature of this prototype is its simplicity, efficacy, and safety. Given an estimated ~15 to 70% of 1-year failure rate of open vascular reconstructions for which no preventive measures are clinically available, this prototype merits further development.

Open surgical procedures remain a major approach for vascular reconstruction. These mainly include coronary artery bypass graft surgery, vein grafting for peripheral arteries, and renal dialysis access, collectively accounting for over 1 million cases annually in the US alone. Unfortunately, there remains a lack of effective methods to prevent these grafts from post-operation failure which primarily results from IH. One potential option to prevent vein graft failure is external stents to mitigate IH by appropriating the turbulent flow. However, this method is ineffective for the perianastomotic lesions (at the two ends of the graft) where IH is particularly severe, occurring in the crucial period of 1-24 months after grafting. In fact, the first trial of external stent revealed worsened patency at anastomotic lesions as compared to the non-stent group. Clearly, there remains a critical medical need for a perivascular drug delivery method that is particularly suited for IH-mitigating therapy following open vascular surgery.

Previous endeavors led to a UM/hydrogel delivery system for open surgery that proved effective in restricting IH in a rat model. However, bulky hydrogel was required to keep UM in place after perivascular application, even though the gel is subject to dislocation and it also evokes inflammation upon decomposition. To resolve these major shortcomings, a gel-free painting paradigm was conceived to immobilize UM directly onto the adventitia through stable covalent bonds.

A painting method has not been previously reported for periadventitial applications to treat IH. In other applications (e.g., skin wound healing), various tissue-adhesive molecules have been tried, including aldehydes, biotin/avidin, and a collagen-binding fibronectin domain. However, limitations exist, particularly thinking of clinical applications that impinge on the tender vascular tissues proximal to vital organs such as heart, where the toxicity of aldehydes is a serious concern. While the biotin/avidin pair features high binding affinity and low toxicity, neither biotin nor avidin is tissue-adhesive. Although fibronectin adheres to collagen-containing tissues, the binding is non-covalent and hence unstable; moreover, a fibronectin domain per se is a signaling molecule that possibly elicits pro-IH complications. Catechol-based adhesives represent another important bio-inspired adhesive technology. However, the underlying Dopa chemistry submits to influences of redox, pH, metal ion chelating, and surface drying condition etc., and to a propensity of crosslinking into polymers (herein unwanted, as demonstrated by Mode-1). As such, this technology demands stringent control of the microenvironment of application site. NHS ester was chosen for covalent UM-tissue bonding because of the following main advantages:

1) NHS ester is highly desired in protein conjugation applications for its quick robust reaction with the $NH_2$ group; 2) the reaction generates an amide bond, which is relatively stable; 3) the by-product, NHS, is generally regarded as minimally toxic and can be easily cleansed, as herein demonstrated using gauze. It is thus not a surprise that NHS esters have been widely used in protein industry and bioengineering applications.

When initially designing the Mode-1 periadventitial UM-NHS application, drug-loading capacity was prioritized. A crosslinked UM network enabled loading of 6 mg of rapamycin for each animal, a dosage expected to markedly reduce IH based on a previous report. Unfortunately, severe tissue-damaging side effects were observed, as evident from the fibrotic, inflammatory, and apoptotic markers in the adventitial and periadventitial tissues. Since this occurred in both animal groups receiving crosslinked UM with or without rapamycin, it was suspected that UM crosslinking per se might be a problem. Indeed, implanted synthetic polymers with a significant mass are often recognized as "alien" by the immune systems, and inflammatory/fibrogenic responses may hence set off. Moreover, the rigidity of a crosslinked network may impose mechanic stress on the vessel promoting inflammation/fibrosis. By contrast, tissue damage was markedly ameliorated in Mode-2, where UM-NHS alone rather than a bulky crosslinked network was applied. It was further observed that by soaking the vessel for extended time in Mode-2, UM-NHS might over-react with the tissue potentially causing harm. Therefore, a painting approach (Mode-3) was used for a faster and cleaner UM-NHS application.

The Mode-3 application is quick (completable in 30 seconds) and requires much less rapamycin-loaded UM-NHS (only ~1/10 of that used in Mode-2). Yet, the outcome from Mode-3 was superior: a 75% reduction of IH and nearly undetectable tissue damage. There are several possible explanations for this. First, quick painting followed by immediate removal of excess UM-NHS solution could avoid damage of overreaction with tissues. Second, without forming a crosslinked network, the small sized (~50 nm in diameter) individual UM-NHS molecule/nanoparticle can readily infiltrate into the adventitia. In contrast, the crosslinked network (Mode-1) cannot infiltrate but rather acts as a rigid "cast" that impinges on the vessel thereby prompting damage. Third, the adventitia is essentially a "sponge" composed of various scaffolding extracellular matrix proteins such as collagen, elastin, and fibrillin fibers, which confer extended surface area for UM's covalent attachment via the NHS ester/$NH_2$ reaction. As such, the UM conjugated onto the adventitia constitute a drug reservoir, with a much larger volume than it would appear to be if calculated based on the outer surface of the vessel. Last yet importantly, with the durable UM slowly and locally releasing rapamycin into the adjacent media/intima layer, the minimum effective drug dosage can be substantially reduced.

Therefore, this Mode-3 direct painting modality of local drug delivery appears to meet the basic criteria for therapeutically viable methods with regard to a translatability to the clinical setting. 1) Mode-3 is highly effective in hampering IH with reduced rapamycin dosage. 2) This method appears to be tissue-friendly without causing obvious damage. 3) It provides local delivery to minimize systemic complications. 4) The UM nanoparticle has excellent stability in comparison with self-assembled multimolecular nanoparticles since the UM nanoparticle is formed by a single molecule containing only covalent bonds. 5) Rapamycin release from UM is sustainable at least for 2 months, consistent with the previous report. 6) This painting method is easy and quick to apply without needing sophisticated devices—a feature critically important for a potential clinical utility and commercialization.

CONCLUSIONS

Currently, there is no approved therapy to prevent IH-caused postoperative failure of surgical reconstructions, which are performed to treat atherosclerotic stenosis. In response to this critical medical need, a painting modality was developed for perivascular drug delivery to mitigate IH. Literally, with minimal manipulation, the vessel adventitia may have been turned into a self-serving drug reservoir for controlled release. This method is quick and easy in application, and effective in curbing injury-induced IH without causing tissue damage. However, IH in humans often develops in the background of other disease conditions and progresses for a long term. In this regard, a result from previous studies is encouraging, namely, treating IH with rapamycin-loaded UM in rats at earlier time points could have an effect extended beyond the end of drug release. Nevertheless, future research is warranted to test the long-term IH-mitigating efficacy of this UM-NHS painting modality in other models such as hypercholesterolemic Zuker rats.

A Painting Method Using Adhesive Nanoparticles (ahNP) as a Modular Drug Delivery System Currently there are two major clinical treatments for the stenotic cardiovascular disease (atherosclerosis): angioplasty and bypass surgery. In either case, post-operative IH develops, ultimately re-occluding the vessel lumen. Drug-eluting stents (DES) represent a major medical advance in alleviating post-angioplasty IH. However, this endovascular device cannot be used in the case of bypass surgery. Therefore, an IH-mitigating method suitable for open vascular reconstruction has been highly sought after for preventing failure of revascularizations. Success in this task requires innovations in both drug target and drug delivery method. It has been discovered that DOT1L is a master pathogenic target and the disclosed tissue adhesive drug-delivery nanosystem is suitable for use upon open vascular reconstruction. Importantly, the combination of a DOT1L inhibitor as a test drug delivered in the adhesive nanoplatform was effective in abating IH yet without endothelial toxicity.

The disclosed painting method is easy, quick, and gentle, imposing little stress on the vessel. The unimolecular micelle ahNP, though minute in mass, are highly capable of drug loading (>20% wt). The hydrophilicity rendered by the sulfo-NHS ester terminal group prohibits ahNP from endocytosis (hence destruction in endosomes), prolonging its durability. Rather, ahNP are sequestered on extracellular matrix (ECM) proteins. The byproduct (sulfo-NHS) is soluble and readily removable with absorbents like gauze. Compared to conventional methods (i.e. perivascular gel), the drug dose for effective IH-mitigation can be reduced by ~100 fold. A rationale is that each NP adhering to adventitial ECM may function like "drip irrigation," releasing drug locally, slowly yet durably. It is thus conceivable that the disclosed system exerts no or low toxicity; indeed, it is not toxic to the endothelium. Finally, the ahNP is amenable to optimization (e.g. size, drug release kinetics) and utility as a localized delivery vehicle for other drugs.

There has been a lack of reports of using adhesive nanoparticles for periadventitial treatment of IH, although various tissue-adhesive molecules have been tried in other applications (e.g., skin wound healing) and have shown major defects. Aldehyde is a concern as it relates to fibrotic toxicity. Fibronectin adheres to collagen non-covalently and, hence, unstably. Catechol-based adhesives are attractive biomaterials. However, the underlying Dopa chemistry submits to microenvironmental conditions, e.g. redox, pH, metal ion chelating, surface drying, and the like. Sulfo-NHS ester is a moiety widely applied in pharmaceutical protein industry due to its quick robust reactivity with the $NH_2$ groups abundant in the adventitial ECM, the resultant stable amide bond, and low or no toxicity of the byproduct sulfo-NHS, which is highly soluble hence readily removable with gauze.

Preclinical Therapeutic Outcomes Using Healthy Rats and Obese Zucker Rats

It was previously reported that DOT1L could be a novel epigenetic target for IH mitigation. While perivascular administration of Pinometostat reduced IH in a rat model, DOT1L-specific silencing recapitulated this effect. Further, it has been reported that DOT1L's atherogenic role and genetic variations associated with atherosclerosis. Indeed, DOT1L was elevated in rat and human arteries that underwent IH. For translation, using adhesive nanoparticles (ahNP) a gentle and quick painting method was developed.

Figure 15:
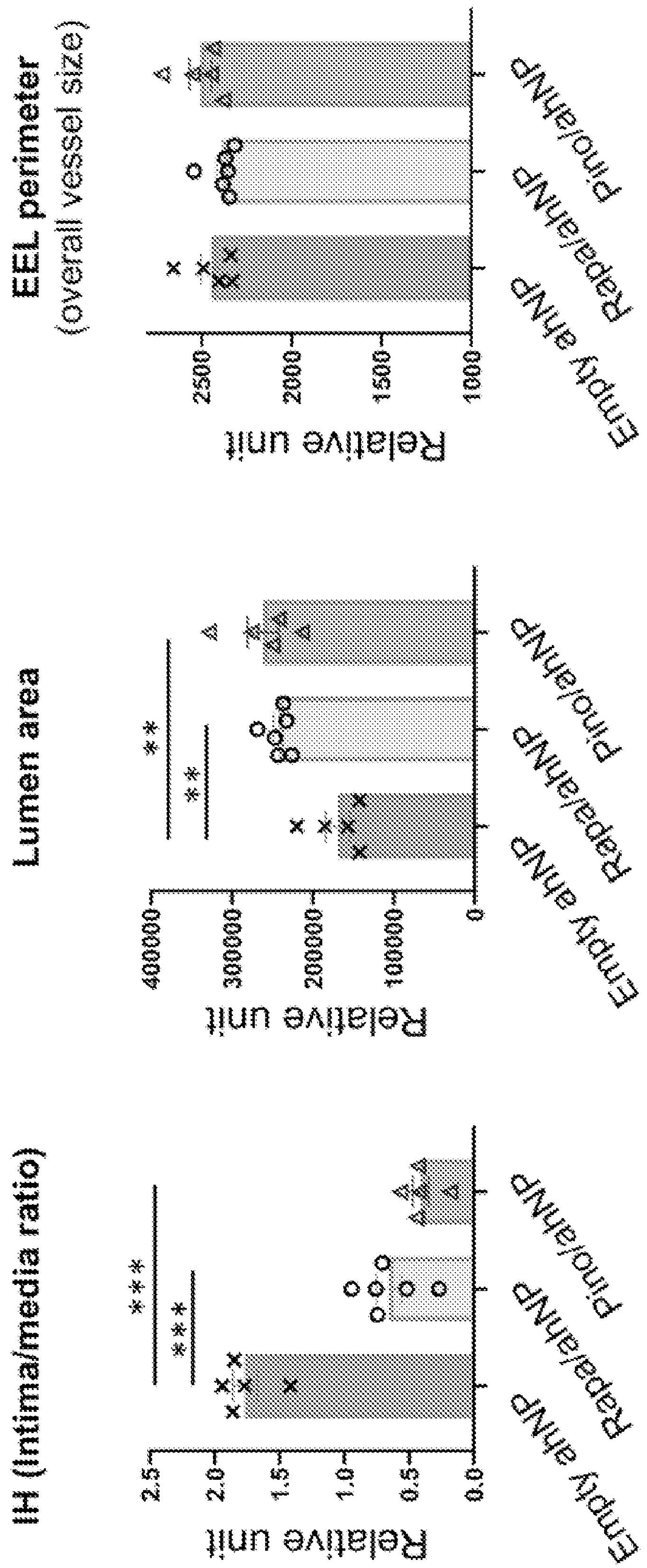
FIG. 15 shows Pinometostat (DOT1L-selective inhibitor) loaded ahNP mitigates IH induced by balloon injury in carotid arteries of obese Zucker rats. A, adventitia; M, media; N, neointima (between arrows). IH (1/M area ratio) was measured on artery sections of post-injury day-28. Mean±SEM, n=5-6 rats. ANOVA and Tukey test: P<0.0, *P<0.001.
Figures 16A, 16B:
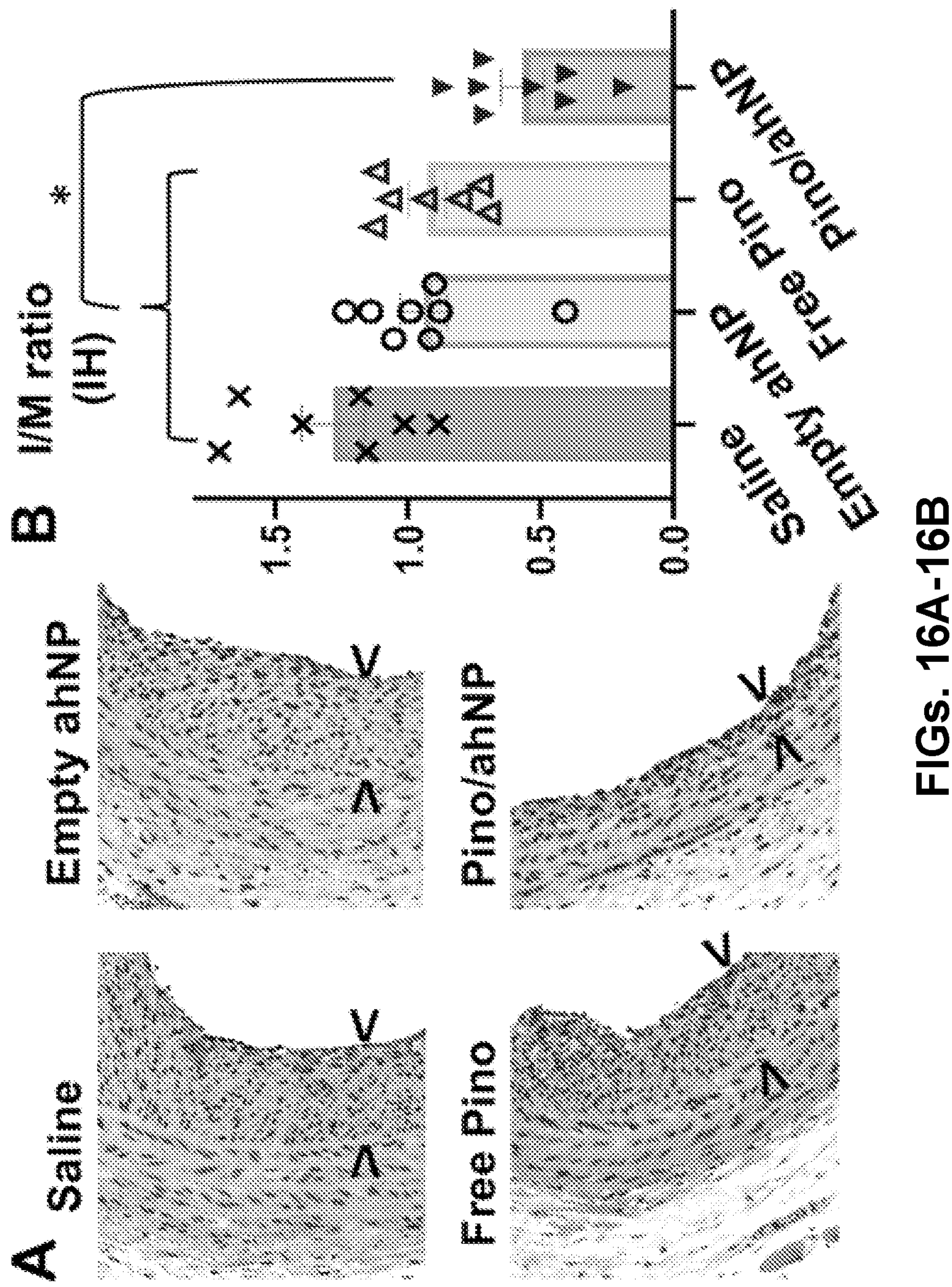
FIGS. 16A-16B show Pinometostat (DOT1L-selective inhibitor) loaded adhesive nanoparticles (ahNP) mitigate IH in rat carotid arteries induced by balloon injury in Sprague-Dawley rats. A, adventitia; M, media; N, neointima (between arrows). IH (1/M area ratio) was measured on artery sections of post-injury day-14 (see FIG. 16B). Mean±SEM, n=6-8 rats. ANOVA and Tukey test: *p<0.05. Scale: 100 μm.
Figure 17:
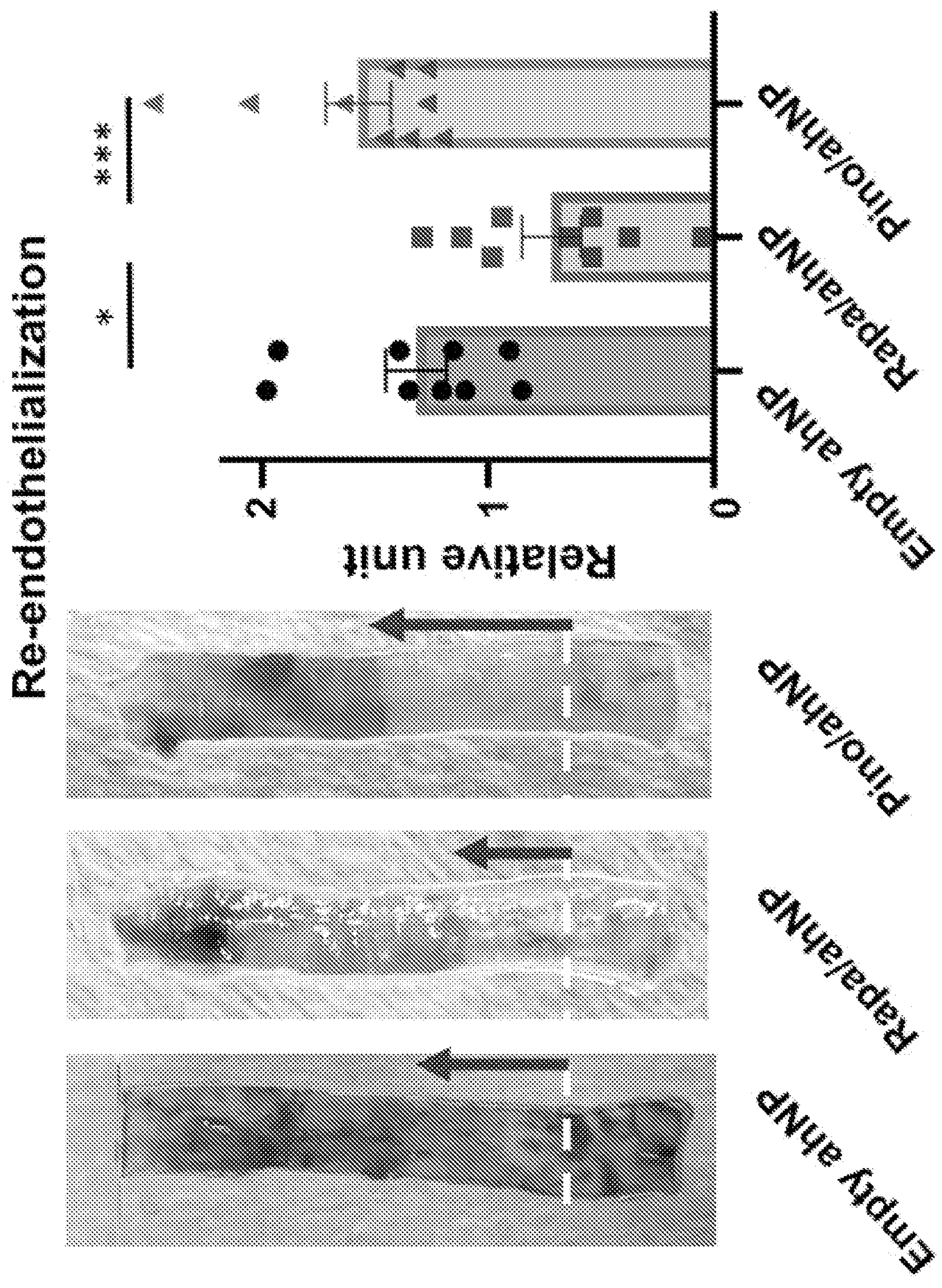
FIG. 17 shows Pinometostat-loaded adhesive nanoparticle (ahNP) is non-toxic to the endothelium. The endothelium was damaged by balloon angioplasty in rat common carotid arteries (Evans Blue-stained). Dotted line indicates baseline. Arrows show endothelium recovery. Rapamycin (rapa)-loaded ahNP retarded reendothelialization compared to the empty ahNP.

Pinometostat applied in this nanosystem abated IH and enlarged lumen without shrinking the vessel size in obese Zucker rats bearing human-like disease backgrounds, with the results persisting long-term (a month of treatment) (FIG. 15). Remarkably, the effective drug dose (100 μg per rat) was only 1% of that used in the traditional perivascular hydrogel approach. In the short-term (2 weeks) tests using Sprague-Dawley rats (no disease background), the disclosed system loaded with Pinometostat at the same dose also significantly reduced IH (FIGS. 16A-16B). Importantly, although rapamycin (the drug used clinically on drug-eluting stents) loaded in ahNP also reduced IH (FIG. 15), it caused toxicity to the endothelium as indicated by retarded re-endothelialization compared to the empty ahNP control (FIG. 17). Delayed re-endothelialization (recovery after injury) is known to cause life-threatening thrombosis. However, the disclosed formulation did not delay reendothelialization.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

REFERENCES

1. Akkapeddi, P. et al, Construction of homogeneous antibody-drug conjugates using site-selective protein chemistry, Chemical Science 7(5) (2016) 2954-2963.
2. Al-Jaishi, A. A. et al, Patency rates of the arteriovenous fistula for hemodialysis: a systematic review and meta-analysis, Am J Kidney Dis 63(3) (2014) 464-78.
3. Almasri, J. et al, A systematic review and meta-analysis of revascularization outcomes of infrainguinal chronic limb-threatening ischemia, J Vasc Surg 68(2) (2018) 624-633.
4. Chen, G. et al, A review on core-shell structured unimolecular nanoparticles for biomedical applications, Adv Drug Deliv Rev 130 (2018) 58-72.
5. Chen, G. et al, Unimolecular Micelle-Based Hybrid System for Perivascular Drug Delivery Produces Long-Term Efficacy for Neointima Attenuation in Rats, Biomacromolecules 18(7) (2017) 2205-2213.
6. Chivers, C. E. et al, How the biotin-streptavidin interaction was made even stronger: investigation via crystallography and a chimaerictetramer, Biochem J 435(1) (2011) 55-63.
7. de Vries, M. R. et al, Inflammation in Vein Graft Disease, Frontiers in Cardiovascular Medicine 5 (2018) 3.
8. de Vries, M. R. et al, Vein graft failure: from pathophysiology to clinical outcomes, Nature reviews. Cardiology 13(8) (2016) 451-470.
9. Emelia, J. B. et al, Heart Disease and Stroke Statistics-2018 Update: A Report From the American Heart Association, Circulation 137(12) (2018) e67-e492.
10. Fowkes, F. G. et al, Peripheral artery disease: epidemiology and global perspectives, Nat Rev Cardiol 14(3) (2017) 156-170.
11. Gao, W. et al, Nanoparticle-Hydrogel: A Hybrid Biomaterial System for Localized Drug Delivery, Ann Biomed Eng 44(6) (2016) 2049-2061.
12. Goel, S. A. et al, Mechanisms of post-intervention arterial remodelling, Cardiovasc Res 96(3) (2012) 363-71.
13. Goodney, P. P. et al, National trends in lower extremity bypass surgery, endovascular interventions, and major amputations, J Vasc Surg 50(1) (2009) 54-60.
14. Harris, G. et al, *Borrelia burgdorferi* protein BBK32 binds to soluble fibronectin via the N-terminal 70-kDa region, causing fibronectin to undergo conformational extension, J Biol Chem 289(32) (2014) 22490-9.
15. Harskamp, R. E. et al, Saphenous vein graft failure after coronary artery bypass surgery: pathophysiology, management, and future directions, Ann Surg 257(5) (2013) 824-33.
16. Herrington, W. et al, Epidemiology of Atherosclerosis and the Potential to Reduce the Global Burden of Atherothrombotic Disease, Circ Res 118(4) (2016) 535-46.
17. Hess, C. N. et al, Saphenous vein graft failure after coronary artery bypass surgery: insights from PREVENT IV, Circulation 130(17) (2014) 1445-51.
18. Huang, Y. et al, Nullifying epigenetic writer DOT1L attenuates neointimal hyperplasia, Atherosclerosis 308 (2020) 22-31.
19. Jain, M. et al, Smooth muscle cell-specific fibronectin-EDA mediates phenotypic switching and neointimal hyperplasia, The Journal of Clinical Investigation 130(1) (2020) 295-314.
20. Kithcart, A. P. et al, ACC/AHA Versus ESC Guidelines for Diagnosis and Management of Peripheral Artery Disease: JACC Guideline Comparison, J Am Coll Cardiol 72(22) (2018) 2789-2801.
21. Kord Forooshani, P. et al, Recent approaches in designing bioadhesive materials inspired by mussel adhesive protein, Journal of Polymer Science Part A: Polymer Chemistry 55(1) (2017) 9-33.
22. Krishnan, S. et al, Growth and characterization of succinic acid single crystals, Crystal Research and Technology 42(11) (2007) 1087-1090.
23. Leichner, C. et al, N-Hydroxysulfosuccinimide Esters versus Thiomers: A Comparative Study Regarding Mucoadhesiveness, Molecular Pharmaceutics 16(3) (2019) 1211-1219.
24. Liu, H. et al, Less harmful acidic degradation of poly (lacticco-glycolic acid) bone tissue engineering scaffolds through titania nanoparticle addition, Int J Nanomedicine 1(4) (2006) 541-545.
25. LoPachin, R. M. et al, Molecular Mechanisms of Aldehyde Toxicity: A Chemical Perspective, Chemical Research in Toxicology 27(7) (2014) 1081-1091.
26. Lynn, A. D. et al, Characterization of the in vitro macrophage response and in vivo host response to poly (ethylene glycol)-based hydrogels, J Biomed Mater Res A 93(3) (2010) 941-53.
27. Meschaninova, M. I., Novel Convenient Approach to the Solid-Phase Synthesis of Oligonucleotide Conjugates, Molecules 24(23) (2019).
28. Nair, L. et al, Folic Acid Conjugated 6-Valerolactone-Poly(ethylene glycol) Based Triblock Copolymer as a Promising Carrier for Targeted Doxorubicin Delivery, PLOS ONE 8(8) (2013) e70697.
29. Nam, K. et al, Controlling Coupling Reaction of EDC and NHS for Preparation of Collagen Gels Using Ethanol/Water Co-Solvents, Macromolecular Bioscience 8(1) (2008) 32-37.
30. Osbun, J. W. et al, A Multicenter, Single-Blind, Prospective Randomized Trial to Evaluate the Safety of a Polyethylene Glycol Hydrogel (Duraseal Dural Sealant System) as a Dural Sealant in Cranial Surgery, World Neurosurgery 78(5) (2012) 498-504.

31. Park, T. G. Degradation of poly(lactic-co-glycolic acid) microspheres: effect of copolymer composition, Biomaterials 16(15) (1995) 1123-30.
32. Peng, H. T. et al, PEGylation of Melittin: Structural Characterization and Hemostatic Effects, Journal of Bioactive and Compatible Polymers 25(1) (2010) 75-97.
33. Qazvini, N. T. et al, Synthesis and characterization of gelatin nanoparticles using CDI/NHS as a non-toxic cross-linking system, J Mater Sci Mater Med 22(1) (2011) 63-9.
34. Rafuse, M. et al, Layer-specific arterial micromechanics and microstructure: Influences of age, anatomical location, and processing technique, J Biomech 88 (2019) 113-121.
35. Salva, R. et al, Polymersome shape transformation at the nanoscale, ACS Nano 7(10) (2013) 9298-311.
36. Sam, S. et al, Semiquantitative Study of the EDC/NHS Activation of Acid Terminal Groups at Modified Porous Silicon Surfaces, Langmuir 26(2) (2010) 809-814.
37. Schild, A. F. et al, Arteriovenous fistulae vs. arteriovenous grafts: a retrospective review of 1,700 consecutive vascular access cases, J Vasc Access 9(4) (2008) 231-5.
38. Shi, X. et al, Periadventitial Application of Rapamycin-Loaded Nanoparticles Produces Sustained Inhibition of Vascular Restenosis, PLOS ONE 9(2) (2014) e89227.
39. Suto, T. et al, The immunobiology of mTOR in autoimmunity, J Autoimmun 110 (2020) 102373.
40. Taggart, D. P. et al, A Randomized Trial of External Stenting for Saphenous Vein Grafts in Coronary Artery Bypass Grafting, Ann Thorac Surg 99(6) (2015) 2039-45.
41. Wang, B. et al, A paradigm of endothelium-protective and stent-free anti-restenotic therapy using biomimetic nanoclusters, Biomaterials 178 (2018) 293-301.
42. Wang, B. et al, PERK Inhibition Mitigates Restenosis and Thrombosis: A Potential Low-Thrombogenic Anti-restenotic Paradigm, JACC Basic Transl Sci 5(3) (2020) 245-263.
43. Zhao, L. et al, An intraocular drug delivery system using targeted nanocarriers attenuates retinal ganglion cell degeneration, Journal of Controlled Release 247 (2017) 153-166.

What is claimed is:

1. A method for treating or preventing intimal hyperplasia in a subject, the method comprising applying a composition comprising unimolecular micelles to adventitia of a vessel in the subject, wherein the composition is free from hydrogel.

2. The method of claim 1, wherein the unimolecular micelles comprise N-hydroxysuccinimide ester (NHS) terminal groups, aldehyde terminal groups, dopamine terminal groups, or any combination thereof.

3. The method of claim 2, wherein the NHS terminal groups comprise sulfo-NHS terminal groups.

4. The method of claim 2, wherein the NHS terminal groups form amide bonds with the adventitia.

5. The method of claim 2, wherein the unimolecular micelles comprise a structure

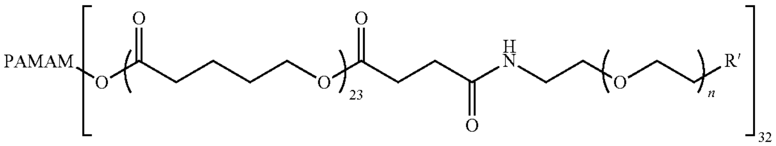

wherein PAMAM comprises polyamidoamine dendrimers;

wherein n is from about 10 to about 230; and wherein each R' in the unimolecular micelles is individually selected from the NHS ester, a methoxy group, or a fluorescent label.

6. The method of claim 5, wherein the fluorescent label comprises Cy5, ICG, AF647, Cy7-azide, IR-820, CY7.5-NH2, DY-547, DY-647, Cy5.5, DY-700-COOH, DY-676-$NH_2$, NileBlue, NileRed, Hostasol, Norbonenyl coumarin, amino-coumarin, nitrobenzoxadiazole (NBD), rhodamine, fluorescein, BODIPY, or any combination thereof.

7. The method of claim 1, wherein the unimolecular micelles have an average molecular weight of from about 15 kDa to about 520 kDa.

8. The method of claim 1, wherein the composition further comprises a drug for treating intimal hyperplasia.

9. The method of claim 8, wherein the drug comprises rapamycin, sirolimus, paclitaxel, apabetalone, JQ1, EPZ5676, centrinone-B, GSK2606414, EED226, UNC1999, tubastatin-A, disulfiram, halofugenone, resveratrol, a DOT1L inhibitor, or any combination thereof.

10. The method of claim 9, wherein the DOT1L inhibitor comprises pinometostat (EPZ5676).

11. The method of claim 8, wherein the composition comprises from about 0.1 to about 20 wt % of the drug.

12. The method of claim 1, wherein the applying the composition to the adventitia comprises pen-brush painting the composition to the vessel.

13. The method of claim 1, wherein the subject is a mammal.

14. The method of claim 1, wherein IH is prevented or reduced for a period of at least 2 weeks.

15. The method of claim 2, wherein the NHS ester terminal group reacts with an amine in an extracellular matrix (ECM) protein to form an amide bond, releasing NHS or a derivative thereof.

16. The method of claim 15, wherein the derivative of NHS is sulfo-NHS and the method further comprises removing the sulfo-NHS from an adventitial site of application.

17. The method of claim 8, wherein performing the method delivers a dose of from about 5 μg per kg of body weight to about 10 mg per kg of body weight of the drug to the vessel adventitia.

18. A unimolecular micelle comprising a structure

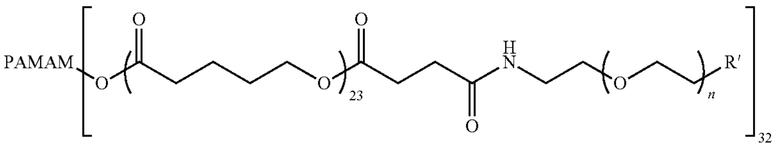

wherein PAMAM comprises polyamidoamine dendrimers;

wherein n is from about 10 to about 230; and wherein each R' in the unimolecular micelles is individually selected from the NHS ester, a methoxy group, or a fluorescent label.

19. The unimolecular micelle of claim 18, wherein the unimolecular micelle has an average molecular weight of at least about 15 kDa.

20. The unimolecular micelle of claim 18, wherein the fluorescent label comprises Cy5, ICG, AF647, Cy7-azide, IR-820, CY7.5-$NH_2$, DY-547, DY-647, Cy5.5, DY-700-COOH, DY-676-$NH_2$, NileBlue, NileRed, Hostasol, Norbonenyl coumarin, Amino-coumarin, nitrobenzoxadiazole (NBD), rhodamine, fluorescein, BODIPY, or any combination thereof.

* * * * *